US011414657B2

(12) United States Patent
Rahdar et al.

(10) Patent No.: US 11,414,657 B2
(45) Date of Patent: Aug. 16, 2022

(54) MODIFIED CRISPR RNA AND MODIFIED SINGLE CRISPR RNA AND USES THEREOF

(71) Applicant: Ionis Pharmaceuticals, Inc., Carlsbad, CA (US)

(72) Inventors: Meghdad Rahdar, San Diego, CA (US); Thazha P. Prakash, Carlsbad, CA (US); Eric E. Swayze, Encinitas, CA (US); C. Frank Bennett, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/737,723

(22) PCT Filed: Jun. 29, 2016

(86) PCT No.: PCT/US2016/040191
§ 371 (c)(1),
(2) Date: Dec. 18, 2017

(87) PCT Pub. No.: WO2017/004261
PCT Pub. Date: Jan. 5, 2017

(65) Prior Publication Data
US 2018/0179521 A1 Jun. 28, 2018

Related U.S. Application Data

(60) Provisional application No. 62/256,649, filed on Nov. 17, 2015, provisional application No. 62/233,281, filed on Sep. 25, 2015, provisional application No. 62/186,363, filed on Jun. 29, 2015.

(51) Int. Cl.
| | |
|---|---|
| *C12N 15/11* | (2006.01) |
| *C12N 15/113* | (2010.01) |
| *C12N 15/85* | (2006.01) |
| *C07H 21/02* | (2006.01) |
| *C12N 9/22* | (2006.01) |
| *C12N 15/10* | (2006.01) |
| *C07H 21/00* | (2006.01) |
| *C12N 7/00* | (2006.01) |
| *C12N 9/96* | (2006.01) |
| *C12N 15/90* | (2006.01) |
| *A61K 38/00* | (2006.01) |
| *A61K 48/00* | (2006.01) |

(52) U.S. Cl.
CPC ............ *C12N 15/11* (2013.01); *C07H 21/00* (2013.01); *C12N 7/00* (2013.01); *C12N 9/22* (2013.01); *C12N 9/96* (2013.01); *C12N 15/102* (2013.01); *C12N 15/111* (2013.01); *C12N 15/907* (2013.01); *A61K 38/00* (2013.01); *A61K 48/00* (2013.01); *C12N 2310/20* (2017.05); *C12N 2310/31* (2013.01); *C12N 2310/315* (2013.01); *C12N 2310/321* (2013.01); *C12N 2310/3231* (2013.01); *C12N 2310/3341* (2013.01); *C12N 2310/344* (2013.01); *C12N 2310/351* (2013.01); *C12N 2740/15043* (2013.01); *C12N 2750/14343* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 8,361,725 B2 | 1/2013 | Russell et al. |
| 8,546,553 B2 | 10/2013 | Martinez et al. |
| 8,673,568 B2 | 3/2014 | Weill et al. |
| 8,697,359 B1 | 4/2014 | Zhang et al. |
| 8,771,766 B2 | 7/2014 | Manoury et al. |
| 8,771,945 B1 | 7/2014 | Zhang et al. |
| 8,795,965 B2 | 8/2014 | Zhang et al. |
| 8,865,406 B2 | 10/2014 | Zhang et al. |
| 8,871,445 B2 | 10/2014 | Cong et al. |
| 8,889,356 B2 | 11/2014 | Zhang et al. |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,921,332 B2 | 12/2014 | Choulika et al. |
| 8,932,814 B2 | 1/2015 | Cong et al. |
| 8,945,839 B2 | 2/2015 | Zhang et al. |
| 8,993,233 B2 | 3/2015 | Zhang et al. |

(Continued)

FOREIGN PATENT DOCUMENTS

| | | | |
|---|---|---|---|
| CN | 105907785 A | 8/2016 |
| EP | 2771468 B1 | 2/2015 |

(Continued)

OTHER PUBLICATIONS

Sproat et al., Highly efficient chemical synthesis of 2'-0-methyloligoribonucleotides and tetrabiotinylated derivatives; novel probes that are resistant to degradation by RNA or DNA specifac nucleases. Nucleic Acids Research,vol. 1 7 No. 9 1989. p. 3373-3386 (Year: 1989).*

Fluiter et al., The Therapeutic Potential of LNA-Modified siRNAs:Reduction of Off-Target Effects by Chemical Modification of the siRNA Sequence. Methods in Molecular Biology, siRNA and miRNAGene Silencing, vol. 487, Ch 9, p. 189-203. Humana Press 2009 (Year: 2009).*

(Continued)

*Primary Examiner* — Maria Marvich
(74) *Attorney, Agent, or Firm* — Knobbe, Martens, Olson & Bear, LLP

(57) ABSTRACT

The present disclosure provides compounds comprising modified oligonucleotides for use in CRISPR. In certain embodiments, such modified oligonucleotides provide improved properties of crRNA. In certain embodiments, such modified oligonucleotides provide improved properties of scrRNA.

12 Claims, 7 Drawing Sheets
Specification includes a Sequence Listing.

(56) References Cited

U.S. PATENT DOCUMENTS

| | | |
|---|---|---|
| 8,999,641 B2 | 4/2015 | Zhang et al. |
| 9,023,649 B2 | 5/2015 | Mali et al. |
| 9,068,179 B1 | 6/2015 | Liu et al. |
| 9,074,199 B1 | 7/2015 | Chavez et al. |
| 9,102,936 B2 | 8/2015 | Zeiner et al. |
| 9,149,049 B2 | 10/2015 | Manoury et al. |
| 9,163,284 B2 | 10/2015 | Liu et al. |
| 9,228,208 B2 | 1/2016 | Frendewey et al. |
| 9,267,135 B2 | 2/2016 | Church et al. |
| 9,637,739 B2 | 5/2017 | Siksnys et al. |
| 9,790,490 B2 | 10/2017 | Zhang et al. |
| 9,822,372 B2 | 11/2017 | Zhang et al. |
| 9,834,791 B2 | 12/2017 | Zhang et al. |
| 9,840,713 B2 | 12/2017 | Zhang et al. |
| 10,000,772 B2 | 6/2018 | Doudna et al. |
| 2014/0068797 A1 | 3/2014 | Doudna et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0189896 A1 | 7/2014 | Zhang et al. |
| 2014/0242664 A1 | 8/2014 | Zhang et al. |
| 2014/0242699 A1 | 8/2014 | Zhang et al. |
| 2014/0287938 A1 | 9/2014 | Zhang et al. |
| 2014/0310830 A1 | 10/2014 | Zhang et al. |
| 2014/0357530 A1 | 12/2014 | Zhang et al. |
| 2015/0020223 A1 | 1/2015 | Zhang et al. |
| 2015/0050699 A1 | 2/2015 | Siksnys et al. |
| 2015/0059010 A1* | 2/2015 | Cigan .............. C12N 15/8241 800/260 |
| 2015/0232882 A1 | 8/2015 | Zhang et al. |
| 2015/0232883 A1 | 8/2015 | Dahlman et al. |
| 2015/0240261 A1 | 8/2015 | Siksnys et al. |
| 2015/0247150 A1 | 9/2015 | Zhang et al. |
| 2015/0252358 A1* | 9/2015 | Maeder .............. C12N 15/86 424/93.2 |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0356239 A1 | 12/2015 | Zhang et al. |
| 2015/0376587 A1 | 12/2015 | May et al. |
| 2016/0024523 A1 | 1/2016 | Joung et al. |
| 2016/0024524 A1 | 1/2016 | Joung et al. |
| 2016/0068822 A1 | 3/2016 | Zhang et al. |
| 2016/0115489 A1 | 4/2016 | Zhang et al. |
| 2016/0130609 A1 | 5/2016 | Doudna et al. |
| 2016/0138008 A1 | 5/2016 | Doudna et al. |
| 2016/0153004 A1 | 6/2016 | Zhang et al. |
| 2016/0153005 A1 | 6/2016 | Zhang et al. |
| 2016/0153006 A1 | 6/2016 | Zhang et al. |
| 2016/0175462 A1 | 6/2016 | Zhang et al. |
| 2016/0186213 A1 | 6/2016 | Zhang et al. |
| 2016/0215300 A1 | 7/2016 | May et al. |
| 2016/0272965 A1 | 9/2016 | Zhang et al. |
| 2016/0281072 A1 | 9/2016 | Zhang et al. |
| 2016/0289675 A1* | 10/2016 | Ryan .............. C12N 15/907 |
| 2016/0317677 A1 | 11/2016 | Bhatia et al. |
| 2016/0340660 A1 | 11/2016 | Zhang et al. |
| 2016/0340661 A1 | 11/2016 | Cong et al. |
| 2016/0348073 A1 | 12/2016 | Meissner et al. |
| 2016/0354487 A1 | 12/2016 | Zhang et al. |
| 2016/0355795 A1 | 12/2016 | Ran et al. |
| 2016/0355796 A1 | 12/2016 | Davidson et al. |
| 2016/0355797 A1 | 12/2016 | Konermann et al. |
| 2017/0051310 A1 | 2/2017 | Doudna et al. |
| 2017/0073674 A1* | 3/2017 | Maeder .............. C12N 7/00 |
| 2017/0166893 A1 | 6/2017 | Doudna et al. |
| 2018/0066242 A1 | 3/2018 | Zhang et al. |

FOREIGN PATENT DOCUMENTS

| | | | |
|---|---|---|---|
| EP | 2848690 A1 | 3/2015 | |
| EP | 2784162 B1 | 4/2015 | |
| EP | 2764103 B1 | 8/2015 | |
| EP | 2896697 B1 | 9/2015 | |
| EP | 2940140 A1 | 11/2015 | |
| EP | 2898075 B1 | 3/2016 | |
| EP | 2931898 B1 | 3/2016 | |
| EP | 2998400 A1 | 3/2016 | |
| EP | 3031921 A1 | 6/2016 | |
| EP | 2921557 B1 | 7/2016 | |
| EP | 3045537 A1 | 7/2016 | |
| EP | 3064585 A1 | 9/2016 | |
| EP | 2840140 B1 | 11/2016 | |
| EP | 2825654 B1 | 4/2017 | |
| EP | 2931897 B1 | 11/2017 | |
| EP | 306620 | 3/2018 | |
| WO | WO-2006044663 A2 * | 4/2006 | ........... C12N 15/111 |
| WO | WO 2013/176772 | 11/2013 | |
| WO | WO 2014/018423 | 1/2014 | |
| WO | WO 2014/093718 | 1/2014 | |
| WO | WO 2014/093595 | 6/2014 | |
| WO | WO 2014/093622 | 6/2014 | |
| WO | WO 2014/093635 | 6/2014 | |
| WO | WO 2014/093655 | 6/2014 | |
| WO | WO 2014/093661 | 6/2014 | |
| WO | WO 2014/093694 | 6/2014 | |
| WO | WO 2014/093701 | 6/2014 | |
| WO | WO 2014/093709 | 6/2014 | |
| WO | WO 2014/093712 | 6/2014 | |
| WO | WO 2014/144592 | 9/2014 | |
| WO | WO 2014/144761 | 9/2014 | |
| WO | WO 2014/145599 | 9/2014 | |
| WO | WO 2014/191128 | 12/2014 | |
| WO | WO 2014/204724 | 12/2014 | |
| WO | WO 2014/204725 | 12/2014 | |
| WO | WO 2014/204726 | 12/2014 | |
| WO | WO 2014/204727 | 12/2014 | |
| WO | WO 2014/204728 | 12/2014 | |
| WO | WO 2014/204729 | 12/2014 | |
| WO | WO 2015/006747 | 1/2015 | |
| WO | WO 2015/026885 | 2/2015 | |
| WO | WO 2015/048577 | 4/2015 | |
| WO | WO 2015/051169 | 4/2015 | |
| WO | WO 2015/051173 | 4/2015 | |
| WO | WO 2015/051214 | 4/2015 | |
| WO | WO 2015/070083 | 5/2015 | |
| WO | WO 2015/071474 | 5/2015 | |
| WO | WO 2015/089351 | 6/2015 | |
| WO | WO 2015/089354 | 6/2015 | |
| WO | WO 2015/089419 | 6/2015 | |
| WO | WO 2015/089427 | 6/2015 | |
| WO | WO 2015/089462 | 6/2015 | |
| WO | WO 2015/089465 | 6/2015 | |
| WO | WO 2015/089473 | 6/2015 | |
| WO | WO 2015/089489 | 6/2015 | |
| WO | WO 2016/028682 | 2/2016 | |
| WO | WO 2016/049258 | 3/2016 | |
| WO | WO 2016/073990 | 5/2016 | |
| WO | WO 2016/089433 | 6/2016 | |
| WO | WO 2016/094867 | 6/2016 | |
| WO | WO 2016/094872 | 6/2016 | |
| WO | WO 2016/094874 | 6/2016 | |
| WO | WO 2016/094880 | 6/2016 | |
| WO | WO 2016/100951 | 6/2016 | |
| WO | WO 2016/100974 | 6/2016 | |
| WO | WO 2016/106236 | 6/2016 | |
| WO | WO 2016/106244 | 6/2016 | |
| WO | WO 2016/123230 | 8/2016 | |
| WO | WO-2016/166340 | 10/2016 | |
| WO | WO 2016/186745 | 11/2016 | |
| WO | WO 2016/205613 | 12/2016 | |
| WO | WO 2016/205711 | 12/2016 | |
| WO | WO 2016/205759 | 12/2016 | |
| WO | WO 2016/205764 | 12/2016 | |
| WO | WO 2017/004261 | 1/2017 | |
| WO | WO 2017/053431 | 3/2017 | |
| WO | WO 2017/053729 | 3/2017 | |

(56) References Cited

FOREIGN PATENT DOCUMENTS

| | | |
|---|---|---|
| WO | WO 2017/091630 | 6/2017 |
| WO | WO 2017/093969 | 6/2017 |
| WO | WO 2017/136794 | 8/2017 |
| WO | WO 2017/181107 | 10/2017 |
| WO | WO 2017/190664 | 11/2017 |
| WO | WO 2018/098383 | 5/2018 |

OTHER PUBLICATIONS

Braasch et al., Biodistribution of phosphodiester and phosphorothioate siRNA (Bioorg Med Chem Lett, 2004, 14:1139-1143) (Year: 2004).*
Braasch et al., RNA Interference in Mammalian Cells by Chemically-Modified RNA (Biochem, 2003, 42:7967-7975) (Year: 2003).*
Nair et al., Multivalent N-Acetylgalactosamine-Conjugated siRNA Localizes in Hepatocytes and Elicits Robust RNAi-Mediated Gene Silencing (JACS, 2014, 136:16958-16961) (Year: 2014).*
Fu et al., Improving CRISPR-Cas nuclease specificity using truncated guide RNAs (Nat Biotech, 2014, 32:279-284) (Year: 2014).*
Doessing and Vester, Locked and Unlocked Nucleosides in Functional Nucleic Acids, Molecules 2011, 16, 4511-4526.*
Wilbie et al, Delivery Aspects of CRISPR/Cas for in Vivo Genome Editing, Delivery Aspects of CRISPR/Cas for in Vivo Genome Editing, Acc. Chem. Res. 2019, 52, 1555-1564.*
Mout et al, In Vivo Delivery of CRISPR/Cas9 for Therapeutic Gene Editing: Progress and Challenges, Bioconjugate Chem. 2017, 28,880-884.*
Fumoto et al, Targeted Gene Delivery; Importance of Administration Routes, Chapter 1, Intech, 2013, pp. 3-31.*
Appella "Non-natural nucleic acids for synthetic biology" Curr Opin Chem Biol (2009) 13: 687-696.
Karkare et al., "Promising nucleic acid analogs and mimics: characteristic features and applications of PNA, LNA, and morpholino" Appl Microbiol Biotechnol (2006) 71(5): 575-586.
Extended EP Search Report for 16818724.3 dated Nov. 6, 2018.
International Search Report for PCT/US16/040191 dated Sep. 30, 2016.
U.S. Appl. No. 61/652,086, filed May 25, 2012, Jinek et al.
U.S. Appl. No. 61/716,256, filed Oct. 19, 2012, Jinek et al.
U.S. Appl. No. 61/736,527, filed Dec. 12, 2012, Zhang et al.
U.S. Appl. No. 62/093,588, filed Dec. 18, 2014, Collingwood et al.
U.S. Appl. No. 62/239,546, filed Oct. 9, 2015, Collingwood et al.
Agrawal et al., "Role of Toll-like receptors in antisense and siRNA [corrected]." Nat Biotechnol (2004) 22(12): 1533-1537.
Baltimore et al., "Biotechnology. A prudent path forward for genomic engineering and germline gene modification." Science (2015) 348(6230):36-38.
Barrangou et al., "CRISPR provides acquired resistance against viruses in prokaryotes." Science (2007) 315(5819):1709-1712.
Bennett et al., "RNA Targeting Therapeutics: Molecular Mechanisms of Antisense Oligonucleotides as a Therapeutic Platform" Annu Rev Pharmacol Toxicol (2010) 50: 259-293.
Bhaya et al., "CRISPR-Cas systems in bacteria and archaea: Versatile small RNAs for adaptive defense and regulation." Annu Rev Genet (2011) 45:273-297.
Braasch et al., "RNA Interference in Mammalian Cells by Chemically-Modified RNA" Biochemistry (2003) 42(26): 7967-7975.
Burnett et al., "RNA-based therapeutics: current progress and future prospects" Chem Biol (2012) 19(1): 60-71.
Carroll et al., "Genome engineering with targetable nucleases." Annu Rev Biochem (2014) 83:409-439.
Chen et al., "Dynamic imaging of genomic loci in living human cells by an optimized CRISPR/Cas system" Cell (2013) 155(7): 1479-1491.
Chen et al., "Genome-wide CRISPR screen in a mouse model of tumor growth and metastasis." Cell (2015) 160(6):1246-1260.
Chiu et al., "siRNA function in RNAi: a chemical modification analysis" RNA (2003) 9(9): 1034-1048.
Cho et al., "Targeted genome engineering in human cells with the Cas9 RNA-guided endonuclease" Nature Biotech (2013) 31(3): 230-232.
Cong et al., "Multiplex Genome Engineering Using CRISPR/Cas Systems" Science (2015) 339: 819-823.
Cox et al., "Therapeutic genome editing: Prospects and challenges." Nat Med (2015) 21(2):121-131.
Dellinger et al., "Solid-Phase Chemical Synthesis of Phosphonoacetate and Thiophosphonoacetate Oligonucleotides" J Am Chem (2003) 125(4): 940-950.
Doudna et al., "Genome editing. The new frontier of genome engineering with CRISPR-Cas9" Science (2014) 346(6213): 1258096-1-9.
Eckstein "Phosphorothioates, essential components of therapeutic oligonucleotides" Nucleic Acid Ther (2014) 24(6): 377-387.
Fachinetti et al., "DNA sequence-specific binding of CENP-B enhances the fidelity of human centromere function." Dev Cell (2015) 33(3):314-327.
Foust et al., "Therapeutic AAV9-mediated suppression of mutant SOD1 slows disease progression and extends survival in models of inherited ALS" Mol Ther (2013) 21(12): 2148-2159.
Fu et al., "High-frequency off-target mutagenesis induced by CRISPR-Cas nucleases in human cells." Nat Biotechnol (2013) 31(9):822-826.
Fu et al., "Improving CRISPR-Cas nuclease specificity using truncated guide RNAs" Nat Biotechnol (2014) 32(3): 279-284.
Gasiunas et al., "Cas9-crRNA ribonucleoprotein complex mediates specific DNA cleavage for adaptive immunity in bacteria" PNAS (2012) E2579-E2586.
Gilbert et al., "CRISPR-mediated modular RNA-guided regulation of transcription in eukaryotes" Cell (2013) 154(2): 442-451.
Gilbert et al., "Genome-Scale CRISPR-Mediated Control of Gene Repression and Activation" Cell (2014) 159(3): 647-661.
Grushkin "DuPont in CRISPR-Cas patent land grab" Nature Biotech (2016) 34(1): 13.
He et al., "CRISPR-Cas9 genome editing utilizing chemically synthesized RNA" Dharmacon GE Healthcare: Poster 2016.
Hendel et al., "Chemically modified guide RNAs enhance CRISPR-Cas genome editing in human primary cells" Nature Biotech (2015) 33(9): 985-989.
Hsu et al., "Development and applications of CRISPR-Cas9 for genome engineering." Cell (2014) 157(6):1262-1278.
Hsu et al., "DNA targeting specificity of RNA-guided Cas9 nucleases." Nat Biotechnol (2013 31(9):827-832.
Hua et al., "Motor neuron cell-nonautonomous rescue of spinal muscular atrophy phenotypes in mild and severe transgenic mouse models" Genes Dev (2015) 29(3): 288-297.
Jiang et al., "Structural Biology. A Cas9-guide RNA complex preorganized for target DNA recognition" Science (2015) 348(6242): 1477-1481.
Jinek et al, "A programmable dual-RNA-guided DNA endonuclease in adaptive bacterial immunity." Science (2012) 337(6096):816-821.
Jinek et al., "RNA-programmed genome editing in human cells" eLife (2013) 1-9.
Koller et al., "Mechanisms of single-stranded phosphorothioate modified antisense oligonucleotide accumulation in hepatocytes" Nucleic Acids Res (2011) 39(11): 4795-4807.
Konermann et al., "Genome-scale transcriptional activation by an engineered CRISPR-Cas9 complex" Nature (2015) 517(7536): 583-588.
Kuscu et al., "Genome-wide analysis reveals characteristics of off-target sites bound by the Cas9 endonuclease." Nat Biotechnol (2014) 32(7):677-683.
Lander "The Heroes of CRISPR" Cell (2016) 164: 18-28.
Li et al., "Heritable gene targeting in the mouse and rat using a CRISPR-Cas system." Nat Biotechnol (2013) 31(8):681-683.
Lin et al., "Enhanced homology-directed human genome engineering by controlled timing of CRISPR/Cas9 delivery." (2014) eLife 3:e04766.
Makarova et al., "Evolution and classification of the CRISPR-Cas systems." Nat Rev Microbiol 9(6):467-477.

(56) References Cited

OTHER PUBLICATIONS

Mali et al. "RNA-guided human genome engineering via Cas9" Science (2013) 339(6121): 823-826.

Master et al., "A Novel Method for Gene-Specific Enhancement of Protein Translation by Targeting 5'UTRs of Selected Tumor Suppressors" PLOS One (2016) 11(5): 1-23.

McMahon et al., "Gene editing: Notjust for translation anymore." Nat Methods (2012) 9(1):28-31.

Mingozzi et al., "Therapeutic in vivo gene transfer for genetic disease using AAV: progress and challenges" Nat Rev Genet (2011) 12(5): 341-355.

Passini et al., "Antisense Oligonucleotides Delivered to the Mouse CNS Ameliorate Symptoms of Severe Spinal Muscular Atrophy" Sci Trans Med (2011) 3(72): 1-11.

Pattanayak et al., "High-throughput profiling of off-target DNA cleavage reveals RNA-programmed Cas9 nuclease specificity." Nat Biotechnol (2013) 31(9):839-843.

Platt et al., "CRISPR-Cas9 knockin mice for genome editing and cancer modeling" Cell (2014) 159(2): 440-455.

Prakash et al., "Positional effect of chemical modifications on short interference RNA activity in mammalian cells" J Med Chem (2005) 48(13): 4247-4253.

Qi et al., "Repurposing CRISPR as an RNA-guided platform for sequence-specific control of gene expression" Cell (2013) 152(5): 1173-1183.

Qiu et al., "Mutation detection using Surveyor nuclease" Biotechniques (2004) 36(4): 702-707.

Rahdar et al., "Synthetic CRISPR RNA-Cas9-guided genome editing in human cells" PNAS (2015) E7110-E7117.

Ran et al, "In vivo genome editing using *Staphylococcus aureus* Cas9." Nature (2015) 520(7546):186-191.

Seth et al., "Synthesis and Biophysical Evaluation of 2',4'-Coutianed 2'O-Methoxyethyl and 2',4'-Contrained 2'O-Ethyl Nucleic Aci Analogues" J Org Chem (2010) 75(5): 1569-1581.

Smith et al., "Antisense oligonucleotide therapy for neurodegenerative disease" J Clin Invest (2006) 116(8): 2290-2296.

Soutschek et al., "Therapeutic silencing of an endogenous gene by systemic administation of modified siRNAs" Nature (2004) 432(7014): 173-178.

Sternberg et al., "Expanding the Biologist's Toolkit with CRISPR-Cas9." Mol Cell (2015) 58(4):568-574.

Tanenbaum et al., "A protein-tagging system for signal amplification in gene expression and fluorescence imaging" Cell (2014) 159(3): 635-646.

Terns et al., "CRISPR-based adaptive immune systems." Curr Opin Microbiol (2011) 14(3):321-327.

Thakker et al., "Neurochemical and behavioral consequences of widespread gene knockdown in the adult mouse brain by using nonviralRNA interference." PNAS (2004) 101(49):12271.

Tsai et al., "GUIDE-seq enables genome-wide profiling of off-target cleavage by CRISPR-Cas nucleases." Nat Biotechnol (2015) 33(2):187-197.

Wang et al., "One-step generation of mice carrying mutations in multiple genes by CRISPR/Cas-mediated genome engineering." Cell (2013) 153(4):910-918.

Watts et al., "Chemically modified siRNA: tools and applications" Drug Discovery Today (2008) 13:842-855.

Wen et al., "Xylose phosphorylation functions as a molecular switch to regulate proteoglycan biosynthesis." Proc Natl Acad Sci USA (2014) 111(44):15723-15728.

Wiedenheft et al., "RNA-guided genetic silencing systems in bacteria and archaea." Nature (2012) 482(7385):331-338.

Yamano et al., "Crystal Structure of Cpf1 in Complex with Guide RNA and Target DNA" Cell (2016) 165(4): 949-962.

Yu et al., "Single-stranded RNAs use RNAi to potently and allele-selectively inhibit mutant huntingtin expression" Cell (2012) 150(5): 895-908.

Zetsche et al., "Cpf1 is a single RNA-guided endonuclease of a class 2 CRISPR-Cas system" Cell (2015) 163(3): 759-771.

Zincarelli et al., "Analysis of AAV serotypes 1-9 mediated gene expression and tropism in mice after systemic injection" Mol Ther (2008) 16(6): 1073-1080.

International Search Report for PCT/US17/68642 dated Apr. 19, 2018.

Li et al., "Engineering CRISPR-Cpf1 crRNAs and mRNAs to maximize genome editing efficiency" Nat Biomed Eng (2017) 1: 1-21.

Li et al., "Engineering CRISPR-Cpf1 crRNAs and mRNAs to maximize genome editing efficiency" Nat Biomed Eng (2017) supplemental information.

\* cited by examiner

MODIFIED CRISPR RNA AND MODIFIED SINGLE CRISPR RNA AND USES THEREOF

SEQUENCE LISTING

The present application is being filed along with a Sequence Listing in electronic format. The Sequence Listing is provided as a file entitled CORE0134USASEQ_ST25.txt, created Dec. 18, 2017, which is 20 Kb in size. The information in the electronic format of the sequence listing is incorporated herein by reference in its entirety.

BACKGROUND

Use of Cluster Regulatory Interspaced Short Palindromic Repeats (CRISPR) to edit or disable genes has been described. See for example Jinek et al., Scinece 337: 816-821 (2012); Mali et al. Science 339: 823-826 (2013).

SUMMARY

Various CRISPR systems have been described. See for example: WO2013/176772; WO2015/006747; Qi et al., Cell 152: 1 173-1 (2013); Gilbert et al., Cell 154: 1-10 (2013) Jinek et al., Science 337: 816-821 (2012); Mali et al. Science 339: 823-826 (2013); Doudna et al., Science 346: 6213 (2014). See also for example: Zetsche et al., Cell 163: 1-13 (2015). The present invention provides modified oligonucleotides for use as crRNA in CRISPR systems. In certain embodiments, such modified crRNA have improved stability relative to unmodified crRNA. In certain embodiments, modified crRNA is stabilized at the 5' end and/or the 3'. In certain embodiments, such stabilized crRNA is resistant to exonuclease and/or endonucleoase digestion. In certain embodients, modified crRNA have improved affinity for target DNA relative to unmodified crRNA. In certain embodients, modified crRNA have improved selectivity for target DNA relative to unmodified crRNA. In certain embodiments, modified crRNA have improved affinity for tracrRNA relative to unmodified crRNA. In certain embodiments, modified crRNA have improved cellular uptake relative to unmodified crRNA.

In certain such embodiments, the modifications increase affinity for the target DNA allowing the modified crRNA to be shortened while retaining sufficient affinity to hybridize to target DNA and to tracrRNA. Thus, in certain embodiments, modified crRNA is shorter than unmodified crRNA. In certain embodiments, modified crRNA is 40-50 linked nucleosides in length. In certain embodiments, modified crRNA is 35-45 linked nucleosides in length. In certain embodiments, modified crRNA is 30-40 linked nucleosides in length. In certain embodiments, modified crRNA is 25-35 linked nucleosides in length. In certain embodiments, modified crRNA is 20-30 linked nucleosides in length. In certain embodiments, modified crRNA is 25-35 linked nucleosides in length. In certain embodiments, modified crRNA is 20-30 linked nucleosides in length. In certain such embodiments, such shorter crRNA have improved uptake properties. In certain embodiments, modified crRNA are taken into cells without transfection reagents or electroporation. In certain such embodiments, the cells are in an animal. In certain embodiments, the animal expresses Cas9. In certain embodiments, the animal is previously or concomitantly treated with a means of expressing Cas9. In certain such embodiments, such treatment comprises administration of a vector for delivering Cas9. In certain such embodiments, such vector is a viral vector, for example adeno-associated virus (AAV). In certain such embodiments, the viral vector expresses a S. aureus derived Cas9 that fits into an AAV vector.

The present invention also provides modified oligonucleotides for use as scrRNA in CRISPR systems. In certain embodiments, such modified scrRNA have improved stability relative to unmodified scrRNA. In certain embodiments, modified scrRNA is stabilized at the 5' end and/or the 3'. In certain embodiments, such stabilized scrRNA is resistant to exonuclease and/or endonucleoase digestion. In certain embodients, modified scrRNA have improved affinity for scrRNA target DNA relative to unmodified scrRNA. In certain embodients, modified scrRNA have improved selectivity for scrRNA target DNA relative to unmodified scrRNA. In certain embodiments, modified scrRNA have improved affinity for a nuclease relative to unmodified scrRNA. In certain embodiments, modified scrRNA have improved cellular uptake relative to unmodified scrRNA.

In certain such embodiments, the modifications increase affinity for the scrRNA target DNA allowing the modified scrRNA to be shortened while retaining sufficient affinity to hybridize to scrRNA target DNA and a nuclease. Thus, in certain embodiments, modified scrRNA is shorter than unmodified scrRNA. In certain embodiments, modified scrRNA is 40-50 linked nucleosides in length. In certain embodiments, modified scrRNA is 35-45 linked nucleosides in length. In certain embodiments, modified scrRNA is 30-40 linked nucleosides in length. In certain embodiments, modified scrRNA is 25-35 linked nucleosides in length. In certain embodiments, modified scrRNA is 20-30 linked nucleosides in length. In certain embodiments, modified scrRNA is 25-35 linked nucleosides in length. In certain such embodiments, such shorter scrRNA have improved uptake properties. In certain embodiments, modified scrRNA are taken into cells without transfection reagents or electroporation. In certain such embodiments, the cells are in an animal. In certain embodiments, the animal expresses a nuclease that is recognized by the scrRNA (e.g., a Cpf1 nuclease). In certain embodiments, the animal is previously or concomitantly treated with a means of expressing a nuclease that is recognized by the scrRNA (e.g., a Cpf1 nuclease). In certain such embodiments, such treatment comprises administration of a vector for delivering a nuclease that is recognized by the scrRNA (e.g., a Cpf1 nuclease). In certain such embodiments, such vector is a viral vector, for example adeno-associated virus (AAV).

In certain embodiments, the CRISPR system is inhibited after the target gene is edited or the scrRNA target gene is altered. In certain such embodiments, the modified crRNA or modified scrRNA inside a cell is degraded after the target gene or scrRNA target gene has been edited or altered. In certain such embodiments, the nuclease (e.g., Cas9 or a Cpf1 nuclease) continues to be expressed in the cell but is no longer active because it requires crRNA or scrRNA in order to exhibit nuclease activity. In certain such embodiments, off-target effects of the CRISPR system, such as undesired cleavage of an off-target gene, are decreased relative to a CRISPR system in which all of the components necessary for nuclease activity continue to be expressed indefinitely, e.g. by a viral vector. In certain such embodiments, degradation of the modified crRNA or modified scrRNA is facilitated by hybridization to an oligonucleotide complementary to the crRNA or scrRNA. In certain embodiments, degradation of the modified crRNA or modified scrRNA is facilitated by nucleases present in the cell.

In certain embodiments, the CRISPR system is inhibited after the target gene is edited via degradation of a tracrRNA inside the cell. In certain such embodiments, degradation of the tracrRNA is facilitated by hybridization to an oligonucleotide complementary to the tracrRNA. In certain embodiments, degradation of the tracrRNA is facilitated by nucleases present in the cell.

In certain embodiments, the CRISPR system is inhibited after the target gene is edited or the scrRNA target gene is altered via inhibition of the expression of a nuclease (e.g., Cas9 or a Cpf1 nuclease). In certain such embodiments, the nuclease gene is edited or altered by a modified crRNA or a modified scrRNA. In certain embodiments, the nuclease transcript is degraded following hybridization of the nuclease transcript to an oligonucleotide complementary to the nuclease transcript.

The following non-limiting numbered embodiments are provided.

Embodiment 1. A compound comprising a modified crRNA consisting of 20-50 linked nucleosides.

Embodiment 2. The compound of embodiment 1, wherein the modified crRNA is 5'-stabilized.

Embodiment 3. The compound of embodiment 1 or 2, wherein the modified crRNA is 3'-stabilized.

Embodiment 4. The compound of any of embodiments 1-3, wherein the modified crRNA comprises at least one modification that increases affinity of the crRNA for a target DNA.

Embodiment 5. The compound of any of embodiments 1-4, wherein the modified crRNA comprises at least one modification that increases affinity of the crRNA for a tracrRNA.

Embodiment 6. The compound of any of embodiments 1-5, wherein at least one nucleobase of the modified crRNA is thymine.

Embodiment 7. The compound of any of embodiments 1-5, wherein at least one nucleobase of the modified crRNA is a modified nucleobase.

Embodiment 8. The compound of embodiment 7, wherein the modified nucleobase is 5-methyl cytosine.

Embodiment 9. The compound of any of embodiments 1-8, wherein at least one internucleoside linkage of the modified crRNA is a modified internucleoside linkage.

Embodiment 10. The compound of embodiment 9, wherein each internucleoside linkage of the modified crRNA is a modified internucleoside linkage.

Embodiment 11. The compound of embodiment 9 or 10, wherein at least one modified internucleoside linkage is a neutral internucleoside linkage.

Embodiment 12. The compound of embodiment 11, wherein at least one modified internucleoside linkage comprises a methoxypropyl group.

Embodiment 13. The compound of any of embodiments 9-12, wherein at least one modified internucleoside linkage comprises a phosphonoacetate.

Embodiment 14. The compound of any of embodiments 9-13, wherein at least one modified internucleoside linkage comprises a methylphosphonate.

Embodiment 15. The compound of any of embodiments 9-14, wherein at least one modified internucleoside linkage is a phosphorothioate internucleoside linkage.

Embodiment 16. The compound of any of embodiments 9-15, wherein at least two linkages of the modified crRNA are modified internucleoside linkages.

Embodiment 17. The compound of embodiment 16, wherein at least two modified linkages of the modified crRNA are the same as one another.

Embodiment 18. The compound of embodiment 9-17, wherein the modified crRNA comprises two to five phosphorothioate internucleoside linkages at the 5'-end of the crRNA.

Embodiment 19. The compound of embodiment 9-18, wherein the modified crRNA comprises two to five phosphorothioate internucleoside linkages at the 3'-end of the crRNA.

Embodiment 20. The compound of embodiment 9, wherein each internucleoside linkage of the crRNA is a phosphorothioate internucleoside linkage.

Embodiment 21. The compound of any of embodiments 1-20, wherein the modified crRNA does not comprise a 2'-deoxynucleoside.

Embodiment 22. The compound of any of embodiments 1-21, wherein at least one nucleoside of the modified crRNA comprises a modified sugar moiety.

Embodiment 23. The compound of embodiment 22, wherein the 5'-terminal nucleoside of the crRNA comprises a modified sugar moiety.

Embodiment 24. The compound of embodiment 23, wherein the 5'-terminal nucleoside comprises a non-bicyclic 2'-modified sugar moiety Embodiment 25. The compound of embodiment 23, wherein the 5'-terminal nucleoside comprises a bicyclic sugar moiety.

Embodiment 26. The compound of embodiment 23, wherein the 5'-terminal nucleoside comprises a modified sugar moiety selected from among: 2'-O-methyl, 2'-MOE, 2'-F, cEt, and LNA.

Embodiment 27. The compound of any of embodiments 22-26, wherein the internucleoside at the 5'-end of the crRNA is a phosphorothioate internucleoside linkage.

Embodiment 28. The compound of embodiment 22, wherein the modified crRNA has the formula:

$$5'\text{-}Ny_zNy_s\text{-}R\text{-}3'$$

wherein:
each Ny is a nucleoside comprising a sugar moiety independently selected from among an unmodified 2'-deoxy sugar moiety, an unmodified 2'-hydroxy sugar moiety, a 2'-O-methyl modified sugar moiety, a 2'-F modified sugar moiety, and a cEt modified sugar moiety;
z is a neutral internucleoside linkage selected from among methoxypropyl phosphonate and methyl phosphonate;
s is a phosphorothioate internucleoside linkage; and
R is the remaining portion of the crRNA.

Embodiment 29. The compound of embodiment 22, wherein the modified crRNA has the formula:

$$5'\text{-}Nm_sNx_s\text{-}R\text{-}3'$$

wherein:
Nm is a nucleoside comprising a 2'-O-methyl modified sugar moiety;
Nx is a nucleoside comprising a modified sugar moiety selected from among an unmodified 2'-hydroxy sugar moiety and a 2'-F modified sugar moiety;
s is a phosphorothioate internucleoside linkage; and
R is the remaining portion of the crRNA.

Embodiment 30. The compound of any of embodiments 22-29, wherein the 3'-terminal nucleoside of the crRNA comprises a modified sugar moiety.

Embodiment 31. The compound of embodiment 30, wherein the 3'-terminal internucleoside linkage of the crRNA is a phosphorothioate internucleoside linkage.

Embodiment 32. The compound of embodiment 31, wherein the modified crRNA has the formula:

5'-A-Nr$_s$Nr-3' wherein:
each Nr is a nucleoside comprising a modified sugar moiety independently selected from among: 2'-O-methyl, 2'-MOE, 2'-F, cEt, and LNA;
s is a phosphorothioate internucleoside linkage; and
A is the remaining portion of the crRNA.

Embodiment 33. The compound of embodiment 30, wherein the modified crRNA has the formula:

5'-A-Nr$_z$Nr-3' wherein:
each Nr is a nucleoside comprising a modified sugar moiety indepdently selected from among: 2'-O-methyl, 2'-MOE, 2'-F, cEt, and LNA;
z is a phosphate internucleoside linkage or a neutral internucleoside linkage selected from among methoxypropyl phosphonate and methyl phosphonate;
A is the remaining portion of the crRNA;
provided that z is not a phosphate internucleoside linkage if the 3'-terminal Nr comprises a 2'-F sugar moiety.

Embodiment 34. The compound of any of embodiments 22-33, wherein the DNA recognition portion of the modified crRNA comprises at least 7 modified nucleosides, wherein the modified nucleosides each comprise a modified sugar moiety.

Embodiment 35. The compound of embodiment 34, wherein the seven 5'-terminal nucleosides comprise modified sugar moieties.

Embodiment 36. The compound of embodiment 35, wherein the modified sugar moieties of the seven 5'-terminal nucleosides are the same as one another.

Embodiment 37. The compound of embodiment 34, wherein the modified sugar moieties of the seven 5'-terminal nucleosides are each independently selected from among 2'-O-methyl and 2'-F.

Embodiment 38. The compound of embodiment 37, wherein the modified sugar moieties of the seven 5'-terminal nucleosides alternate between 2'-O-methyl and 2'-F.

Embodiment 39. The compound of any of embodiments 1-38, wherein the DNA recognition portion of the crRNA comprises at least one nucleoside comprising an unmodified sugar moiety.

Embodiment 40. The compound of any of embodiments 1-39, wherein the tracrRNA recognition portion of the modified crRNA comprises at least 4 modified nucleosides, wherein the modified nucleosides each comprise a modified sugar moiety.

Embodiment 41. The compound of embodiment 40, wherein each of the modified sugar moieties of the tracrRNA recognition portion are the same as one another.

Embodiment 42. The compound of embodiment 40, wherein each modified sugar moiety of the tracrRNA recognition portion is a cEt.

Embodiment 43. The compound of any of embodiments 1-42, wherein the tracrRNA recognition portion of the crRNA comprises at least one nucleoside comprising an unmodified sugar moiety.

Embodiment 44. The compound of any of embodiments 1-43, wherein the crRNA consists of 42 linked nucleosides.

Embodiment 45. The compound of any of embodiments 1-43, wherein the crRNA consists of 20 to 42 linked nucleosides.

Embodiment 46. The compound of embodiment 45, wherein the crRNA consists of 29 to 32 linked nucleosides.

Embodiment 47. The compound of embodiment 45, wherein the crRNA consists of 32 linked nucleosides.

Embodiment 48. The compound of embodiment 45, wherein the crRNA consists of 29 linked nucleosides.

Embodiment 49. The compound of embodiment 45, wherein the crRNA consists of 20-28 linked nucleosides.

Embodiment 50. The compound of any of embodiments 1-49, wherein the tracrRNA recognition portion of the crRNA consists of 12 or fewer linked nucleosides.

Embodiment 51. The compound of any of embodiments 1-50, wherein the DNA recognition portion of the crRNA consists of 17 or fewer linked nucleosides.

Embodiment 52. The compound of any of embodiments 1-50, wherein the tracrRNA recognition portion of the crRNA comprises a modification selected from alkyne or azide.

Embodiment 53. The compound of any of embodiments 1-52, wherein the compound consists of the crRNA.

Embodiment 54. The compound of any of embodiments 1-52, wherein the compound comprises a conjugate group.

Embodiment 55. The compound of embodiment 54, wherein the conjugate group comprises GalNAc.

Embodiment 56. The compound of any of embodiments 1-55, wherein the nucleobase sequence of the DNA recognition portion of the crRNA is at least 90% complementary to a target DNA.

Embodiment 57. The compound of embodiment 56, wherein the nucleobase sequence of the DNA recognition portion of the crRNA is 100% complementary to a target DNA.

Embodiment 58. A method comprising contacting a cell with the compound of any of embodiments 1-57.

Embodiment 59. The method of embodiment 58, wherein the cell expresses Cas9.

Embodiment 60. A method comprising contacting a cell with the compound of any of embodiments 1-57 and a plasmid that encodes a Cas9 gene.

Embodiment 61. A method comprising contacting a cell with the compound of any of embodiments 1-57 and an mRNA that encodes Cas9.

Embodiment 62. A method comprising contacting a cell with the compound of any of embodiments 1-57 and a plasmid that encodes a Cas9 gene and a tracrRNA.

Embodiment 63. A method comprising contacting a cell with compound of any of embodiments 1-57, a plasmid that encodes a Cas9 gene, and a tracrRNA.

Embodiment 64. The method of any of embodiments 58-63, wherein the crRNA consists of 20 to 32 nucleosides.

Embodiment 65. The method of any of embodiments 58-64, wherein the crRNA is taken up by the cell in the absence of a transfection reagent.

Embodiment 66. A method comprising contacting a cell with the modified crRNA of embodiment 52 and a tracrRNA comprising a modification selected from among: alkyne and azide.

Embodiment 67. The method of embodiment 66 comprising contacting the cell with a plasmid that encodes a Cas9 gene.

Embodiment 68. The method of embodiment 66, wherein the cell expresses Cas9.

Embodiment 69. The method of any of embodiments 58-68, wherein the cell is in an animal Embodiment 70. A method comprising administering to an animal the modified compound of any of embodiments 1-57.

Embodiment 71. The method of embodiment 70, wherein the administration is subcutaneous.

Embodiment 72. The method of embodiment 70, wherein the administration is intrathecal.

Embodiment 73. The method of any of embodiments 70-72 comprising administering a plasmid that encodes a Cas9 gene.

Embodiment 74. The method of any of embodiments 70-72 wherein the animal expresses Cas9.

Embodiment 75. The method of any of embodiments 70-72 comprising administering a plasmid that encodes a Cas9 gene and a tracrRNA.

Embodiment 76. The method of embodiment 75, wherein the plasmid is delivered to cells within the animal via an adeno-associated virus (AAV).

Embodiment 77. The method of embodiment 75, wherein the plasmid is delivered to cells within the animal via a lentivirus.

Embodiment 78. The method of any of embodiments 70-77, wherein a target gene is edited.

Embodiment 79. The method of embodiment 78, wherein the crRNA is degraded after the target gene is edited.

Embodiment 80. The method of embodiment 79, wherein the Cas9 does not exhibit nuclease activity in the absence of the crRNA.

Embodiment 81. The compound of embodiment 5, wherein the tracrRNA is unmodified.

Embodiment 82. The compound of embodiment 5, wherein the tracrRNA is modified.

Embodiment 83. The compound of embodiment 34, wherein the ten 5'-terminal nucleosides comprise modified sugar moieties.

Embodiment 84. The compound of embodiment 83, wherein the modified sugar moieties of the ten 5'-terminal nucleosides are the same as one another.

Embodiment 85. The compound of embodiment 83, wherein the modified sugar moieties of the ten 5'-terminal nucleosides are each independently selected from among 2'-F and 2'-O-methyl.

Embodiment 86. The compound of embodiment 84, wherein the modified sugar moieties of the ten 5'-terminal nucleosides are 2'-F.

Embodiment 87. The compound of embodiment 4, wherein the crRNA motif is selected from among the motifs listed in Table C.

Embodiment 88. The compound of any of embodiments 40 or 81-87, wherein the at least four modified nucleosides of the tracrRNA recognition portion are the four 3'-terminal nucleosides of the crRNA.

Embodiment 89. The compound of embodiment 88, wherein the at least four modified nucleosides of the tracrRNA recognition portion comprise 2'-O-methyl modified sugar moieties.

Embodiment 90. The compound of any of embodiments 40 or 81-89, wherein the tracrRNA recognition portion comprises five modified nucleosides.

Embodiment 91. The compound of any of embodiments 40 or 81-89, wherein the tracrRNA recognition portion comprises six modified nucleosides.

Embodiment 92. The compound of any of embodiments 40 or 81-89, wherein the tracrRNA recognition portion comprises at least seven modified nucleosides.

Embodiment 93. The compound of any of embodiments 40, 81-86, or 88-89, wherein the tracrRNA recognition portion comprises nine modified nucleosides.

Embodiment 94. The compound of any of embodiments 40 or 81-93, wherein at least one modified sugar moiety of the tracrRNA recognition portion is a bicyclic sugar moiety.

Embodiment 95. The compound of embodiment 94, wherein the two 3'-terminal nucleosides of the tracrRNA recognition portion comprise bicyclic sugar moieties.

Embodiment 96. The compound of embodiment 95, wherein the tracrRNA recognition portion comprises five bicyclic sugar moieties.

Embodiment 97. The compound of embodiment 95, wherein the tracrRNA recognition portion comprises six bicyclic sugar moieties.

Embodiment 98. The compound of embodiment 93, wherein the tracrRNA recognition portion comprises nine bicyclic sugar moieties.

Embodiment 99. The compound of any of embodiments 94-98, wherein each bicyclic sugar moiety is independently selected from among cEt and LNA.

Embodiment 100. The compound of embodiment 99, wherein each bicyclic sugar moiety is cEt.

Embodiment 101. The compound of any of embodiments 40 or 88-100, wherein the nucleoside at the 5'-end of the tracrRNA recognition portion of the crRNA comprises a modified sugar moiety.

Embodiment 102. The compound of embodiment 101, wherein the nucleoside at the 5'-end of the tracrRNA recognition portion of the crRNA comprises a bicyclic sugar moiety.

Embodiment 103. The compound of embodiment 102, wherein the bicyclic sugar moiety is cEt or LNA.

Embodiment 104. The compound of embodiment 103, wherein the bicyclic sugar moiety is cEt.

Embodiment 105. The compound of any of embodiments 81-104, wherein the DNA recognition portion of the crRNA comprises at least one nucleoside comprising an unmodified sugar moiety.

Embodiment 106. The compound of embodiment 88, wherein each of the modified sugar moieties of the tracrRNA recognition portion are the same as one another.

Embodiment 107. The compound of any of embodiments 81-106, wherein the tracrRNA recognition portion of the crRNA comprises at least one nucleoside comprising an unmodified sugar moiety.

Embodiment 108. The compound of any of embodiments 81-107, wherein the crRNA consists of 42 linked nucleosides.

Embodiment 109. The compound of any of embodiments 81-107, wherein the crRNA consists of 20 to 42 linked nucleosides.

Embodiment 110. The compound of embodiment 109, wherein the crRNA consists of 29 to 32 linked nucleosides.

Embodiment 111. The compound of any of embodiments 81-86 or 88-109, wherein the crRNA consists of 32 linked nucleosides.

Embodiment 112. The compound of embodiment 109, wherein the crRNA consists of 29 linked nucleosides.

Embodiment 113. The compound of any of embodiments 81-86 or 88-109, wherein the crRNA consists of 20-28 linked nucleosides.

Embodiment 114. The compound of any of embodiments 81-113, wherein the tracrRNA recognition portion of the crRNA consists of 12 or fewer linked nucleosides.

Embodiment 115. The compound of any of embodiments 81-114, wherein the DNA recognition portion of the crRNA consists of 17 or fewer linked nucleosides.

Embodiment 116. The compound of any of embodiments 81-115, wherein the tracrRNA recognition portion of the crRNA comprises a modification selected from alkyne or azide.

Embodiment 117. The compound of any of embodiments 81-116, wherein the compound consists of the crRNA.

Embodiment 118. The compound of any of embodiments 81-116, wherein the compound comprises a conjugate group.

Embodiment 119. The compound of embodiment 118, wherein the conjugate group comprises GalNAc.

Embodiment 120. The compound of embodiment 54 or 118, wherein the conjugate group is lipophilic.

Embodiment 121. The compound of any of embodiments 81-120, wherein the nucleobase sequence of the DNA recognition portion of the crRNA is at least 90% complementary to a target DNA.

Embodiment 122. The compound of embodiment 121, wherein the nucleobase sequence of the DNA recognition portion of the crRNA is 100% complementary to a target DNA.

Embodiment 123. A method comprising contacting a cell with the compound of any of embodiments 81-122.

Embodiment 124. The method of embodiment 123, wherein the cell expresses Cas9.

Embodiment 125. A method comprising contacting a cell with the compound of any of embodiments 81-122 and a plasmid that encodes a Cas9 gene.

Embodiment 126. A method comprising contacting a cell with the compound of any of embodiments 81-122 and an mRNA that encodes Cas9.

Embodiment 127. A method comprising contacting a cell with the compound of any of embodiments 81-122 and a plasmid that encodes a Cas9 gene and a tracrRNA.

Embodiment 128. A method comprising contacting a cell with the compound of any of embodiments 81-122, a plasmid that encodes a Cas9 gene, and a tracrRNA.

Embodiment 129. The method of any of embodiments 123-128, wherein the crRNA is taken up by the cell in the absence of a transfection reagent.

Embodiment 130. The method of any of embodiments 123-129, wherein the cell is in an animal Embodiment 131. A method comprising administering to an animal the modified compound of any of embodiments 81-122.

Embodiment 132. The method of embodiment 131, wherein the administration is subcutaneous.

Embodiment 133. The method of embodiment 131, wherein the administration is intrathecal.

Embodiment 134. The method of embodiment 70 or 131, wherein the administration is to the central nervous system.

Embodiment 135. The method of any of embodiments 131-134 comprising administering a plasmid that encodes a Cas9 gene.

Embodiment 136. The method of any of embodiments 131-134 wherein the animal expresses Cas9.

Embodiment 137. The method of any of embodiments 131-134 comprising administering a plasmid that encodes a Cas9 gene and a tracrRNA.

Embodiment 138. The method of embodiment 135 or 137, wherein the plasmid is delivered to cells within the animal via an adeno-associated virus (AAV).

Embodiment 139. The method of embodiment 135 or 137, wherein the plasmid is delivered to cells within the animal via a lentivirus.

Embodiment 140. The method of any of embodiments 131-139, wherein a target gene is edited.

Embodiment 141. The method of embodiment 140, wherein the crRNA is degraded after the target gene is edited.

Embodiment 142. The method of embodiment 141, wherein the Cas9 does not exhibit nuclease activity in the absence of the crRNA.

Embodiment 143. The method of any of embodiments 69-80 or 130-142, wherein the animal is a human.

Embodiment 144. A method comprising contacting a cell with the compound of any of embodiments 1-57 or 81-122, editing a target gene, and contacting the cell with a second compound that degrades or inhibits the activity or expression of the crRNA, a tracrRNA, or a Cas9 nuclease.

Embodiment 145. The method of embodiment 144, wherein the cell is contacted with the second compound after the target gene has been edited.

Embodiment 146. The method of embodiment 144 or 145, wherein the second compound comprises an oligonucleotide that is complementary to the crRNA.

Embodiment 147. The method of embodiment 146, wherein the crRNA is degraded.

Embodiment 148. The method of embodiment 144 or 145, wherein the second compound comprises an oligonucleotide that is complementary to the tracrRNA.

Embodiment 149. The method of embodiment 148, wherein the tracrRNA is degraded.

Embodiment 150. The method of embodiment 144 or 145, wherein the second compound comprises a crRNA that targets the Cas9 nuclease gene.

Embodiment 151. The method of embodiment 144 or 145, wherein the second compound comprises an oligonucleotide that is complementary to the Cas9 transcript.

Embodiment 152. The method of embodiment 150 or 151, wherein the expression of the Cas9 nuclease is inhibited.

Embodiment 153. The method of any of embodiments 144-152, wherein the cell is in an animal Embodiment 154. The method of embodiment 153, wherein the animal is a human Embodiment 155. The method of embodiment 63 or 128, wherein the tracrRNA is unmodified.

Embodiment 156. The method of embodiment 63 or 128, wherein the tracrRNA is modified.

Embodiment 157. The method of embodiment 63, 128, or 155-156, wherein both the crRNA and the tracrRNA are taken up by the cell in the absence of a transfection reagent.

Embodiment 158. The method of any of embodiments 155-157, wherein the cell is in an animal Embodiment 159. The method of embodiment 158, wherein the animal is a human Embodiment 160. A method of genomic loci visualization comprising contacting a genome with a compound of any of embodiments 1-57 or 81-122.

Embodiment 161. The method of any of embodiments 58-80 or 123-160, wherein editing of off-target genes is reduced relative to editing of off-target genes when unmodified crRNA or a compound comprising more than 50 nucleosides is used in place of the compound comprising the modified crRNA consisting of 20-50 linked nucleosides.

Embodiment 162. A compound comprising a modified scrRNA consisting of 20-50 linked nucleosides.

Embodiment 163. The compound of embodiment 162, wherein the modified scrRNA is 5'-stabilized.

Embodiment 164. The compound of embodiment 162 or 163, wherein the modified scrRNA is 3'-stabilized.

Embodiment 165. The compound of any of embodiments 162-164, wherein the modified scrRNA comprises at least one modification that increases affinity of the scrRNA for a scrRNA target DNA.

Embodiment 166. The compound of any of embodiments 161-165, wherein the modified scrRNA comprises at least one modification that increases affinity of the scrRNA for a nuclease Embodiment 167. The compound of embodiment 166, wherein the nuclease is a Cpf1 nuclease.

Embodiment 168. The compound of any of embodiments 161-167, wherein at least one nucleobase of the modified scrRNA is thymine.

Embodiment 169. The compound of any of embodiments 161-168, wherein at least one nucleobase of the modified scrRNA is a modified nucleobase.

Embodiment 170. The compound of embodiment 169, wherein the modified nucleobase is 5-methyl cytosine.

Embodiment 171. The compound of any of embodiments 161-170, wherein at least one internucleoside linkage of the modified scrRNA is a modified internucleoside linkage.

Embodiment 172. The compound of embodiment 171, wherein each internucleoside linkage of the modified scrRNA is a modified internucleoside linkage.

Embodiment 173. The compound of embodiment 171 or 172, wherein at least one modified internucleoside linkage is a neutral internucleoside linkage.

Embodiment 174. The compound of embodiment 173, wherein at least one modified internucleoside linkage comprises a methoxypropyl group.

Embodiment 175. The compound of any of embodiments 171-174, wherein at least one modified internucleoside linkage comprises a phosphonoacetate.

Embodiment 176. The compound of any of embodiments 171-175, wherein at least one modified internucleoside linkage comprises a methylphosphonate.

Embodiment 177. The compound of any of embodiments 171-176, wherein at least one modified internucleoside linkage is a phosphorothioate internucleoside linkage.

Embodiment 178. The compound of any of embodiments 171-177, wherein at least two linkages of the modified scrRNA are modified internucleoside linkages.

Embodiment 179. The compound of embodiment 178, wherein at least two modified linkages of the modified scrRNA are the same as one another.

Embodiment 180. The compound of any of embodiments 171-179, wherein the modified scrRNA comprises two to five phosphorothioate internucleoside linkages at the 5'-end of the scrRNA.

Embodiment 181. The compound of any of embodiments 171-180, wherein the modified scrRNA comprises two to five phosphorothioate internucleoside linkages at the 3'-end of the scrRNA.

Embodiment 182. The compound of embodiment 171, wherein each internucleoside linkage of the scrRNA is a phosphorothioate internucleoside linkage.

Embodiment 183. The compound of any of embodiments 161-182, wherein the modified scrRNA does not comprise a 2'-deoxynucleoside.

Embodiment 184. The compound of any of embodiments 161-183, wherein at least one nucleoside of the modified scrRNA comprises a modified sugar moiety.

Embodiment 185. The compound of embodiment 184, wherein the 5'-terminal nucleoside of the scrRNA comprises a modified sugar moiety.

Embodiment 186. The compound of embodiment 185, wherein the 5'-terminal nucleoside comprises a non-bicyclic 2'-modified sugar moiety Embodiment 187. The compound of embodiment 185, wherein the 5'-terminal nucleoside comprises a bicyclic sugar moiety.

Embodiment 188. The compound of embodiment 185, wherein the 5'-terminal nucleoside comprises a modified sugar moiety selected from among: 2'-O-methyl, 2'-MOE, 2'-F, cEt, and LNA.

Embodiment 189. The compound of any of embodiments 184-188, wherein the internucleoside linkage at the 5'-end of the scrRNA is a phosphorothioate internucleoside linkage.

Embodiment 190. The compound of embodiment 184, wherein the modified scrRNA has the formula:

wherein:
each Ny is a nucleoside comprising a sugar moiety independently selected from among an unmodified 2'-deoxy sugar moiety, an unmodified 2'-hydroxy sugar moiety, a 2'-O-methyl modified sugar moiety, a 2'-F modified sugar moiety, and a cEt modified sugar moiety;
z is a neutral internucleoside linkage selected from among methoxypropyl phosphonate and methyl phosphonate;
s is a phosphorothioate internucleoside linkage; and
R is the remaining portion of the scrRNA.

Embodiment 191. The compound of embodiment 184, wherein the modified scrRNA has the formula:

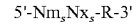

wherein:
Nm is a nucleoside comprising a 2'-O-methyl modified sugar moiety;
Nx is a nucleoside comprising a modified sugar moiety selected from among an unmodified 2'-hydroxy sugar moiety and a 2'-F modified sugar moiety;
s is a phosphorothioate internucleoside linkage; and
R is the remaining portion of the scrRNA.

Embodiment 192. The compound of any of embodiments 184-191, wherein the 3'-terminal nucleoside of the scrRNA comprises a modified sugar moiety.

Embodiment 193. The compound of embodiment 192, wherein the 3'-terminal internucleoside linkage of the scrRNA is a phosphorothioate internucleoside linkage.

Embodiment 194. The compound of embodiment 193, wherein the modified scrRNA has the formula:

5'-A-Nr$_s$Nr-3' wherein:
each Nr is a nucleoside comprising a modified sugar moiety independently selected from among: 2'-O-methyl, 2'-MOE, 2'-F, cEt, and LNA;
s is a phosphorothioate internucleoside linkage; and
A is the remaining portion of the scrRNA.

Embodiment 195. The compound of embodiment 192, wherein the modified scrRNA has the formula:

5'-A-Nr$_z$Nr-3' wherein:
each Nr is a nucleoside comprising a modified sugar moiety indepdently selected from among: 2'-O-methyl, 2'-MOE, 2'-F, cEt, and LNA;
z is a phosphate internucleoside linkage or a neutral internucleoside linkage selected from among methoxypropyl phosphonate and methyl phosphonate;
A is the remaining portion of the scrRNA;
provided that z is not a phosphate internucleoside linkage if the 3'-terminal Nr comprises a 2'-F sugar moiety.

Embodiment 196. The compound of any of embodiments 184-195, wherein the scrRNA target recognition portion of the modified scrRNA comprises at least 7 modified nucleosides, wherein the modified nucleosides each comprise a modified sugar moiety.

Embodiment 197. The compound of embodiment 196, wherein the seven 3'-terminal nucleosides comprise modified sugar moieties.

Embodiment 198. The compound of embodiment 196, wherein the ten 3'-terminal nucleosides comprise modified sugar moieties.

Embodiment 199. The compound of embodiment 197 or 198, wherein the modified sugar moieties of the 3'-terminal nucleosides are the same as one another.

Embodiment 200. The compound of embodiment 197 or 198, wherein the modified sugar moieties of the 3'-terminal nucleosides are each independently selected from among 2'-O-methyl and 2'-F.

Embodiment 201. The compound of embodiment 200, wherein the modified sugar moieties of the 3'-terminal nucleosides alternate between 2'-O-methyl and 2'-F.

Embodiment 202. The compound of any of embodiments 161-201, wherein the scrRNA target recognition portion of the scrRNA comprises at least one nucleoside comprising an unmodified sugar moiety.

Embodiment 203. The compound of any of embodiments 161-202, wherein the nuclease recognition portion of the modified scrRNA comprises at least 4 modified nucleosides, wherein the modified nucleosides each comprise a modified sugar moiety.

Embodiment 204. The compound of embodiment 203, wherein the four modified nucleosides of the nuclease recognition portion are the four 5'-terminal nucleosides of the scrRNA.

Embodiment 205. The compound of embodiment 203 or 204, wherein each of the modified sugar moieties of the nuclease recognition portion is the same as one another.

Embodiment 206. The compound of embodiment 205, wherein each modified sugar moiety of the nuclease recognition portion is a cEt or an LNA.

Embodiment 207. The compound of any of embodiments 203-205, wherein the at least four modified nucleosides each comprise a 2'-O-methyl modified sugar moiety.

Embodiment 208. The compound of any of embodiments 161-207, wherein the nuclease recognition portion of the scrRNA comprises at least one nucleoside comprising an unmodified sugar moiety.

Embodiment 209. The compound of any of embodiments 161-208, wherein the nuclease recognition portion comprises five modified nucleosides.

Embodiment 210. The compound of any of embodiments 161-208, wherein the nuclease recognition portion comprises six modified nucleosides.

Embodiment 211. The compound of any of embodiments 161-208, wherein the nuclease recognition portion comprises at least seven modified nucleosides.

Embodiment 212. The compound of any of embodiments 161-208, wherein the nuclease recognition portion comprises nine modified nucleosides.

Embodiment 213. The compound of any of embodiments 161-212, wherein at least one modified sugar moiety of the nuclease recognition portion is a bicyclic sugar moiety.

Embodiment 214. The compound of embodiment 213, wherein the two 5'-terminal nucleosides of the nuclease recognition portion comprise bicyclic sugar moieties.

Embodiment 215. The compound of embodiment 214, wherein the nuclease recognition portion comprises five bicyclic sugar moieties.

Embodiment 216. The compound of embodiment 214, wherein the nuclease recognition portion comprises six bicyclic sugar moieties.

Embodiment 217. The compound of embodiment 214, wherein the nuclease recognition portion comprises nine bicyclic sugar moieties.

Embodiment 218. The compound of any of embodiments 213-217, wherein each bicyclic sugar moiety is independently selected from among cEt and LNA.

Embodiment 219. The compound of embodiment 218, wherein each bicyclic sugar moiety is a cEt.

Embodiment 220. The compound of any of embodiments 161-219, wherein the scrRNA consists of 42 linked nucleosides.

Embodiment 221. The compound of any of embodiments 161-219, wherein the scrRNA consists of 20 to 42 linked nucleosides.

Embodiment 222. The compound of embodiment 221, wherein the scrRNA consists of 29 to 32 linked nucleosides.

Embodiment 223. The compound of embodiment 221, wherein the scrRNA consists of 32 linked nucleosides.

Embodiment 224. The compound of embodiment 221, wherein the scrRNA consists of 29 linked nucleosides.

Embodiment 225. The compound of embodiment 221, wherein the scrRNA consists of 20-28 linked nucleosides.

Embodiment 226. The compound of any of embodiments 161-225, wherein the nuclease recognition portion of the scrRNA consists of 17 or fewer linked nucleosides.

Embodiment 227. The compound of any of embodiments 161-226, wherein the scrRNA target recognition portion of the scrRNA consists of 17 or fewer linked nucleosides.

Embodiment 228. The compound of any of embodiments 161-227, wherein the compound consists of the scrRNA.

Embodiment 229. The compound of any of embodiments 161-227, wherein the compound comprises a conjugate group.

Embodiment 230. The compound of embodiment 229, wherein the conjugate group comprises GalNAc.

Embodiment 231. The compound of embodiment 229, wherein the conjugate group comprises a lipophilic group.

Embodiment 232. The compound of any of embodiments 161-231, wherein the nucleobase sequence of the scrRNA target recognition portion of the scrRNA is at least 90% complementary to a scrRNA target DNA.

Embodiment 233. The compound of embodiment 232, wherein the nucleobase sequence of the scrRNA target recognition portion of the scrRNA is 100% complementary to a scrRNA target DNA.

Embodiment 234. The compound of any of embodiments 161-233, wherein the scrRNA comprises a self-complementary region.

Embodiment 235. The compound of embodiment 234, wherein the self-complementary region is within the nuclease recognition portion of the scrRNA.

Embodiment 236. The compound of embodiment 234 or 235, wherein the self-complementary region can form a hairpin.

Embodiment 237. The compound of any of embodiments 234-236, wherein the self-complementary region of the scrRNA comprises at least one modification that increases the stability of the self-complementary region.

Embodiment 238. The compound of any of embodiments 234-237, wherein the self-complementary region of the scrRNA comprises at least one modification that increases the hybridization affinity of the self-complementary region.

Embodiment 239. A method comprising contacting a cell with the compound of any of embodiments 161-238.

Embodiment 240. The method of embodiment 239, wherein the cell expresses a Cpf1 nuclease.

Embodiment 241. A method comprising contacting a cell with the compound of any of embodiments 161-238 and a plasmid that encodes a nuclease gene.

Embodiment 242. A method comprising contacting a cell with the compound of any of embodiments 161-238 and an mRNA that encodes a nuclease.

Embodiment 243. The method of embodiment 241 or 242, wherein the nuclease is a Cpf1 nuclease.

Embodiment 244. The method of any of embodiments 239-243, wherein the scrRNA is taken up by the cell in the absence of a transfection reagent.

Embodiment 245. The method of any of embodiments 239-244, wherein the cell is in an animal Embodiment 246. A method comprising administering to an animal the modified compound of any of embodiments 161-238.

Embodiment 247. The method of embodiment 246, wherein the administration is subcutaneous.

Embodiment 248. The method of embodiment 246, wherein the administration is intrathecal.

Embodiment 249. The method of embodiment 246, wherein the administration is to the central nervous system.

Embodiment 250. The method of any of embodiments 246-249 comprising administering a plasmid that encodes a nuclease gene.

Embodiment 251. The method of any of embodiments 246-249 wherein the animal expresses a nuclease that is recognized by the nuclease recognition portion of the scrRNA.

Embodiment 252. The method of any of embodiments 246-249 comprising administering a plasmid that encodes a nuclease gene.

Embodiment 253. The method of embodiment 250 or 252, wherein the plasmid is delivered to cells within the animal via an adeno-associated virus (AAV).

Embodiment 254. The method of embodiment 250 or 252, wherein the plasmid is delivered to cells within the animal via a lentivirus.

Embodiment 255. The method of any of embodiments 250-254, wherein the nuclease is a Cpf1 nuclease.

Embodiment 256. The method of any of embodiments 239-255, wherein a scrRNA target gene is altered.

Embodiment 257. The method of embodiment 256, wherein the scrRNA is degraded after the scrRNA target gene is altered.

Embodiment 258. The method of embodiment 257, wherein the nuclease that is recognized by the nuclease recognition portion of the scrRNA does not exhibit nuclease activity in the absence of the scrRNA.

Embodiment 259. The method of any of embodiments 245-258, wherein the animal is a human.

Embodiment 260. A method comprising contacting a cell with the compound of any of embodiments 161-238, altering a scrRNA target gene, and contacting the cell with a second compound that degrades or inhibits the activity or expression of the scrRNA or a nuclease.

Embodiment 261. The method of embodiment 260, wherein the nuclease is a Cpf1 nuclease.

Embodiment 262. The method of embodiment 260 or 261, wherein the cell is contacted with the second compound after the scrRNA target gene has been altered.

Embodiment 263. The method of any of embodiments 260-262, wherein the second compound comprises an oligonucleotide that is complementary to the scrRNA.

Embodiment 264. The method of embodiment 263, wherein the scrRNA is degraded.

Embodiment 265. The method of any of embodiments 260-262, wherein the second compound comprises a scrRNA that targets the nuclease gene.

Embodiment 266. The method of any of embodiments 260-262, wherein the second compound comprises an oligonucleotide that is complementary to the nuclease transcript.

Embodiment 267. The method of embodiment 265 or 266, wherein the expression of the nuclease is inhibited.

Embodiment 268. The method of any of embodiments 260-267, wherein the cell is in an animal Embodiment 269. The method of embodiment 268, wherein the animal is a human Embodiment 270. A method of genomic loci visualization comprising contacting a genome with a compound of any of embodiments 161-238.

Embodiment 271. The method of any of embodiments 239-269, wherein alteration of off-target genes is reduced relative to alteration of off-target genes when unmodified scrRNA or a compound comprising more than 50 nucleosides is used in place of the compound comprising the modified scrRNA consisting of 20-50 linked nucleosides.

Embodiment 272. The compound of any of embodiments 1-57 or 81-122, wherein the sequence of the tracrRNA recognition portion of the crRNA comprises at least 12 contiguous nucleobases of a sequence selected from among SEQ ID Numbers 19, 20, 21, 22, 23, 24, and 25.

Embodiment 273. The compound of any of embodiments 1-57 or 81-122, wherein the sequence of the tracrRNA recognition portion of the crRNA comprises the first 12 nucleobases of a sequence selected from among SEQ ID Numbers 19, 20, 21, 22, 23, 24, and 25.

Embodiment 274. The compound of any of embodiments 1-57 or 81-122, wherein the sequence of the tracrRNA recognition portion of the crRNA consists of the first 12 nucleobases of a sequence selected from among SEQ ID Numbers 19, 20, 21, 22, 23, 24, and 25.

Embodiment 275. The compound of any of embodiments 162-238, wherein the sequence of the nuclease recognition portion of the scrRNA comprises the sequence UCUACU.

Embodiment 276. The compound of any of embodiments 162-238, wherein the sequence of the nuclease recognition portion of the scrRNA comprises the sequence GUAGAU.

Embodiment 277. The compound of any of embodiments 162-238, wherein the sequence of the nuclease recognition portion of the scrRNA comprises the sequence UCUACU and the sequence GUAGAU.

Embodiment 278. The compound of any of embodiments 162-238, wherein the sequence of the nuclease recognition portion of the scrRNA comprises at least 12 nucleobases of a sequence selected from among SEQ ID Numbers 26, 27, 28, 29, 30, 31, 32, 33, 34, 35, 36, 37, 38, and 39.

Embodiment 279. The compound of any of embodiments 1-57, 81-86, 88-122, 162-238, or 272-278, wherein the DNA recognition portion comprises 7-9 2'-modified sugar moieties.

Embodiment 280. The compound of embodiment 279, wherein the 7-9 2'-modified sugar moieties are 2'-F modified sugar moieties.

Embodiment 281. The compound of any of embodiments 279 or 280, wherein the tracrRNA recognition portion or the nuclease recognition portion comprises 5-6 bicyclic sugar moieties.

Embodiment 282. The compound of embodiment 281, wherein the 5-6 bicyclic sugar moieties are cEt.

Embodiment 283. A pharmaceutical composition comprising the compound of any of embodiments 1-57, 81-122, 162-238, or 272-283.

Embodiment 284. The method of any of embodiments 70, 131, or 246, wherein the administration is intravitreal.

Embodiment 285. The method of any of embodiments 58-68, 123-129, 144-152, 155-157, 239-244, or 260-267, wherein the cell is a plant cell.

Embodiment 286. The method of any of embodiments 58-68, 123-129, 144-152, 155-157, 239-244, or 260-267, wherein the cell is an animal cell.

Embodiment 287. The method of any of embodiments 58-68, 123-129, 144-152, 155-157, 239-244, or 260-267, wherein the cell is a T-cell.

Embodiment 288. A method of treating a disease in an individual comprising administering the compound of any of embodiments 1-57, 81-122, 162-238, or 272-282, or the composition of embodiment 283 to the individual, thereby treating the disease in the individual.

Embodiment 289. Use of the compound of any of embodiments 1-57, 81-122, 162-238, or 272-282 or the composition of embodiment 283 for the treatment of a disease.

Embodiment 290. Use of the compound of any of embodiments 1-57, 81-122, 162-238, or 272-282 for preparation of a medicament.

Embodiment 291. A method of administering the compound of any of embodiments 1-57, 81-122, 162-238, or 272-282 or the composition of embodiment 283 to an animal, and harvesting an organ from the animal for transplantation into a human.

BRIEF DESCRIPTION OF THE FIGURES

FIGS. 4a and 4b show that multiple truncated scrRNAs, including scrRNA containing only 36 nucleosides, altered the DNMT1 gene.

DETAILED DESCRIPTION

Figure 1:
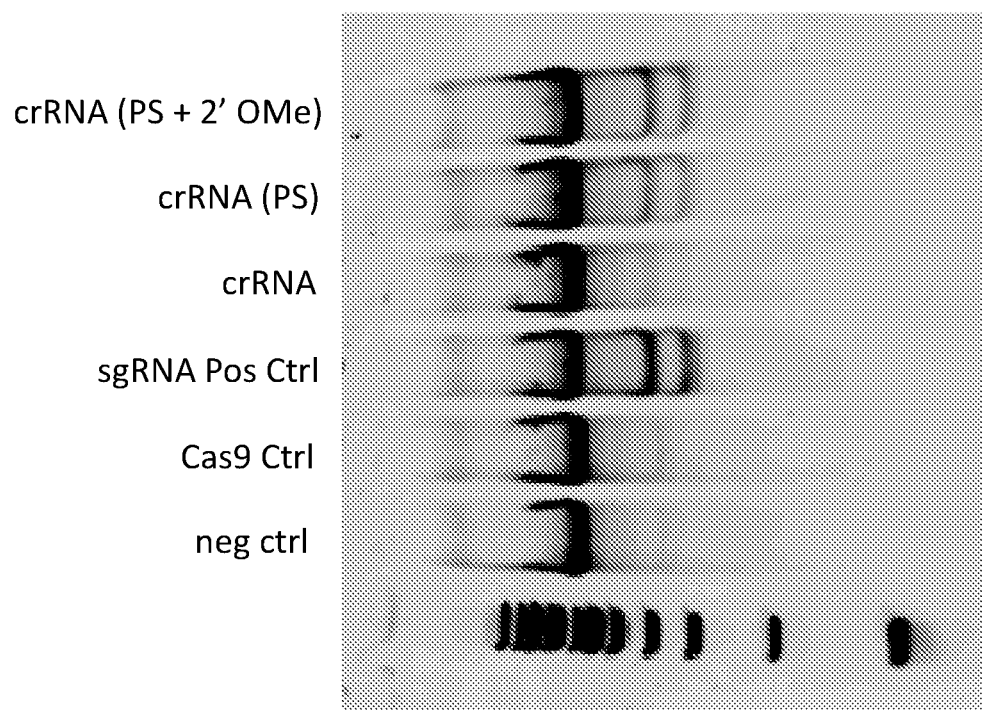
FIG. 1 is a gel illustrating the extent of gene editing of hLDLR.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Definitions

Unless otherwise indicated, the following terms have the following meanings:

As used herein, "2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (e.g., uracil).

As used herein, "2'-substituted nucleoside" or "2-modified nucleoside" means a nucleoside comprising a 2'-substituted or 2'-modified sugar moiety. As used herein, "2'-substituted" or "2-modified" in reference to a sugar moiety means a furanosyl sugar moiety comprising a 2'-substituent group other than H or OH.

As used here, "3'-stabilized" in reference to a modified oligonucleotide means a modified oligonucleotide comprising a modification or modifications at the 3'-terminus that increase the stability of the oligonucleotide in cells or in an animal relative to a corresponding oligonucleotide that does not comprise the modification or modifications at the 3'-terminus.

As used here, "5'-stabilized" in reference to a modified oligonucleotide means a modified oligonucleotide comprising a modification or modifications at the 5'-terminus that increase the stability of the oligonucleotide in cells or in an animal relative to a corresponding oligonucleotide that does not comprise the modification or modifications at the 5'-terminus.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "Cas9" means a nuclease that recognizes and/or cleaves target DNA when in a complex with crRNA and tracrRNA. In certain embodiments, Cas9 is derived from *S. pyogenes*. In certain embodiments, Cas9 is derived from *S. aureus*.

As used herein, "cell-targeting moiety" means a conjugate group or portion of a conjugate group that is capable of binding to a particular cell type or particular cell types.

As used herein, "complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside. In such embodiments, mismatches are not tolerated.

As used herein, "conjugate group" means a group of atoms that is directly or indirectly attached to a parent compound, e.g., an oligonucleotide.

As used herein, "conjugate linker" means a group of atoms that connects a conjugate group to a parent compound, e.g., an oligonucleotide.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other As used herein, "crRNA" means an oligonucleotide or portion of an oligonucleotide that comprises a DNA recognition portion and a tracrRNA recognition portion. As used herein, "DNA recognition portion" is nucleobase sequence that is complementary to a DNA target. As used herein, "tracrRNA recognition portion" is a nucleobase sequence that is bound to or is capable of binding to tracrRNA. The tracRNA recognition portion of crRNA may bind to tracrRNA via hybridization or covalent attachment.

As used herein, "fully modified" in reference to an oligonucleotide means a modified oligonucleotide in which each sugar moiety is modified. "Uniformly modified" in reference to an oligonucleotide means a fully modified oligonucleotide in which each at least one modification of each sugar moiety is the same. For example, the nucleosides of a uniformly modified oligonucleotide can each have a 2'-MOE modification but different nucleobase modifications, and the internucleoside linkages may be different.

As used herein, "gene editing" means any process mediated by a Cas9/crRNA/tracrRNA or Cas9/sgRNA complex, including but not limited to gene knock-down, gene knock-out, gene disruption, deletion, insertion, and gene activation. As used herein, "gene alteration" means any process mediated by a nuclease/scrRNA containing complex, including but not limited to gene knock-down, gene disruption, deletion, insertion, and gene activation.

As used herein, "gRNA" comprises both a crRNA and a tracrRNA. In certain embodiments, the crRNA and tracrRNA of a gRNA are distinct molecules. In certain embodiments, the crRNA and tracrRNA of a gRNA are portions of one oligonucleotide, wherein the oligonucleotide is referred to as a "sgRNA".

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "increases", when used in reference to an effect mediated by a modified oligonucleotide, means that the effect is greater in the presence of the oligonucleotide containing a certain modification than the effect is in the presence of a corresponding oligonucleotide that does not contain the certain modification.

As used herein, the terms "internucleoside linkage" means a group that forms a covalent linkage between adjacent nucleosides in an oligonucleotide. As used herein "modified internucleoside linkage" means any internucleoside linkage other than a naturally occurring, phosphate internucleoside linkage. Naturally occurring, non-phosphate linkages are referred to herein as modified internucleoside linkages. "Phosphorothioate linkage" means a linkage between nucleosides wherein the phosphodiester bond of a phosphate linkage is modified by replacing one of the non-bridging oxygen atoms with a sulfur atom. A phosphorothioate linkage is a modified internucleoside linkage.

As used herein, "linearly modified sugar" or "linearly modified sugar moiety" means a modified sugar moiety that comprises an acyclic or non-bridging modification. Such linear modifications are distinct from bicyclic sugar modifications.

As used herein, "linked nucleosides" are nucleosides that are connected in a continuous sequence (i.e. no additional nucleosides are present between those that are linked). Linked nucleosides may or may not be linked by internucleoside linkages.

As used herein, "mismatch" or means a nucleobase of a first oligonucleotide that is not capable of pairing with the corresponding nucleobase of a second oligonucleotide or target nucleic acid when the first and second oligomeric compound are aligned.

As used herein, "MOE" means methoxyethyl. "2'-MOE" means a —OCH$_2$CH$_2$OCH$_3$ group at the 2' position of a furanosyl ring.

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means a heterocyclic moiety capable of pairing with a second, different nucleobase. As used herein, "nucleobase sequence" means the order of contiguous nucleobases independent of any sugar or internucleoside linkage modification. As used herein, "modified nucleobase" means a nucleobase other than adenine (A), thymine (T), cytosine (C), uracil (U), and guanine (G), herein defined as the five, unmodified nucleobases. A universal base is a nucleobase that can pair with any one of the five unmodified nucleobases.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an crRNA compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in an inactive form that is converted to an active form within the body or cells thereof by the action of endogenous enzymes or other chemicals and/or physiologic conditions.

As used herein, "scrRNA" or "single crRNA" means an oligonucleotide that comprises a scrRNA target recognition portion and a nuclease recognition portion and does not comprise a tracrRNA recognition portion or a tracrRNA. In certain embodiments, scrRNAs comprise a self-complementary region. In certain such embodiments, the nuclease recognition portion partially or completely overlaps with the self-complementary region. As used herein, "scrRNA target recognition portion" is a portion of an oligonucleotide with a nucleobase sequence that is complementary to a scrRNA DNA target. As used herein, "nuclease recognition portion" is a portion of an oligonucleotide that can bind to, associate with, or contribute to the binding to or association with a nuclease that is not a Cas9 nuclease. In certain embodiments, the nuclease recognition portion of an oligonucleotide binds to or associates with a Cpf1 nuclease.

As used herein, "self-complementary" in reference to an oligonucleotide means an oligonucleotide that is at least partially complementary to itself. In certain embodiments, a self-complementary oligonucleotide forms a hairpin when a portion of the self-complementary oligonucleotide hybridizes to itself.

As used herein, "sugar moiety" means a group of atoms that can link a nucleobase to another group, such as an internucleoside linkage, conjugate group, or terminal group. In certain embodiments, a sugar moiety is attached to a nucleobase to form a nucleoside. As used herein, "unmodified sugar moiety" means a 2'-OH(H) furanosyl moiety, as found in RNA, or a 2'-H(H) moiety, as found in DNA. Unmodified sugar moieties have one hydrogen at each of the 1', 3', and 4' positions, an oxygen at the 3' position, and two hydrogens at the 5' position. As used herein, "modified sugar moiety" or "modified sugar" means a sugar surrogate or a furanosyl moiety comprising a non-hydrogen substituent in place of at least one hydrogen of an unmodified sugar moiety. In certain embodiments, a modified sugar moiety is a 2'-substituted sugar moiety. Such modified sugar moieties include bicyclic sugars and linearly modified sugars.

As used herein, "sugar surrogate" means a modified sugar moiety having other than a furanosyl moiety that can link a nucleobase to another group, such as an internucleoside linkage, conjugate group, or terminal group. Modified nucleosides comprising sugar surrogates can be incorporated into one or more positions within an oligonucleotide. In certain embodiments, such oligonucleotides are capable of hybridizing to complementary oligomeric compounds or nucleic acids.

As used herein, "target nucleic acid," "target DNA," "target gene" and "nucleic acid target" mean a nucleic acid that a crRNA is designed to affect. As used herein, "scrRNA target nucleic acid," "scrRNA target DNA," "scrRNA target gene" and "scrRNA nucleic acid target" mean a nucleic acid that a scrRNA is designed to affect. An "off-target gene" is a gene that a crRNA or a scrRNA is not designed to affect. In certain embodiments, the editing or alteration of an off-target gene is deleterious.

As used herein, "terminal group" means a chemical group or group of atoms that is covalently linked to a terminus of an oligonucleotide.

As used herein, "tracrRNA" means an oligonucleotide or portion of an oligonucleotide that can non-covalently bind to a Cas9 protein and that can bind to a crRNA via hybridization or covalent attachment.

Certain Oligonucleotides for Use in a CRISPR System

I. Certain CRISPR RNA (crRNA)

In certain embodiments, the present invention provides modified oligonucleotides for use in CRISPR. Typically, CRISPR employs CRSPR RNA (crRNA), which hybridizes to target DNA and also hybridizes to trans-activating RNA (tracrRNA), which in turn recruits a nuclease, cas9, which cleaves the target DNA. Thus, the crRNA in such systems has two functions: (1) recognition and hybridization to the target DNA and (2) recognition and hybridization to the tracrRNA. Typically, in such systems, the crRNA has two portions which correspond to these two functions: a DNA recognition portion and a tracrRNA recognition portion. The present invention provides modified oligonulcleotides that may be used in crRNA. Such modified oligonucleotides may have modifications in the DNA recognition portion and/or tracrRNA recognition portion.

In certain embodiments, the tracrRNA recognition portion of the crRNA comprises a portion of the direct repeat sequence from a bacterial species that has a Type II CRISPR system. In certain such embodiments, the tracrRNA recognition portion of the crRNA comprises a sequence selected from the table below. In certain embodiments, the tracrRNA recognition portion of the crRNA comprises the first 12 nucleobases of a sequence selected from the table below. In certain embodiments, the tracrRNA recognition portion of the crRNA comprises the first 13, 14, 15, 16, 17, 18, 19, 20, 21, or 22 nucleobases of a sequence selected from the table below. In certain embodiments, the sequence of the tracrRNA recognition portion of the crRNA consists of the first 12 nucleobases of a sequence selected from the table below. In certain embodiments, the sequence of the tracrRNA recognition portion of the crRNA consists of the first 13, 14, 15, 16, 17, 18, 19, 20, 21, or 22 nucleobases of a sequence selected from the table below.

TABLE A

Direct repeat sequences used in tracrRNA recognition portions of crRNA

| Species | Sequence | SEQ ID NO. |
|---|---|---|
| S. pyogenes | GUUUUAGAGCUAUGCUGUUUUG | 19 |
| S. aureus | GUUUUAGUACUCUGUAAUUUUA | 20 |
| S. thermophiles | GUUUUUGUACUCUCAAGAUUUA | 21 |
| S. pasteurianus | GUUUUUGUACUCUCAAGAUUUA | 21 |
| N. cinerea | GUUGUAGCUCCCAUUCUCAUUU | 22 |
| C. lar | GUUUUAGUCUCUUUUUAAAUUU | 23 |
| P. lavamentivoran | GCUGCGGAUUGCGGCCGUCUCU | 24 |
| C. diptheriae | ACUGGGGUUCAGUUCUCAAAAA | 25 |

In certain instances, the crRNA and tracrRNA are joined to one another to form a single molecule referred to as a single guide RNA (sgRNA). In certain embodiments, the present invention provides modified oligonucleotides for use in sgRNA.

II. Certain Single CRISPR RNA (scrRNA)

In certain alternative embodiments, the present invention provides modified oligonucleotides for use in a CRISPR system that employs scrRNA, which hybridizes to a scrRNA target DNA and participates in recruitment of a nuclease other than Cas9. In certain such embodiments, the nuclease is a Cpf1 nuclease or a variant thereof. The nuclease (e.g., the Cpf1 nuclease) cleaves the scrRNA target DNA. Thus, the scrRNA in such systems has two functions: (1) recognition and hybridization to the scrRNA target DNA and (2) recognition and recruitment of the nuclease. Typically, in such systems, the scrRNA has two portions which correspond to these two functions: a scrRNA target recognition portion and a nuclease recognition portion. The present invention provides modified oligonucleotides that may be used in scrRNA. Such modified oligonucleotides may have modifications in the scrRNA target recognition portion and/or nuclease recognition portion. In certain embodiments, the nuclease recognition portion is 5' to the scrRNA target recognition portion. In certain embodiments, the nuclease recognition portion is 3' to the scrRNA target recognition portion.

In certain embodiments, the nuclease recognition portion of the scrRNA comprises a portion of the direct repeat sequence from a bacterial organism that has a Cpf1 nuclease or a Cpf1 ortholog. In certain such embodiments, the nuclease recognition portion of the scrRNA comprises a sequence selected from the table below. In certain embodiments, the nuclease recognition portion of the scrRNA comprises 12 nucleobases of a sequence selected from the table below. In certain embodiments, the tracrRNA recognition portion of the crRNA comprises 13, 14, 15, 16, 17, 18, or 19 nucleobases of a sequence selected from the table below. In certain embodiments, the sequence of the nuclease recognition portion of the scrRNA consists of 12 nucleobases of a sequence selected from the table below. In certain embodiments, the sequence of the nuclease recognition portion of the scrRNA consists of 13, 14, 15, 16, 17, 18, 19, 20, or 21 nucleobases of a sequence selected from the table below. In certain embodiments, the nuclease recognition portion of the scrRNA comprises the sequence UCUACU and GUAGAU.

TABLE B

Direct repeat sequences used in nuclease recognition portions of scrRNA

| Organism | Sequence | SEQ ID NO. |
|---|---|---|
| Francisella novicida | UAAUUUCUACUGUUGUAGAU | 26 |
| Lachnospimceae bacterium MC2017 | AGAAAUGCAUGGUUCUCAUGC | 27 |
| Butyrivibrio proteoclasticus | AAAAUUACCUAGUAAUUAGGU | 28 |
| Peregrinibacteria bacterium | GGAUUUCUACUUUUGUAGAU | 29 |
| Parcubacteria bacterium | AAAUUUCUACUUUUGUAGAU | 30 |
| Smithella | GUUUCAAUCCACGCGCCCACG CGGGGCGCGAC | 31 |
| Acidaminococcus | UAAUUUCUACUCUUGUAGAU | 32 |
| Lachnospiraceae bacterium MA2020 | GAAUUUCUACUAUUGUAGAU | 33 |
| Candidatus Methanoplasma termitum | GAAUCUCUACUCUUUGUAGAU | 34 |
| Eubacterium eligens | UAAUUUCUACUUUGUAGAU | 35 |
| Moraxella bovoculi | AAAUUUCUACUGUUUGUAGAU | 36 |
| Leptospim inadai | GAAUUUCUACUUUUGUAGAU | 37 |
| Lachnospimceae bacterium ND2006 | UAAUUUCUACUAAGUGUAGAU | 38 |

TABLE B-continued

Direct repeat sequences used in nuclease
recognition portions of scRNA

| Organism | Sequence | SEQ ID NO. |
|---|---|---|
| Polphyromonas crevioricanis | UAAUUUCUACUAUUGUAGAU | 39 |
| Prevotella disiens | UAAUUUCUACUUCGGUAGAU | 40 |
| Polphyromonas macacae | UAAUUUCUACUAUUGUAGAU | 39 |

Certain Oligonucleotides for Use as crRNA

In certain embodiments, modified crRNA comprise a modified oligonucleotide. In certain embodiments, modified crRNA consist of a modified oligonucleotide. Modified oligonucleotides described herein are suitable for use as crRNA.

Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

In certain embodiments, such modified oligonucleotides may contain any combination of the modified sugar moieites, modified nucleobases, modified internucleoside linkages, motifs, and/or lengths described herein.

Certain Oligonucleotides for Use as scrRNA

In certain embodiments, modified scrRNA comprise a modified oligonucleotide. In certain embodiments, modified scrRNA consist of a modified oligonucleotide. Modified oligonucleotides described herein are suitable for use as scrRNA.

Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

In certain embodiments, such modified oligonucleotides may contain any combination of the modified sugar moieites, modified nucleobases, modified internucleoside linkages, motifs, and/or lengths described herein.

Certain Methods of Use Comprising Modified crRNA

In certain embodiments, methods comprising contacting a cell with a compound comprising a modified crRNA are in vitro methods. In certain embodiments, methods comprising contacting a cell with a compound comprising a modified crRNA are ex vivo methods. In certain embodiments, methods comprising contacting a cell with a compound comprising a modified crRNA are in vivo methods.

Various Cas9 variants, both naturally occurring and genetically engineered, can be used in the methods of the present invention. Such Cas9 variants include but are not limited to inactive Cas9 mutants that are used in applications that do not require target nucleic acid cleavage, such as gene activation, and truncated Cas9 variants that are suitable for expression in certain vectors, such as AAV vectors.

In certain embodiments, methods comprising contacting a cell with a compound comprising a modified crRNA further comprise contacting the cell with a second compound to inhibit (or turn off) the CRISPR system after the target gene is edited.

In certain embodiments, gene editing methods comprising contacting a cell with a compound comprising a modified crRNA produce fewer and/or less deleterious off-target effects than gene editing methods that use of an unmodified crRNA in place of the modified crRNAs of the invention.

Certain Methods of Use Comprising Modified scrRNA

In certain embodiments, methods comprising contacting a cell with a compound comprising a modified scrRNA are in vitro methods. In certain embodiments, methods comprising contacting a cell with a compound comprising a modified scrRNA are ex vivo methods. In certain embodiments, methods comprising contacting a cell with a compound comprising a modified scrRNA are in vivo methods.

Various nuclease variants, both naturally occurring and genetically engineered, can be used in the methods of the present invention. Such nuclease variants include but are not limited to inactive nuclease mutants that are used in applications that do not require scrRNA target nucleic acid cleavage, such as gene activation, and truncated nuclease variants that are suitable for expression in certain vectors, such as AAV vectors.

In certain embodiments, methods comprising contacting a cell with a compound comprising a modified scrRNA further comprise contacting the cell with a second compound to inhibit (or turn off) the CRISPR system after the scrRNA target gene is altered.

In certain embodiments, gene altering methods comprising contacting a cell with a compound comprising a modified scrRNA produce fewer and/or less deleterious off-target effects than gene altering methods that use an unmodified scrRNA in place of the modified scrRNAs of the invention.

A. Certain Modified Nucleosides

Certain compounds of the present invention incorporate modified nucleosides. Unless otherwise provided, the following modified nucleosides, without limitation, are suitable for such incorporation into modifed oligonucleotides for use as crRNA or scrRNA. In certain embodiments, modified oligonucleotides comprise at least one modified nucleoside. Such modified nucleosides comprise a modified sugar moiety or a modified nucleobase or both a modifed sugar moiety and a modified nucleobase.

1. Certain Sugar Moieties

In certain embodiments, modified oligonucleotides, such as modified crRNAs or modified scrRNAs, comprise one or more modified nucleosides comprising a modified sugar moiety. Such modified oligonucleotides comprising one or more sugar-modified nucleosides may have desirable properties, such as enhanced nuclease stability or increased binding affinity with a target nucleic acid relative to oligonucleotides lacking such sugar-modified nucleosides. In certain embodiments, modified sugar moieties are linearly modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are linearly modified sugar moieties comprising a furanosyl ring with one or more acyclic substituent, including but not limited to substituents at the 2' and/or 5' positions. Examples of 2'-substituent groups suitable for linearly modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 5'-substituent groups suitable for linearly modified sugar moieties include but are not limited to: 5'-methyl (R or S), 5'-vinyl, and 5'-methoxy. In certain embodiments, linearly modified sugars comprise more than one non-bridging sugar substituent, for example, 2'-F-5'-methyl sugar moieties (see, e.g., PCT International Application WO 2008/101157, for additional 2', 5'-bis substituted sugar moieties and nucleosides).

In certain embodiments, a 2'-substituted nucleoside or 2'-linearly modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-linearly modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON (CH$_3$)$_2$, O(CH$_2$)$_2$O(CH$_2$)$_2$N(CH$_3$)$_2$, and OCH$_2$C(=O)—N (H)CH$_3$ ("NMA").

In certain embodiments, a 2'-substituted nucleoside or 2'-linearly modified nucleoside comprises a sugar moiety comprising a linear 2'-substituent group selected from: F, OCH$_3$, and OCH$_2$CH$_2$OCH$_3$.

Nucleosides comprising modified sugar moieties, such as linearly modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., U.S. Pat. No. 7,399,845), 4'-C(CH$_3$)(CH$_3$)—O-2' and analogs thereof (see, e.g., WO2009/006478), 4'-CH$_2$—N(OCH$_3$)-2' and analogs thereof (see, e.g., WO2008/150729), 4'-CH$_2$—O—N(CH$_3$)-2' (see, e.g., US2004/0171570), 4'-CH$_2$—C(H)(CH$_3$)-2' (see, e.g., Chattopadhyaya, et al., J. Org. Chem., 2009, 74, 118-134), 4'-CH$_2$—C(=CH$_2$)-2' and analogs thereof (see, published PCT International Application WO 2008/154401), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 20017, 129, 8362-8379; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056, 564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, an LNA nucleoside (described above) may be in the α-L configuration or in the β-D configuration.

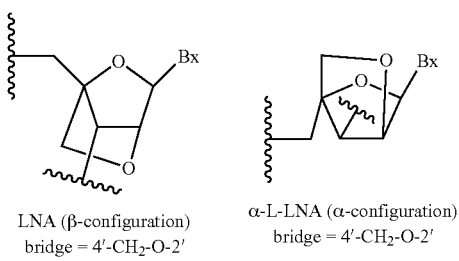

LNA (β-configuration)
bridge = 4'-CH₂-O-2'

α-L-LNA (α-configuration)
bridge = 4'-CH₂-O-2'

α-L-methyleneoxy (4'-CH₂—O-2') or α-L-LNA bicyclic nucleosides have been incorporated into oligonucleotides (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the R-D configuration, unless otherwise specified.

In certain embodiments, modified sugar moieties comprise one or more non-bridging sugar substituent and one or more bridging sugar substituent (e.g., 5'-substituted and 4'-2' bridged sugars). (see, e.g., WO 2007/134181, wherein LNA nucleosides are further substituted with, for example, a 5'-methyl or a 5'-vinyl group, and see, e.g., U.S. Pat. Nos. 7,547,684; 7,750,131; 8,030,467; 8,268,980; 7,666, 854; and 8,088,746).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described above. For example, certain sugar surrogates comprise a 4'-sulfur atom and a substitution at the 2'-position (see, e.g., US2005/0130923) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see Leumann, C J. *Bioorg. & Med. Chem.* 2002, 10, 841-854), fluoro HNA:

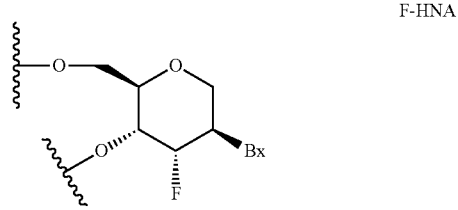

F-HNA ("F-HNA", see e.g., U.S. Pat. Nos. 8,088,904; 8,440,803; and 8,796,437, F-HNA can also be referred to as a F-THP or 3'-fluoro tetrahydropyran), and nucleosides comprising additional modified THP compounds having the formula:

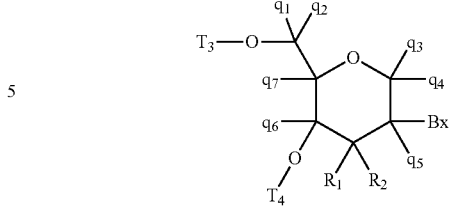

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $g_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)$ $NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $g_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and U.S. Pat. Nos. 5,698,685; 5,166,315; 5,185, 444; and 5,034,506). As used here, the term "morpholino" means a sugar surrogate having the following structure:

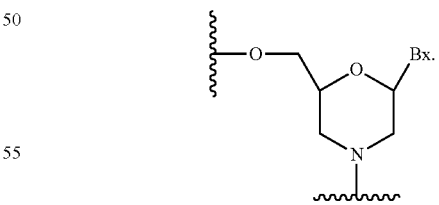

In certain embodiments, morpholinos may be modified, for example by adding or altering various substituent groups from the above morpholino structure. Such sugar surrogates are refered to herein as "modifed morpholinos."

In certain embodiments, sugar surrogates comprise acyclic moieites. Examples of nucleosides and oligonucleotieds comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in WO2011/133876.

Many other bicyclic and tricyclic sugar and sugar surrogate ring systems are known in the art that can be used in modified nucleosides (see, e.g., Leumann, J. C, *Bioorganic & Medicinal Chemistry*, 2002, 10, 841-854).

2. Certain Modified Nucleobases

In certain embodiments, modified oligonucleotides, such as modified crRNAs or modified scrRNAs, comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Representative United States patents that teach the preparation of certain of the above noted modified nucleobases as well as other modified nucleobases include without limitation, US2003/0158403, U.S. Pat. Nos. 3,687,808; 4,845, 205; 5,130,302; 5,134,066; 5,175,273; 5,367,066; 5,432, 272; 5,434,257; 5,457,187; 5,459,255; 5,484,908; 5,502, 177; 5,525,711; 5,552,540; 5,587,469; 5,594,121; 5,596, 091; 5,614,617; 5,645,985; 5,681,941; 5,750,692; 5,763, 588; 5,830,653 and 6,005,096.

B. Certain Modified Internucleoside Linkages

In certain embodiments, nucleosides of modified oligonucleotides, such as modified crRNAs or modified scrRNAs, may be linked together using any internucleoside linkage. The two main classes of internucleoside linking groups are defined by the presence or absence of a phosphorus atom.

Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester (—O—C(=O)—S—), thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

1. Certain Modification Motifs

In certain embodiments, the crRNA has a modification motif selected from the table below.

TABLE C

| crRNA modification motifs | |
| --- | --- |
| 29-mers | 42-mers |
| f$_7$r$_6$kr$_3$kr$_3$kr$_3$krk$_2$ | f$_{10}$r$_{18}$kr$_4$kr$_2$kr$_3$k$_2$ |
| mf$_6$r$_6$kr$_3$kr$_3$kr$_3$krk$_2$ | mf$_9$r$_{18}$kr$_4$kr$_2$kr$_3$k$_2$ |
| mf$_6$r$_{10}$k$_6$r$_2$k$_4$ | mr$_{27}$kr$_4$kr$_2$kr$_3$k$_2$ |
| mr$_{16}$k$_6$r$_2$k$_4$ | mr$_9$f$_{10}$k$_6$r$_2$kr$_4$kr$_2$kr$_3$k$_2$ |
| mr$_6$f$_{10}$k$_6$r$_2$k$_4$ | mr$_9$f$_{10}$l$_6$r$_2$kr$_4$kr$_2$kr$_3$k$_2$ |
| mf$_6$r$_{10}$f$_6$r$_2$k$_4$ | mr$_9$f$_{16}$r$_2$kr$_4$kr$_2$kr$_3$k$_2$ |
| mf$_6$r$_{10}$l$_6$r$_2$k$_4$ | mr$_{32}$kr$_2$kr$_3$k$_2$ |
| mr$_6$f$_{10}$l$_6$r$_2$k$_4$ | ef$_9$r$_{18}$kr$_4$kr$_2$kr$_3$k$_2$ |
| mf$_6$r$_{10}$l$_6$r$_2$l$_4$ | r(MOP)f$_9$r$_{18}$kr$_4$kr$_2$kr$_3$k$_2$ |
| mr$_{16}$k$_6$r$_2$l$_4$ | d(MOP)f$_9$r$_{18}$kr$_4$kr$_2$kr$_3$k$_2$ |
| mr$_6$f$_{10}$k$_6$r$_2$l$_4$ | f(MOP)f$_9$r$_{18}$kr$_4$kr$_2$kr$_3$k$_2$ |
| mf$_6$r$_{10}$f$_6$r$_2$l$_4$ | r(MP)f$_9$r$_{18}$kr$_4$kr$_2$kr$_3$k$_2$ |
| r(MOP)f$_6$r$_6$kr$_3$kr$_3$kr$_3$krk$_2$ | d(MP)f$_9$r$_{18}$kr$_4$kr$_2$kr$_3$k$_2$ |
| d(MOP)f$_6$r$_6$kr$_3$kr$_3$kr$_3$krk$_2$ | f(MP)f$_9$r$_{18}$kr$_4$kr$_2$kr$_3$k$_2$ |
| f(MOP)f$_6$r$_6$kr$_3$kr$_3$kr$_3$krk$_2$ | r(MMI)f$_9$r$_{18}$kr$_4$kr$_2$kr$_3$k$_2$ |
| r(MP)f$_6$r$_6$kr$_3$kr$_3$kr$_3$krk$_2$ | d(MMI)f$_9$r$_{18}$kr$_4$kr$_2$kr$_3$k$_2$ |
| d(MP)f$_6$r$_6$kr$_3$kr$_3$kr$_3$krk$_2$ | f(MMI)f$_9$r$_{18}$kr$_4$kr$_2$kr$_3$k$_2$ |
| f(MP)f$_6$r$_6$kr$_3$kr$_3$kr$_3$krk$_2$ | mr$_{32}$k$_2$k(G-Clamp)r$_2$k$_2$ |
| r(MOP)f$_6$r$_{10}$k$_6$r$_2$k$_4$ | mr$_{27}$k$_3$r$_2$kr$_2$kr$_3$k$_2$ |
| d(MOP)f$_6$r$_{10}$k$_6$r$_2$k$_4$ | mf$_9$r$_{18}$k$_3$r$_2$kr$_2$kr$_3$k$_2$ |
| f(MOP)f$_6$r$_{10}$k$_6$r$_2$k$_4$ | mf$_6$r$_{11}$(5-Propyne-U)$_4$r$_3$k$_3$r$_2$kr$_2$kr$_3$k$_2$ |
| r(MP)f$_6$r$_{10}$k$_6$r$_2$k$_4$ | 29-mers |
| r(MP)f$_6$r$_{10}$k$_6$r$_2$k$_4$ | d(MOP)r$_6$f$_{10}$k$_6$r$_2$k$_4$ |
| r(MP)f$_6$r$_{10}$k$_6$r$_2$k$_4$ | f(MOP)r$_6$f$_{10}$k$_6$r$_2$k$_4$ |
| r(MOP)r$_{16}$k$_6$r$_2$k$_4$ | r(MP)r$_6$f$_{10}$k$_6$r$_2$k$_4$ |

TABLE C-continued crRNA modification motifs

| | |
|---|---|
| $d(MOP)r_1_6k_6r_2k_4$ | $d(MOP)r_6f_{10}k_6r_2k_4$ |
| $f(MOP)r_{16}k_6r_2k_4$ | $f(MOP)r_6f_{10}k_6r_2k_4$ |
| $r(MP)r_{16}k_6r_2k_4$ | $r(MOP)f_6r_{10}l_6r_2k_4$ |
| $d(MP)r_{16}k_6r_2k_4$ | $d(MOP)f_6r_{10}l_6r_2k_4$ |
| $f(MP)r_{16}k_6r_2k_4$ | $f(MOP)f_6r_{10}l_6r_2k_4$ |
| $r(MOP)r_6f_{10}k_6r_2k_4$ | $r(MOP)f_6r_{10}l_6r_2k_4$ |
| $d(MP)f_6r_{10}k_6r_2l_4$ | $d(MOP)f_6r_{10}f_6r_2l_4$ |
| $f(MP)f_6r_{10}k_6r_2l_4$ | $f(MOP)f_6r_{10}f_6r_2l_4$ |
| $r(MOP)r_{16}k_6r_2l_4$ | $f_7r_6kr_3kr_3kr_3k(G\text{-}Clamp)k_2$ |
| $d(MOP)r_{16}k_6r_2l_4$ | $mf_6r_6kr_3kr_3k(G\text{-}Clamp)rk_2$ |
| $f(MOP)r_{16}k_6r_2l_4$ | $mf_6r_{10}k_6r_2k(G\text{-}Clamp)k_2$ |
| $r(MP)r_{16}k_6r_2l_4$ | $mr_{16}k_6r_2k(G\text{-}Clam)k_2$ |
| $d(MP)r_{16}k_6r_2l_4$ | $mr_6f_{10}k_6r_2k(G\text{-}Clamp)k_2$ |
| $f(MP)r_{16}k_6r_2l_4$ | $mf_6r_{10}f_6r_2k(G\text{-}Clamp)k_2$ |
| $r(MOP)r_6f_{10}k_6r_2l_4$ | $mf_6r_{10}l_6r_2k(G\text{-}Clamp)k_2$ |
| $r(MOP)r_6f_{10}k_6r_2l_4$ | $mr_6f_{10}l_6r_2k(G\text{-}Clamp)k_2$ |
| $r(MOP)r_6f_{10}k_6r_2l_4$ | $mf_6r_{10}k_6r_2l(G\text{-}Clamp)l_2$ |
| $r(MOP)r_6f_{10}k_6r_2l_4$ | $mr_{16}k_6r_2l(G\text{-}Clamp)l_2$ |
| $r(MOP)r_6f_{10}k_6r_2l_4$ | $mr_6f_{10}k_6r_2l(G\text{-}Clamp)l_2$ |
| $r(MOP)r_6f_{10}k_6r_2l_4$ | $mf_6r_{10}f_6r_2l(G\text{-}Clamp)l_2$ |
| $r(MOP)f_6r_{10}f_6r_2l_4$ | $f_7r_6kr_3k(5\text{-}propyne)r_3kr_3krk_2$ |
| $d(MOP)f_6r_{10}f_6r_2l_4$ | $mf_6r_6kr_3k(5\text{-}Propyne)r_3kr_3krk_2$ |
| $f(MOP)f_6r_{10}f_6r_2l_4$ | $r(MOP)f_6r_{10}f_6r_2l_4$ |

Table C Legend: "mn" indicates a 2'-O-methyl modified nucleoside, "f" indicates a 2'-F modified nucleoside, "r" indicates an unmodified 2'-hydroxy sugar containing nucleoside, "d" indicates an unmodified 2'-deoxy sugar containing nucleoside, "e" indicates a 2'-MOE modified nucleoside, "k" indicates a cEt bicyclic sugar containing nucleoside, and "l" indicates an LNA bicyclic sugar containing nucleoside. The modifications listed in parentheses are optional modified nucleobases or optional modified internucleoside linkages: "(G-Clamp)" indicates a G-Clamp modified nucleobase that is part of the nucleoside represented by the letter immediately preceding it. "(5-Propyne)" indicates a 5'-propynyl modified nucleobase that is part of the nucleoside represented by the letter immediately preceding it. "(MOP)" indicates a methoxypropyl modified internucleoside linkage, "(MP)" indicates a methylphosphonate internucleoside linkage, and "(MMI)" indicates an MMI N-methyl internucleoside linkage. In certain embodiments, crRNAs having a motif with a parenthetical modification listed in the table above include the indicated parenthetical modification. In certain embodiments, the parenthetical modification of crRNAs having a motif with a parenthetical modification listed in the table above is replaced with a different modified or unmodified nucleobase or internucleoside linkage. The number subscripts in the table above indicate the number of contiguous nucleosides that comprise the identified modification. The lack of a number subscript indicates one nucleoside. The motifs listed in the table above may be used with any crRNA nucleobase sequence and with any internucleoside linkage motif. In certain embodiments, all of the nucleobases are unmodified. In certain embodiments, at least one nucleobase is a 5-methylcytosine modified nucleobase. In certain embodiments, the internucleoside linkages are all selected independently from among phosphate and phosphorothioate. In certain embodiments, one or more internucleoside linkages is a neutral internucleoside linkage.

C. Certain Conjugate Groups and Terminal Groups

In certain embodiments, oligonucleotides for use as crRNA or scrRNA further comprise conjugate groups and/or terminal groups. In certain embodiments, compounds comprising oligonucleotides for use as crRNA or scrRNA further comprise a conjugate group or terminal group. In certain such embodiments, oligonucleotides are covalently attached to one or more conjugate group. In certain embodiments, conjugate groups modify one or more properties of the attached oligonucleotide, including but not limited to pharmacodynamics, pharmacokinetics, stability, binding, absorption, cellular distribution, cellular uptake, charge and clearance. In certain embodiments, conjugate groups impart a new property on the attached oligonucleotide, e.g., fluorophores or reporter groups that enable detection of the oligonucleotide. Conjugate groups and/or terminal groups may be added to oligonucleotides having any of the modifications or motifs described above.

Conjugate groups include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Lett., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), an octadecylamine or hexylamino-carbonyl-oxycholesterol moiety (Crooke et al., J. Pharmacol. Exp. Ther., 1996, 277, 923-937), a tocopherol group (Nishina et al., Molecular Therapy Nucleic Acids, 2015, 4, e220; doi:10.1038/mtna.2014.72 and Nishina et al., Molecular Therapy, 2008, 16, 734-740), or a GalNAc cluster (e.g., WO2014/179620).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Conjugate groups are attached directly or via an optional conjugate linker to a parent compound, such as a crRNA or scrRNA oligonucleotide. In certain embodiments, conjugate groups are directly attached to oligonucleotides. In certain embodiments, conjugate groups are indirectly attached to oligonucleotides via conjugate linkers. In certain embodiments, the conjugate linker comprises a chain structure, such as a hydrocarbyl chain, or an oligomer of repeating units such as ethylene glycol or amino acid units. In certain embodiments, conjugate groups comprise a cleavable moiety. In certain embodiments, conjugate groups are attached to oligonucleotides via a cleavable moiety. In certain embodiments, conjugate linkers comprise a cleavable moiety. In certain such embodiments, conjugate linkers are attached to oligonucleotides via a cleavable moiety. In certain embodiments, oligonucleotides comprise a cleavable moiety, wherein the cleavable moiety is a nucleoside is attached to a cleavable internucleoside linkage, such as a phosphate internucleoside linkage. In certain embodiments, a conjugate group comprises a nucleoside or oligonucleotide, wherein the nucleoside or oligonucleotide of the conjugate group is indirectly attached to a parent oligonucleotide.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the crRNA oligonucleotides provided herein and the scrRNA oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, a cleavable moiety is a cleavable bond. In certain embodiments, a cleavable moiety comprises a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate linker or conjugate group.

In certain embodiments, a cleavable moiety is a nucleoside. In certain such embodiments, the unmodified or modified nucleoside comprises an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, a cleavable moiety is 2'-deoxy nucleoside that is attached to either the 3' or 5'-terminal nucleoside of an oligonucleotide by a phosphate internucleoside linkage and covalently attached to the conjugate linker or conjugate group by a phosphate or phosphorothioate linkage. In certain such embodiments, the cleavable moiety is 2'-deoxyadenosine.

Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

In certain embodiments, a conjugate group is a cell-targeting moiety. In certain embodiments, a conjugate group, optional conjugate linker, and optional cleavable moiety have the general formula:

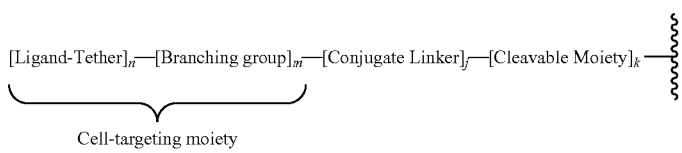

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactoseamine (GalNAc), mannose, glucose, glucoseamine and fucose. In certain embodiments, each ligand is N-acetyl galactoseamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

Certain Pharmaceutical Compositions

In certain embodiments, the present invention provides pharmaceutical compositions comprising one or more crRNA. In certain embodiments, such pharmaceutical composition comprises a tracrRNA. In certain embodiments, the pharmaceutical composition comprises a means of expressing Cas9. In certain embodiments, such means of expressing Cas9 is a plasmid or a viral vector. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, the present invention provides pharmaceutical compositions comprising one or more scrRNA. In certain embodiments, the pharmaceutical composition comprises a means of expressing a nuclease. In certain embodiments, such means of expressing the nuclease is a plasmid or a viral vector. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

NONLIMITING DISCLOSURE AND INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^m$CGAUCG," wherein $^m$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated. As a further example, the motifs of crRNA described herein can also be applied to scrRNAs. In particular, motifs of the DNA recognition portions of the crRNAs described herein may be applied to the scrRNA target recognition portions of scrRNAs. Similarly, motifs of the tracrRNA recognition portions of the crRNAs described herein may be applied to the nuclease recognition portions of scrRNAs.

Example 1: Gene Editing Effects of Modified crRNA on the hLDLR Locus

Modified crRNAs comprising a DNA recognition portion that is complementary to hLDLR were designed and synthesized to test their effects on gene editing of the human LDLR locus. HEK 293T cells were transfected with a plasmid expressing Cas9 protein and tracrRNA using Lipofectamine 3000 (Life Technologies). Alternatively, cells were transfected with a plasmid expressing Cas9 protein and a highly active sgRNA as a positive control or no Cas9 ("Cas9 Ctrl") as a negative control. Six hours later, cells were washed one time with PBS and transfected with a crRNA described in the table below using RNAiMAX (Life Technologies) or with no crRNA as a control ("neg ctrl"). 48 hours following the second transfection, genomic DNA was isolated from cells and used in a SURVEYOR assay (Integrated DNA Technologies) according to the manufacturer's directions. The PCR primers used to amplify the crRNA target site were forward: 5'-GGAGACCCAAATA-CAACAAATC-3' (SEQ ID NO: 1) and reverse: 5'-CTA-GACTCCGTCTCAAAGAAG-3' (SEQ ID NO: 2). Following Cell cleavage, the DNA was run on a gel to analyze the extent of gene editing of hLDLR (see FIG. 1). Quantification was performed using Image J software, and the indel incidence percentage was calculated using the following formula: indel (%)=100×(1−(1−fraction cut of target gene)$^{0.5}$), wherein the fraction cut of target gene was determined by dividing the fluorescent signal of the cut target gene fragment(s) by the total fluorescent signal of the cut and intact target gene fragment(s). The indel incidence for each modified crRNA was normalized to the indel incidence of the positive control sgRNA, referred to as the gene disruption percentage. The results, shown in the table below, indicate that the phosphorothioate modified crRNA was more active than the unmodified crRNA, and the phosphorothioate and 2'-O-methyl modified crRNA was even more active than the crRNA that does not comprise sugar modifications.

TABLE 1 crRNA targeting hLDLR

| Name | Sequence (5' to 3') | Gene disruption, normalized to sgRNA (%) | SEQ ID NO. |
|---|---|---|---|
| crRNA | GCGCCTTGCTCCTCGCCGCGGGUUUU AGAUCUAUGCUGUUUUG | 7 | 5 |
| PS crRNA | G$_s$C$_s$G$_s$C$_s$C$_s$T$_s$T$_s$G$_s$C$_s$T$_s$C$_s$C$_s$T$_s$C$_s$G$_s$C$_s$ C$_s$G$_s$C$_s$G$_s$G$_s$U$_s$U$_s$U$_s$U$_s$A$_s$G$_s$A$_s$U$_s$C$_s$U$_s$A$_s$ U$_s$G$_s$C$_s$U$_s$G$_s$U$_s$U$_s$U$_s$U$_s$G | 33 | 5 |
| PS 2'-OMe crRNA | G$_m$C$_{ms}$G$_{ms}$C$_{ms}$C$_{ms}$T$_s$T$_s$G$_s$C$_s$T$_s$C$_s$C$_s$T$_s$C$_s$ G$_s$C$_s$C$_s$G$_s$C$_s$G$_s$G$_s$U$_s$U$_s$U$_s$U$_s$A$_s$G$_s$A$_s$U$_s$C$_s$ U$_s$A$_s$U$_s$G$_s$C$_s$U$_s$G$_s$U$_{ms}$U$_{ms}$U$_{ms}$U$_{ms}$G$_m$ | 47 | 5 |

Subscripts: "m" indicates a 2'-O-methyl modification, "s" indicates a phosphorothioate internucleoside linkage. The underlined nucleosides represent the DNA recognition portion of the crRNA, the nucleosides that are not underlined represent the tracrRNA recognition portion of the crRNA.

Example 2: Gene Editing Effects of Modified crRNA on the hVEGFA Locus

Figure 2:
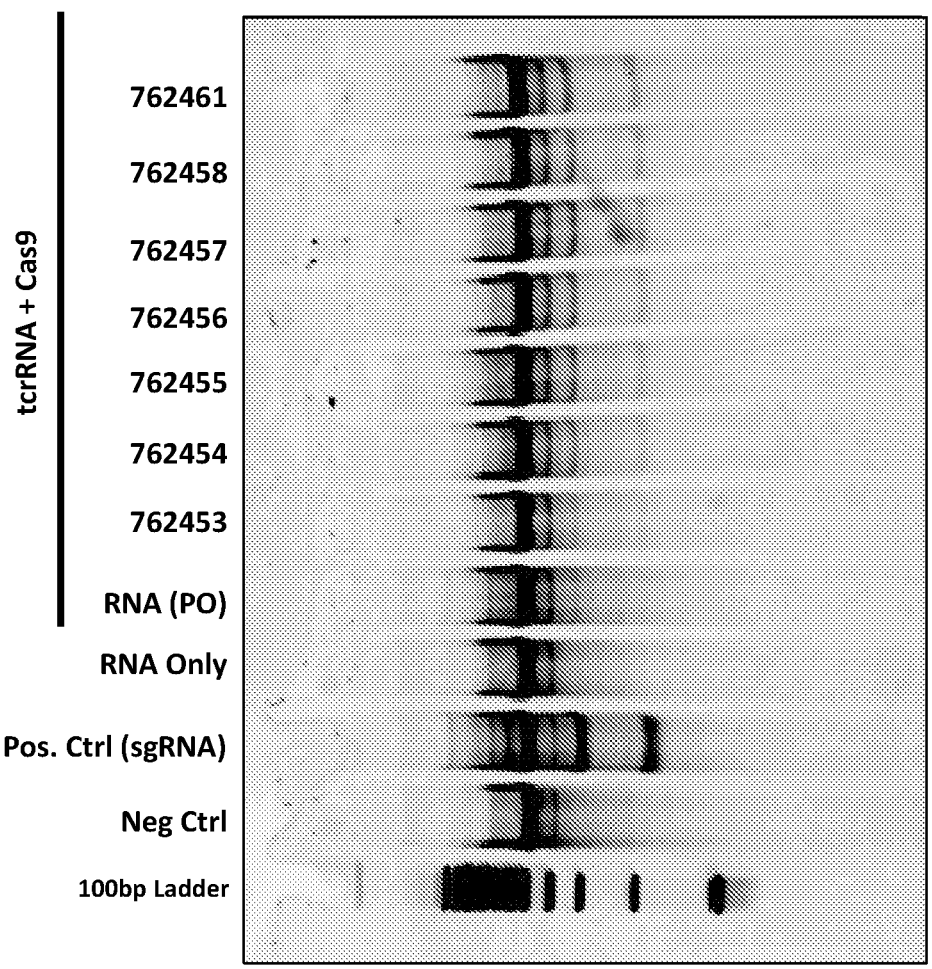
FIG. 2 is a gel illustrating the extent of gene editing of hVEGFA.

Modified crRNAs comprising a DNA recognition portion that is complementary to hVEGFA were designed and synthesized to test their effects on gene editing of the human VEGFA locus. HEK 293T cells were transfected as described in Example 1 using a crRNA described in the table below. The SURVEYOR assay was performed as described in Example 1, and the PCR primers used to amplify the crRNA target site were forward: 5'-TCCAGATGGCACAT-TGTCAG-3' (SEQ ID NO: 3) and reverse: 5'-AGG-GAGCAGGAAAGTGAGGT-3' (SEQ ID NO: 4). Following Cell cleavage, the DNA was run on a gel to analyze the extent of gene editing of hVEGFA (see FIG. 2), and the gel was quantified as described in Example 1. The results for the modified crRNAs were normalized to a positive control sgRNA targeted to hVEGFA to determine the gene disruption percentage shown in the table below. The results indicate that many of the modified crRNAs were active.

TABLE 2 crRNA targeting hVEGFA

| Isis No. | Sequence (5' to 3') | Gene disruption, normalized to sgRNA (%) | SEQ ID NO. |
|---|---|---|---|
| 762453 | $G_{fs}$ $G_{rs}$ $U_{fs}$ $G_{rs}$ $A_{fs}$ $G_{rs}$ $U_{fs}$ $G_{rs}$ $A_{fs}$ $G_{rs}$ $U_{fs}$ $G_{rs}$ $U_{fs}$ $G_{rs}$ $U_{fs}$ $G_{rs}$ $C_{fs}$ $G_{rs}$ $U_{fs}$ $G_{rs}$ $G_{rs}$ <u>$U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $U_{rs}$ $G_r$</u> | <1 | 6 |
| 762454 | $G_{fs}$ $G_{fs}$ $U_{fs}$ $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{rs}$ <u>$U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $U_{rs}$ $G_r$</u> | 14 | 6 |
| 762455 | $G_{rs}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{rs}$ <u>$U_{fs}$ $U_{rs}$ $U_{rs}$ $U_{rs}$ $A_{rs}$ $G_{rs}$ $A_{rs}$ $G_{rs}$ $C_{fs}$ $U_{rs}$ $A_{fs}$ $U_{rs}$ $G_{fs}$ $C_{rs}$ $U_{fs}$ $G_{rs}$ $U_{fs}$ $U_{rs}$ $U_{fs}$ $U_{rs}$ $G_f$</u> | 18 | 6 |
| 762456 | $G_{fs}$ $G_{rs}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ <u>$G_{rs}$ $U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $U_{rs}$ $G_r$</u> | 19 | 7 |
| 762457 | $G_{rs}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{rs}$ <u>$U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $U_{rs}$ $G_f$</u> | 29 | 6 |
| 762458 | $G_{fs}$ $G_{rs}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ <u>$G_{rs}$ $U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $U_{rs}$ $G_f$</u> | 18 | 7 |
| 762461 | $G_{ms}$ $G_{rs}$ $U_{rs}$ $G_{rs}$ $A_{ms}$ $G_{rs}$ $U_{rs}$ $G_{rs}$ $A_{ms}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{rs}$ <u>$U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $U_{rs}$ $G_d$</u> | 40 | 6 |

Subscripts: "m" indicates a 2'-O-methyl modification, "s" indicates a phosphorothioate internucleoside linkage, "f" indicates a 2'-F modification, "r" indicates an unmodified 2' hydroxy sugar moiety, and "d" indicates an unmodified 2'-deoxy sugar moiety. The underlined nucleosides represent the DNA recognition portion of the crRNA, the nucleosides that are not underlined represent the tracrRNA recognition portion of the crRNA.

Example 3: Gene Editing Effects of Modified crRNA on the hVEGFA Locus

Figure 3:
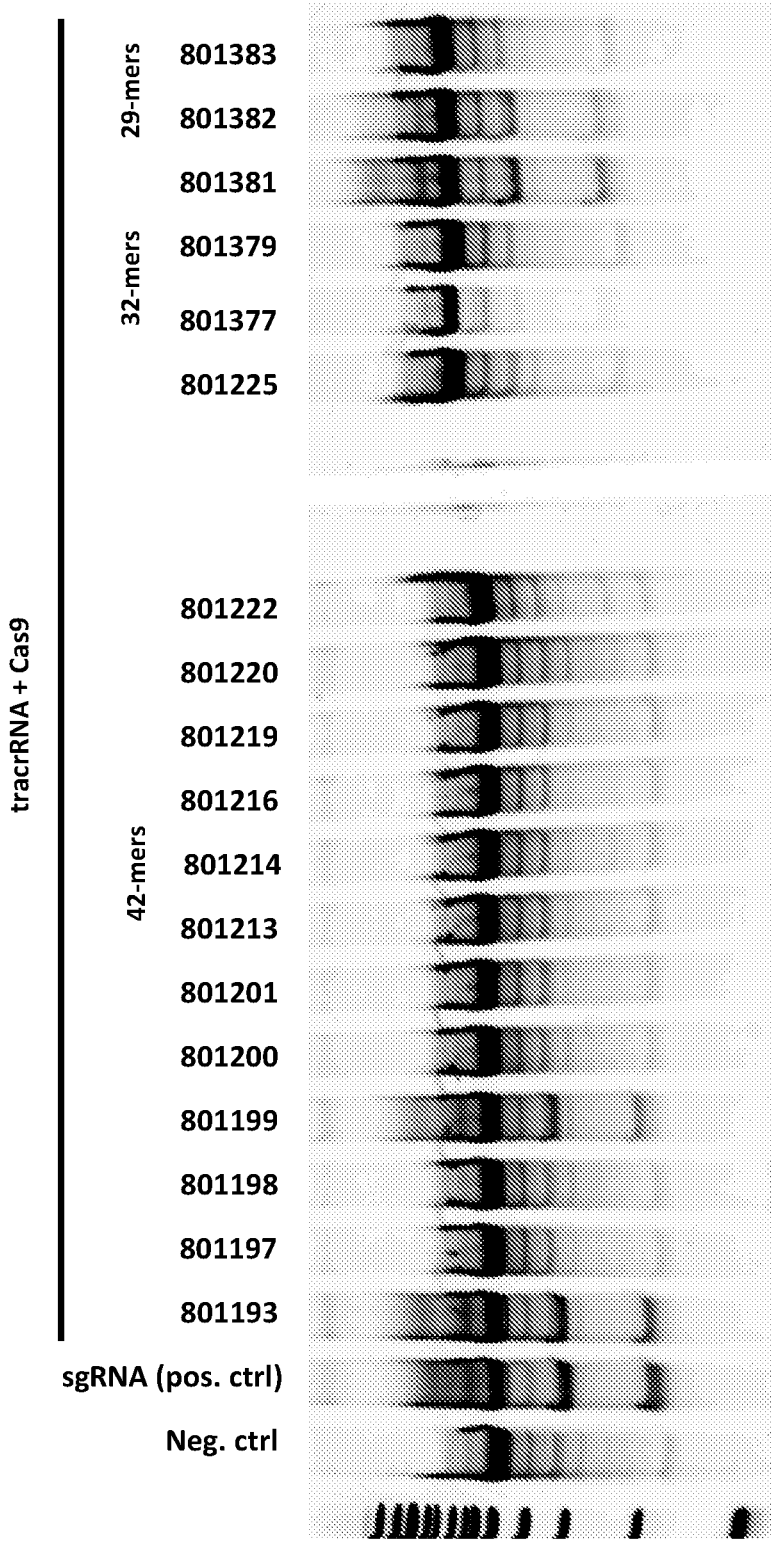
FIG. 3 is a gel illustrating the extent of gene editing of hVEGFA using crRNAs, including shortened modified crRNAs.

Modified crRNAs comprising a DNA recognition portion that is complementary to hVEGFA were designed and synthesized to test their effects on gene editing of the human VEGFA locus. HEK 293T cells were transfected as described in Example 1 using a crRNA described in the table below, and the Cas9/tracrRNA load time was 24 hours. The SURVEYOR assay was performed as described in Example 1, and the PCR primers used to amplify the crRNA target site were forward: 5'-TCCAGATGGCACATTGTCAG-3' (SEQ ID NO: 3) and reverse: 5'-AGGGAGCAGGAAAGT-GAGGT-3' (SEQ ID NO: 4). Following Cell cleavage, the DNA was run on a gel to analyze the extent of gene editing of hVEGFA (see FIG. 3), and the gel was quantified as described in Example 1. The results for the modified crRNAs were normalized to a positive control sgRNA targeted to hVEGFA to determine the gene disruption percentage shown in the table below. The results indicate that many of the modified crRNAs were active or very active.

TABLE 3 crRNA targeting hVEGFA

| Isis No. | Sequence (5' to 3') | Gene disruption, normalized to sgRNA (%) | SEQ ID NO. |
|---|---|---|---|
| 801193 | $G_{fs}$ $G_{fs}$ $U_{fs}$ $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{rs}$ $U_{rs}$ <u>$U_{rs}$ $U_{rs}$ $U_{rs}$ $A_{rs}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$</u> | 75 | 8 |
| 801197 | $G_{fs}$ $G_{fs}$ $U_{fs}$ $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{ks}$ $U_{rs}$ $G_{ks}$ $C_{rs}$ $G_{rs}$ $U_{rs}$ $G_{rs}$ $G_{ks}$ $U_{rs}$ <u>$U_{rs}$ $U_{rs}$ $U_{rs}$ $A_{ks}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$</u> | <1 | 8 |
| 801198 | $G_{ks}$ $G_{fs}$ $U_{fs}$ $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{ks}$ $U_{rs}$ $G_{ks}$ $C_{rs}$ $U_{rs}$ $G_{rs}$ $G_{ks}$ <u>$U_{rs}$ $U_{rs}$ $U_{rs}$ $U_{rs}$ $A_{ks}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$</u> | <1 | 8 |
| 801199 | $G_{ms}$ $G_{fs}$ $U_{ms}$ $G_{fs}$ $A_{ms}$ $G_{fs}$ $U_{ms}$ $G_{fs}$ $A_{ms}$ $G_{fs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{rs}$ <u>$U_{rs}$ $U_{rs}$ $U_{rs}$ $U_{rs}$ $A_{rs}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$</u> | 65 | 8 |
| 801200 | $G_{ms}$ $G_{fs}$ $U_{ms}$ $G_{fs}$ $A_{ms}$ $G_{fs}$ $U_{ms}$ $G_{fs}$ $A_{ms}$ $G_{fs}$ $U_{rs}$ $G_{rs}$ $U_{rs}$ $G_{ks}$ $U_{rs}$ $G_{ks}$ $C_{rs}$ $G_{rs}$ $U_{rs}$ $G_{rs}$ $G_{ks}$ <u>$U_{rs}$ $U_{rs}$ $U_{rs}$ $U_{rs}$ $A_{ks}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$</u> | <1 | 8 |
| 801201 | $G_{ks}$ $G_{fs}$ $U_{ms}$ $G_{fs}$ $A_{ms}$ $G_{fs}$ $U_{ms}$ $G_{fs}$ $A_{ms}$ $G_{fs}$ $U_{rs}$ $G_{rs}$ $U_{rs}$ $G_{ks}$ $U_{rs}$ $G_{ks}$ $C_{rs}$ $G_{rs}$ $U_{rs}$ $G_{rs}$ $G_{ks}$ <u>$U_{rs}$ $U_{rs}$ $U_{rs}$ $U_{rs}$ $A_{ks}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$</u> | <1 | 8 |
| 801213 | $G_{ms}$ $G_{fs}$ $U_{ms}$ $G_{fs}$ $A_{ms}$ $G_{fs}$ $U_{ms}$ $G_{fs}$ $A_{ms}$ $G_{fs}$ $U_{ms}$ $G_{fs}$ $U_{ms}$ $G_{fs}$ $U_{ms}$ $G_{fs}$ $C_{ms}$ $G_{fs}$ $U_{ms}$ $G_{fs}$ <u>$G_{ms}$ $U_{fs}$ $U_{ms}$ $U_{fs}$ $U_{ms}$ $A_{fs}$ $G_{ms}$ $A_{fs}$ $G_{ms}$ $C_{fs}$ $U_{ms}$ $A_{fs}$ $U_{ms}$ $G_{fs}$ $C_{ms}$ $U_{fs}$ $G_{ms}$ $U_{fs}$ $U_{ms}$ $U_{fs}$ $U_{ms}$ $G_m$</u> | <1 | 6 |

TABLE 3-continued crRNA targeting hVEGFA

| Isis No. | Sequence (5' to 3') | Gene disruption, normalized to sgRNA (%) | SEQ ID NO. |
|---|---|---|---|
| 801214 | $G_{ms}$ $G_{fs}$ $U_{mo}$ $G_{fs}$ $A_{mo}$ $G_{fs}$ $U_{mo}$ $G_{fs}$ $A_{mo}$ $G_{fs}$ $U_{mo}$ $G_{fs}$ $U_{mo}$ $G_{fs}$ $U_{mo}$ $G_{fs}$ $C_{mo}$ $G_{fs}$ $U_{mo}$ $G_{fs}$ $G_{mo}$ $U_{fs}$ $U_{mo}$ $U_{fs}$ $U_{mo}$ $A_{fs}$ $G_{mo}$ $A_{fs}$ $G_{mo}$ $C_{fs}$ $U_{mo}$ $A_{fs}$ $U_{mo}$ $G_{fs}$ $C_{mo}$ $U_{fs}$ $G_{mo}$ $U_{fs}$ $U_{ms}$ $U_{fs}$ $U_{ms}$ $G_m$ | <1 | 6 |
| 801216 | $G_{ks}$ $G_{ds}$ $T_{ds}$ $G_{ds}$ $A_{ks}$ $G_{ds}$ $T_{ds}$ $G_{ds}$ $A_{ds}$ $G_{ks}$ $T_{ds}$ $G_{ds}$ $T_{ds}$ $G_{ks}$ $T_{ds}$ $G_{ds}$ $C_{ds}$ $G_{ds}$ $T_{ds}$ $G_{ks}$ $G_{ds}$ $T_{ds}$ $T_{ds}$ $T_{ds}$ $T_{ds}$ $A_{ks}$ $G_{ds}$ $A_{ds}$ $G_{ks}$ $C_{ds}$ $T_{ds}$ $A_{ks}$ $T_{ds}$ $G_{ds}$ $C_{ds}$ $T_{ks}$ $G_{ds}$ $T_{ds}$ $T_{ds}$ $T_{ds}$ $T_{ks}$ $G_k$ | <1 | 9 |
| 801219 | $G_{ms}$ $G_{ms}$ $U_{ms}$ $G_{ds}$ $A_{ds}$ $G_{ds}$ $U_{ms}$ $G_{ms}$ $A_{ms}$ $G_{ds}$ $T_{ds}$ $G_{ds}$ $U_{ms}$ $G_{ms}$ $U_{ms}$ $G_{ms}$ $C_{ds}$ $G_{ds}$ $T_{ds}$ $G_{ms}$ $G_{ms}$ $U_{ms}$ $U_{ms}$ $T_{ds}$ $T_{ds}$ $A_{ds}$ $G_{ms}$ $A_{ms}$ $G_{ms}$ $C_{ds}$ $T_{ds}$ $A_{ds}$ $U_{ms}$ $G_{ms}$ $C_{ms}$ $T_{ds}$ $G_{ds}$ $T_{ds}$ $U_{ms}$ $U_{ms}$ $U_{ms}$ $G_m$ | <1 | 10 |
| 801220 | $G_{es}$ $G_{es}$ $T_{es}$ $G_{ds}$ $A_{ds}$ $G_{ds}$ $T_{es}$ $G_{es}$ $A_{es}$ $G_{ds}$ $T_{ds}$ $G_{ds}$ $T_{es}$ $G_{es}$ $T_{es}$ $G_{es}$ $C_{ds}$ $G_{es}$ $T_{es}$ $G_{es}$ $G_{es}$ $T_{es}$ $T_{es}$ $T_{ds}$ $T_{ds}$ $A_{ds}$ $G_{es}$ $A_{es}$ $G_{es}$ $C_{ds}$ $T_{ds}$ $A_{ds}$ $T_{es}$ $G_{es}$ $^mC_{es}$ $T_{ds}$ $G_{ds}$ $T_{ds}$ $T_{es}$ $T_{es}$ $T_{es}$ $G_e$ | <1 | 9 |
| 801222 | $G_{ms}$ $G_{ms}$ $U_{ms}$ $G_{fs}$ $A_{fs}$ $G_{fs}$ $U_{ms}$ $G_{ms}$ $A_{ms}$ $G_{fs}$ $U_{fs}$ $G_{fs}$ $U_{ms}$ $G_{ms}$ $U_{ms}$ $G_{ms}$ $C_{fs}$ $G_{fs}$ $U_{fs}$ $G_{ms}$ $G_{ms}$ $U_{ms}$ $U_{ms}$ $U_{fs}$ $U_{fs}$ $A_{fs}$ $G_{ms}$ $A_{ms}$ $G_{ms}$ $C_{fs}$ $U_{fs}$ $A_{fs}$ $U_{ms}$ $G_{ms}$ $C_{ms}$ $U_{fs}$ $G_{fs}$ $U_{fs}$ $U_{ms}$ $U_{ms}$ $U_{ms}$ $G_m$ | <1 | 6 |
| 801225 | $G_{ks}$ $G_{ds}$ $T_{ds}$ $G_{ds}$ $A_{ks}$ $G_{ds}$ $T_{ds}$ $G_{ds}$ $A_{ks}$ $G_{ds}$ $T_{ds}$ $G_{ks}$ $T_{ds}$ $G_{ds}$ $T_{ds}$ $G_{ks}$ $C_{ds}$ $G_{ds}$ $T_{ds}$ $G_{ks}$ $G_{ds}$ $T_{ds}$ $T_{ds}$ $T_{ks}$ $T_{ds}$ $A_{ds}$ $G_{ds}$ $A_{ks}$ $G_{ks}$ $C_{ds}$ $T_{ds}$ $A_{ks}$ $T_{ds}$ $G_{ds}$ $C_{ds}$ $T_{ks}$ $G_{ds}$ $T_{ds}$ $T_{ds}$ $T_{ks}$ $T_{ks}$ $G_k$ | <1 | 9 |

Subscripts: "m" indicates a 2'-O-methyl modification, "s" indicates a phosphorothioate internucleoside linkage, "f" indicates a 2'-F modification, "r" indicates an unmodified 2'-hydroxy sugar moiety, "d" indicates an unmodified 2'-deoxy sugar moiety, "e" indicates a 2'-MOE modification, "o" indicates a phosphate internucleoside linkage, and "k" indicates a cEt modification. Superscript "m" indicates a 5-methyl modification of the nucleobase. The underlined nucleosides represent the DNA recognition portion of the crRNA, the nucleosides that are not underlined represent the tracrNA recognition portion of the crRNA.

Example 4: Gene Editing Effects of Modified, Shortened crRNA on the hVEGFA Locus VEGFA targeting, modified crRNAs comprising a DNA recognition portion that is under 20 nucleosides in length and/or a tracrRNA recognition portion that is under 22 nucleosides in length were designed and synthesized to test their effects on gene editing of the human VEGFA locus. HEK 293T cells were transfected as described in Example 1 using a crRNA described in the table below. The SURVEYOR assay was performed as described in Example 1, and the PCR primers used to amplify the crRNA target site were forward: 5'-TCCAGATGGCACATTGTCAG-3' (SEQ ID NO: 3) and reverse: 5'-AGGGAGCAGGAAAGT-GAGGT-3' (SEQ ID NO: 4). Following Cell cleavage, the DNA was run on a gel to analyze the extent of gene editing of hVEGFA (see FIG. 3). The experiment was repeated, and the resulting gel was quantified as described in Example 1. The results for the modified crRNAs were normalized to a positive control sgRNA targeted to hVEGFA to determine the gene disruption percentage shown in the table below. The results indicate that many of the shortened, modified crRNAs were active, including crRNAs that comprise only a 12 nucleoside tracrRNA recognition portion and only a 17 nucleoside DNA recognition portion.

TABLE 4 crRNA targeting hVEGFA

| Isis No. | Sequence (5' to 3') | Gene disruption, normalized to sgRNA (%) | SEQ ID NO. |
|---|---|---|---|
| 801377 | $G_{fs}$ $G_{fs}$ $U_{fs}$ $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $^mC_{ks}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | 42 | 11 |
| 801379 | $G_{ms}$ $G_{fs}$ $U_{ms}$ $G_{fs}$ $A_{ms}$ $G_{fs}$ $U_{ms}$ $G_{fs}$ $A_{ms}$ $G_{fs}$ $U_{ms}$ $G_{fs}$ $U_{ms}$ $G_{fs}$ $U_{ms}$ $G_{fs}$ $C_{ms}$ $G_{fs}$ $U_{ms}$ $G_{fs}$ $G_{ms}$ $U_{fs}$ $U_{ms}$ $U_{fs}$ $U_{ms}$ $A_{fs}$ $G_{ms}$ $A_{fs}$ $G_{ms}$ $C_{fs}$ $U_{ms}$ $A_m$ | <1 | 12 |
| 801381 | $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $^mC_{ks}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | 42 | 13 |
| 801382 | $G_{ms}$ $A_{fs}$ $G_{ms}$ $U_{fs}$ $G_{ms}$ $A_{fs}$ $G_{ms}$ $U_{rs}$ $G_{rs}$ $U_{rs}$ $G_{rs}$ $U_{rs}$ $G_{rs}$ $^mC_{ks}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | 64 | 13 |
| 801383 | $G_{ms}$ $A_{fs}$ $G_{ms}$ $U_{fs}$ $G_{ms}$ $A_{fs}$ $G_{ms}$ $U_{fs}$ $G_{ms}$ $U_{fs}$ $G_{ms}$ $U_{fs}$ $G_{ms}$ $C_{fs}$ $G_{ms}$ $U_{fs}$ $G_{ms}$ $G_{fs}$ $U_{ms}$ $U_{fs}$ $U_{ms}$ $U_{fs}$ $A_{ms}$ $G_{fs}$ $A_{ms}$ $G_{fs}$ $C_{ms}$ $U_{fs}$ $A_m$ | <1 | 14 |

Subscripts: "m" indicates a 2'-O-methyl modification, "s" indicates a phosphorothioate internucleoside linkage, "f" indicates a 2'-F modification, "r" indicates an unmodified 2'-hydroxy sugar moiety, "d" indicates an unmodified 2'-deoxy sugar moiety, and "k" indicates a cEt modification. Superscript "m" indicates a 5-methyl modification of the nucleobase. The underlined nucleosides represent the DNA recognition portion of the crRNA, the nucleosides that are not underlined represent the tracrRNA recognition portion of the crRNA.

Example 5: crRNA Modification Motifs

Modified crRNAs having the motifs described in the table below can be used for any crRNA nucleobase sequence. The first 17 to 20 nucleosides of each motif represent the DNA recognition portion of the crRNA, and the remaining 12 to 22 nucleosides of each motif represent the tracrRNA recognition portion of the crRNA. The motifs labeled "29-mers" contain 29 linked nucleosides, and the motifs labeled "42-mers" contain 42 linked nucleosides. The motifs described below can also be applied to crRNAs of other lengths, wherein the pattern is extended or shortened as required to fit the oligonucleotide length. The modifications of the motifs are described using the same single letter identifiers used in the subscripts of Tables 1-4 above. The number subscripts indicate the number of contiguous nucleosides that comprise the identified modification. The lack of a number subscript indicates one nucleoside. Additional abbreviations are: "l" indicates an LNA modification, "(MOP)" indicates a methoxypropyl modified internucleoside linkage, "(MP)" indicates a methylphosphonate internucleoside linkage, "(MMI)" indicates an MMI N-methyl internucleoside linkage, "(5-propyne)" indicates a 5-propyne nucleobase modification, and "(G-clamp)" indicates a G-clamp modified nucleobase.

TABLE 5 crRNA modification motifs

| 29-mers | 42-mers |
|---|---|
| $f_7r_6kr_3kr_3krk_2$ | $f_{10}r_{18}kr_4kr_2kr_3k_2$ |
| $mf_6r_6kr_3kr_3kr_3krk_2$ | $mf_9r_{18}kr_4kr_2kr_3k_2$ |
| $mf_6r_{10}k_6r_2k_4$ | $mr_{27}kr_4kr_2kr_3k_2$ |
| $mr_{16}k_6r_2k_4$ | $mr_9f_{10}k_6r_2kr_4kr_2kr_3k_2$ |
| $mr_6r_{10}k_6r_2k_4$ | $mr_9r_{10}l_6r_2kr_4kr_2kr_3k_2$ |
| $mf_6r_{10}f_6r_2k_4$ | $mr_9f_{16}r_2kr_4kr_2kr_3k_2$ |
| $mf_6r_{10}l_6r_2k_4$ | $mr_{32}kr_2kr_3k_2$ |
| $mr_6r_{10}l_6r_2k_4$ | $ef_9r_{18}kr_4kr_2kr_3k_2$ |
| $mf_6r_{10}k_6r_2l_4$ | $r(MOP)f_9r_{18}kr_4kr_2kr_3k_2$ |
| $mr_{16}k_6r_2l_4$ | $d(MOP)f_9r_{18}kr_4kr_2kr_3k_2$ |
| $mr_6r_{10}k_6r_2l_4$ | $f(MOP)f_9r_{18}kr_4kr_2kr_3k_2$ |
| $mf_6r_{10}f_6r_2l_4$ | $r(MP)f_9r_{18}kr_4kr_2kr_3k_2$ |
| $r(MOP)f_6r_6kr_3kr_3kr_3krk_2$ | $d(MP)f_9r_{18}kr_4kr_2kr_3k_2$ |
| $d(MOP)f_6r_6kr_3kr_3kr_3krk_2$ | $f(MP)f_9r_{18}kr_4kr_2kr_3k_2$ |
| $f(MOP)f_6r_6kr_3kr_3kr_3krk_2$ | $r(MMI)f_9r_{18}kr_4kr_2kr_3k_2$ |
| $r(MP)f_6r_6kr_3kr_3kr_3krk_2$ | $d(MMI)f_9r_{18}kr_4kr_2kr_3k_2$ |
| $d(MP)f_6r_6kr_3kr_3kr_3krk_2$ | $f(MMI)f_9r_{18}kr_4kr_2kr_3k_2$ |
| $f(MP)f_6r_6kr_3kr_3kr_3krk_2$ | $mr_{32}kr_2k(G\text{-}Clamp)r_2k_2$ |
| $r(MOP)f_6r_{10}k_6r_2k_4$ | $mr_{27}k_3r_2kr_2kr_3k_2$ |
| $d(MOP)f_6r_{10}k_6r_2k_4$ | $mf_9r_{18}k_3r_2kr_3k_2$ |
| $f(MOP)f_6r_{10}k_6r_2k_4$ | $mf_9r_{11}(5\text{-}Propyne\text{-}U)_4r_3k_3r_2kr_2k_2$ |
| $r(MP)f_6r_{10}k_6r_2k_4$ | 29-mers |
| $r(MP)f_6r_{10}k_6r_2k_4$ | $d(MOP)r_6f_{10}k_6r_2k_4$ |
| $r(MP)f_6r_{10}k_6r_2k_4$ | $f(MOP)r_6f_{10}k_6r_2k_4$ |

TABLE 5-continued crRNA modification motifs

| | |
|---|---|
| $r(MOP)r_{16}k_6r_2k_4$ | $r(MP)r_6f_{10}k_6r_2k_4$ |
| $d(MOP)r_{16}k_6r_2k_4$ | $d(MOP)r_6f_{10}k_6r_2k_4$ |
| $f(MOP)r_{16}k_6r_2k_4$ | $f(MOP)r_6f_{10}k_6r_2k_4$ |
| $r(MP)r_{16}k_6r_2k_4$ | $r(MOP)f_6r_{10}l_6r_2k_4$ |
| $d(MP)r_{16}k_6r_2k_4$ | $d(MOP)f_6r_{10}l_6r_2k_4$ |
| $f(MP)r_{16}k_6r_2k_4$ | $f(MOP)f_6r_{10}l_6r_2k_4$ |
| $r(MOP)r_6r_{10}k_6r_2k_4$ | $r(MOP)f_6r_{10}l_6r_2k_4$ |
| $d(MP)f_6r_{10}k_6r_2l_4$ | $d(MOP)f_6r_{10}f_6r_2l_4$ |
| $f(MP)f_6r_{10}k_6r_2l_4$ | $f(MOP)f_6r_{10}f_6r_2l_4$ |
| $r(MOP)r_{16}k_6r_2l_4$ | $f_7r_6kr_3kr_3k(G\text{-}Clamp)k_2$ |
| $d(MOP)r_{16}k_6r_2l_4$ | $mf_6r_6kr_3kr_3k(G\text{-}Clamp)rk_2$ |
| $f(MOP)r_{16}k_6r_2l_4$ | $mf_6r_{10}k_6r_2k(G\text{-}Clamp)k_2$ |
| $r(MP)r_{16}k_6r_2l_4$ | $mr_{16}k_6r_2k(G\text{-}Clamp)k_2$ |
| $d(MP)r_{16}k_6r_2l_4$ | $mr_6f_{10}k_6r_2k(G\text{-}Clamp)k_2$ |
| $f(MP)r_{16}k_6r_2l_4$ | $mf_6r_{10}f_6r_2k(G\text{-}Clamp)k_2$ |
| $r(MOP)r_6f_{10}k_6r_2l_4$ | $mf_6r_{10}l_6r_2k(G\text{-}Clamp)k_2$ |
| $r(MOP)r_6f_{10}k_6r_2l_4$ | $mr_6r_{10}l_6r_2k(G\text{-}Clamp)k_2$ |
| $r(MOP)r_6f_{10}k_6r_2l_4$ | $mf_6r_{10}k_6r_2l(G\text{-}Clamp)l_2$ |
| $r(MOP)r_6f_{10}k_6r_2l_4$ | $mr_{16}k_6r_2l(G\text{-}Clamp)l_2$ |
| $r(MOP)r_6f_{10}k_6r_2l_4$ | $mr_6f_{10}k_6r_2l(G\text{-}Clamp)l_2$ |
| $r(MOP)r_6f_{10}k_6r_2l_4$ | $mf_6r_{10}f_6r_2l(G\text{-}Clamp)l_2$ |
| $r(MOP)f_6r_{10}f_6r_2l_4$ | $f_7r_6kr_3k(5\text{-}propyne)r_3kr_3krk_2$ |
| $d(MOP)f_6r_{10}f_6r_2l_4$ | $mf_6r_6kr_3k(5\text{-}Propyne)r_3kr_3krk_2$ |
| $f(MOP)f_6r_{10}f_6r_2l_4$ | $r(MOP)f_6r_{10}f_6r_2l_4$ |

Example 6: Gene Editing Effects of Modified crRNA on the hVEGFA Locus

Modified crRNAs comprising a DNA recognition portion that is complementary to hVEGFA were designed and synthesized to test their effects on gene editing of the human VEGFA locus. HEK 293T cells were transfected as described in Example 1 using a crRNA described in the table below. The SURVEYOR assay was performed as described in Example 1, and the PCR primers used to amplify the crRNA target site were forward: 5'-TCCAGATGGCACAT-TGTCAG-3' (SEQ ID NO: 3) and reverse: 5'-AGG-GAGCAGGAAAGTGAGGT-3' (SEQ ID NO: 4). Following Cell cleavage, the DNA was run on a gel to analyze the extent of gene editing of hVEGFA, and the gel was quantified as described in Example 1. The results for the modified crRNAs were normalized to a positive control sgRNA targeted to hVEGFA to determine the gene disruption percentage shown in the table below. The results indicate that many of the modified crRNAs were active and some were even more active than the sgRNA positive control.

TABLE 6 crNA targeting hVEGFA

| Isis No. | Sequence (5' to 3') | Gene disruption, normalized to sgRNA (%) | SEQ ID NO. |
|---|---|---|---|
| 834463 | $G_{ms} G_{rs} U_{rs} G_{rs} A_{rs} G_{rs} U_{rs} G_{rs} A_{rs} G_{rs} U_{rs} G_{rs} U_{rs} G_{rs} U_{rs} G_{rs} C_{rs} G_{rs} U_{rs} G_{rs} G_{rs} U_{rs} U_{rs} U_{rs} U_{rs} A_{rs} G_{rs} A_{rs} G_{rs} C_{rs} U_{rs} A_{rs} U_{rs} G_{rs} C_{rs} U_{rs} G_{rs} U_{ms} U_{ms} U_{ms} U_{ms} G_m$ | 106 | 6 |
| 834464 | $G_{rs} G_{rs} U_{rs} G_{rs} A_{rs} G_{rs} U_{rs} G_{rs} A_{rs} G_{rs} U_{rs} G_{rs} U_{rs} G_{rs} U_{rs} G_{rs} C_{rs} G_{rs} U_{rs} G_{rs} G_{rs} U_{rs} U_{rs} U_{rs} U_{rs} A_{rs} G_{rs} A_{rs} G_{ks} C_{rs} U_{rs} A_{rs} U_{rs} G_{ks} C_{rs} U_{rs} G_{ks} U_{rs} U_{rs} U_{rs} T_{ks} G_k$ | 63 | 8 |
| 834465 | $G_{ms} G_{rs} U_{rs} G_{rs} A_{rs} G_{rs} U_{rs} G_{rs} A_{rs} G_{rs} U_{rs} G_{rs} U_{rs} G_{rs} U_{rs} G_{rs} C_{rs} G_{rs} U_{rs} G_{rs} G_{rs} U_{rs} U_{rs} U_{rs} U_{rs} A_{rs} G_{rs} A_{rs} G_{ks} C_{rs} U_{rs} A_{rs} U_{rs} G_{ks} C_{rs} U_{rs} G_{ks} U_{rs} U_{rs} U_{rs} T_{ks} G_k$ | 93 | 8 |
| 834466 | $G_{fs} G_{fs} U_{fs} G_{fs} A_{fs} G_{fs} U_{fs} G_{fs} A_{rs} G_{rs} U_{rs} G_{rs} U_{rs} G_{rs} U_{rs} G_{rs} C_{rs} G_{rs} U_{rs} G_{rs} G_{rs} U_{rs} U_{rs} U_{rs} T_{ks} A_{rs} G_{rs} A_{rs} G_{ks} C_{rs} T_{ks} A_{ks} U_{rs} G_{ks} C_{rs} U_{rs} G_{ks} U_{rs} U_{rs} U_{rs} T_{ks} G_k$ | 61 | 15 |
| 834467 | $G_{rs} G_{rs} U_{rs} G_{rs} A_{rs} G_{rs} U_{rs} G_{rs} A_{rs} G_{rs} U_{rs} G_{rs} U_{rs} G_{rs} U_{rs} G_{rs} C_{rs} G_{rs} U_{rs} G_{ks} U_{rs} U_{rs} U_{rs} T_{ks} A_{rs} G_{rs} A_{rs} G_{ks} C_{rs} T_{ks} A_{ks} U_{rs} G_{ks} C_{rs} U_{rs} G_{ks} U_{rs} U_{rs} U_{rs} T_{ks} G_k$ | 57 | 15 |

TABLE 6-continued crNA targeting hVEGFA

| Isis No. | Sequence (5' to 3') | Gene disruption, normalized to sgRNA (%) | SEQ ID NO. |
|---|---|---|---|
| 834468 | $G_{ms}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_{ks}$ $U_{rs}$ $G_{ks}$ $C_{rs}$ $U_{rs}$ $G_{ks}$ $U_{rs}$ $U_{rs}$ $U_{rs}$ $T_{ks}$ $G_k$ | 38 | 15 |
| 834469 | $G_{fs}$ $G_{fs}$ $U_{fs}$ $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{ks}$ $G_{rs}$ $C_{rs}$ $T_{rs}$ $A_k$ | 68 | 11 |
| 834470 | $G_{rs}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{rs}$ $A_{rs}$ $G_{ks}$ $C_{rs}$ $T_{ks}$ $A_k$ | 75 | 11 |
| 834471 | $G_{ms}$ $G_{rs}$ $U_{rs}$ $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | <1 | 11 |
| 834472 | $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | 107 | 13 |
| 834475 | $G_{fs}$ $A_{fs}$ $G_{fs}$ $U_{fs}$ $G_{fs}$ $A_{fs}$ $G_{fs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $T_{ks}$ $U_{rs}$ $T_{ks}$ $A_{rs}$ $G_{rs}$ $A_{rs}$ $G_{ks}$ $C_{rs}$ $T_{ks}$ $A_k$ | <1 | 16 |
| 834476 | $G_{ms}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | 71 | 13 |
| 834477 | $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_k$ | 67 | 13 |
| 834478 | $G_{ms}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $T_{ks}$ $U_{rs}$ $T_{ks}$ $A_{rs}$ $G_{rs}$ $A_{rs}$ $G_{ks}$ $C_{rs}$ $T_{ks}$ $A_k$ | <1 | 16 |
| 834479 | $G_{rs}$ $A_{rs}$ $G_{rs}$ $U_{rs}$ $G_{rs}$ $A_{rs}$ $G_{rs}$ $U_{rs}$ $G_{rs}$ $U_{rs}$ $G_{rs}$ $U_{rs}$ $G_{rs}$ $C_{rs}$ $G_{rs}$ $U_{rs}$ $G_{rs}$ $G_{ks}$ $U_{rs}$ $T_{ks}$ $U_{rs}$ $T_{ks}$ $A_{rs}$ $G_{rs}$ $A_{rs}$ $G_{ks}$ $C_{rs}$ $T_{ks}$ $A_k$ | <1 | 16 |

Subscripts: "m" indicates a 2'-O-methyl modification, "s" indicates a phosphorothioate internucleoside linkage, "f" indicates a 2'-F modification, "r" indicates an unmodified 2'-hydroxy sugar moiety, "d" indicates an unmodified 2'-deoxy sugar moiety, and "k" indicates a cEt modification. The underlined nucleosides represent the DNA recognition portion of the crRNA, the nucleosides that are not underlined represent the tracrRNA recognition portion of the crRNA.

Example 7: Off-Target Effects of Modified crRNAs

In order to test the off-target effects of modified crRNAs, Isis Numbers 801193 (Example 3), 801381 (Example 4), and 834472 (Example 6) were tested for their effects on gene editing of the human Myc-associated factor X (MAX) locus. At chromosome position $14q_{23}$, the MAX gene carries an 18 out of 20 nucleotide match to a portion of or all of the region of the VEGFA gene targeted by Isis Numbers 801193, 801381, and 834472. HEK 293T cells were transfected as described in Example 1 using Isis No. 801193, 801381, or 834472 as the modified crRNA. The SURVEYOR assay was performed as described in Example 1, and the PCR primers used to amplify the off-target site in the MAX gene were forward: 5'-TACCCGGGCCGTCTGTTAGA-3' (SEQ ID NO: 17) and reverse: 5'-GAGGGGGAAGTCACCGACAA-3' (SEQ ID NO: 18). Following Cell cleavage, the DNA was run on a gel to analyze the extent of gene editing of MAX. Quantification was performed as described in Example 1. The results for the modified crRNAs were normalized to a positive control sgRNA targeted to hVEGFA to determine the gene disruption percentage shown in the table below. The results indicate that the modified crRNAs exhibited less off-target effects than the sgRNA control. The on-target effects of the modified crRNAs (see Examples 3, 4, and 6) are shown in the third column below, for comparison.

TABLE 7

Effect of crRNA targeting VEGFA on off-target MAX

| Isis No. | Off-target gene disruption, normalized to sgRNA (%) | On-target gene disruption, normalized to sgRNA (%, from above examples) |
|---|---|---|
| 801193 | 28 | 75 |
| 801381 | 13 | 42 |
| 834472 | 20 | 107 |

Example 8: Gene Editing Effects of Modified crRNA on hTTR Locus

Modified crRNAs comprising a DNA recognition portion that is complementary to human TTR were designed and synthesized to test their effects on gene editing of the hTTR locus. HEK 293T cells were transfected as described in Example 1 using a crRNA described in the table below. The SURVEYOR assay was performed as described in Example 1, and the PCR primers used to amplify the crRNA target site were forward: 5'-GCTGACTAAGCAAAGCTTC-CAAATGAC-3' (SEQ ID NO:41) and reverse: 5'-GATGT-CACAGAAACACTCACCGTAG-3' (SEQ ID NO: 42). Following Cell cleavage, the DNA was run on a gel to analyze the extent of gene editing of hTTR, and the gel was quantified as described in Example 1. The results for the modified crRNAs were normalized to a positive control sgRNA targeted to hTTR to determine the gene disruption percentage shown in the table below. The results indicate that many of the modified crRNAs were active and some were even more active than the sgRNA positive control.

TABLE 8 crRNA targeting hTTR

| Name or Ion No. | Sequence (5' to 3') | Gene disruption, normalized to sgRNA (%) | SEQ ID NO. |
|---|---|---|---|
| 42RTT MAS | $G_{ms}$ $A_{rs}$ $C_{rs}$ $A_{rs}$ $A_{rs}$ $G_{rs}$ $G_{rs}$ $U_{rs}$ $\underline{U_{rs}}$ $\underline{C_{rs}}$ $\underline{A_{rs}}$ $\underline{U_{rs}}$ $\underline{A_{rs}}$ $\underline{U_{rs}}$ $\underline{U_{rs}}$ $\underline{U_{rs}}$ $\underline{G_{rs}}$ $\underline{U_{rs}}$ $\underline{A_{rs}}$ $\underline{U_{rs}}$ $\underline{G_{rs}}$ $\underline{U_{rs}}$ $\underline{U_{rs}}$ $\underline{U_{rs}}$ $\underline{U_{rs}}$ $\underline{A_{rs}}$ $\underline{G_{rs}}$ $\underline{A_{rs}}$ $\underline{G_{rs}}$ $\underline{C_{rs}}$ $\underline{U_{rs}}$ $\underline{A_{rs}}$ $\underline{U_{rs}}$ $\underline{G_{rs}}$ $\underline{C_{rs}}$ $\underline{U_{rs}}$ $\underline{G_{rs}}$ $U_{ms}$ $U_{ms}$ $U_{ms}$ $U_{ms}$ $G_m$ | 125 | 43 |
| 895589 | $G_{fs}$ $A_{fs}$ $C_{fs}$ $A_{fs}$ $A_{fs}$ $G_{fs}$ $G_{fs}$ $U_{fs}$ $\underline{U_{fs}}$ $\underline{C_{fs}}$ $\underline{A_{rs}}$ $\underline{U_{rs}}$ $\underline{A_{rs}}$ $\underline{U_{rs}}$ $\underline{U_{rs}}$ $\underline{U_{rs}}$ $\underline{G_{rs}}$ $\underline{U_{rs}}$ $\underline{A_{rs}}$ $\underline{U_{rs}}$ $\underline{G_{rs}}$ $\underline{U_{rs}}$ $\underline{U_{rs}}$ $\underline{U_{rs}}$ $\underline{U_{rs}}$ $\underline{A_{rs}}$ $\underline{G_{rs}}$ $\underline{A_{rs}}$ $\underline{G_{ks}}$ $\underline{C_{rs}}$ $\underline{U_{rs}}$ $\underline{A_{rs}}$ $\underline{U_{rs}}$ $\underline{G_{ks}}$ $\underline{C_{rs}}$ $\underline{U_{rs}}$ $\underline{G_{ks}}$ $\underline{U_{rs}}$ $\underline{U_{rs}}$ $\underline{U_{rs}}$ $T_{ks}$ $G_k$ | 118 | 44 |
| 895591 | $G_{fs}$ $A_{fs}$ $C_{fs}$ $A_{fs}$ $A_{fs}$ $G_{fs}$ $G_{fs}$ $U_{fs}$ $\underline{U_{fs}}$ $\underline{C_{fs}}$ $\underline{A_{rs}}$ $\underline{U_{rs}}$ $\underline{A_{rs}}$ $\underline{U_{rs}}$ $\underline{U_{rs}}$ $\underline{U_{rs}}$ $\underline{G_{rs}}$ $\underline{U_{rs}}$ $\underline{A_{rs}}$ $\underline{U_{rs}}$ $\underline{G_{ks}}$ $\underline{U_{rs}}$ $\underline{U_{rs}}$ $\underline{U_{rs}}$ $T_{ks}$ $A_{rs}$ $G_{rs}$ $A_{rs}$ $G_{ks}$ $C_{rs}$ $T_{ks}$ $A_k$ | 77 | 45 |
| 895593 | $G_{fs}$ $A_{fs}$ $C_{fs}$ $A_{fs}$ $A_{fs}$ $G_{fs}$ $G_{fs}$ $U_{fs}$ $\underline{U_{fs}}$ $\underline{C_{fs}}$ $\underline{A_{rs}}$ $\underline{U_{rs}}$ $\underline{A_{rs}}$ $\underline{U_{rs}}$ $\underline{U_{rs}}$ $\underline{U_{rs}}$ $\underline{G_{rs}}$ $\underline{U_{rs}}$ $\underline{A_{rs}}$ $\underline{U_{rs}}$ $\underline{G_{ks}}$ $\underline{U_{rs}}$ $\underline{U_{rs}}$ $\underline{U_{rs}}$ $T_{ks}$ $A_{rs}$ $G_{rs}$ $A_{rs}$ $G_{ks}$ $C_{rs}$ $U_{rs}$ $A_{ks}$ $U_{rs}$ $G_{rs}$ $C_{rs}$ $U_{rs}$ $G_{ks}$ $U_{rs}$ $U_{rs}$ $U_{rs}$ $T_{ks}$ $G_k$ | 107 | 46 |

Subscripts: "m" indicates a 2'-O-methyl modification, "s" indicates a phosphorothioate internucleoside linkage, "f" indicates a 2'-F modification, "r" indicates an unmodified 2'-hydroxy sugar moiety. The underlined nucleosides represent the DNA recognition portion of the crRNA, the nucleosides that are not underlined represent the tracrRNA recognition portion of the crRNA.

Example 9: Gene Alteration Effects of Truncated scrRNA

Figure 4:
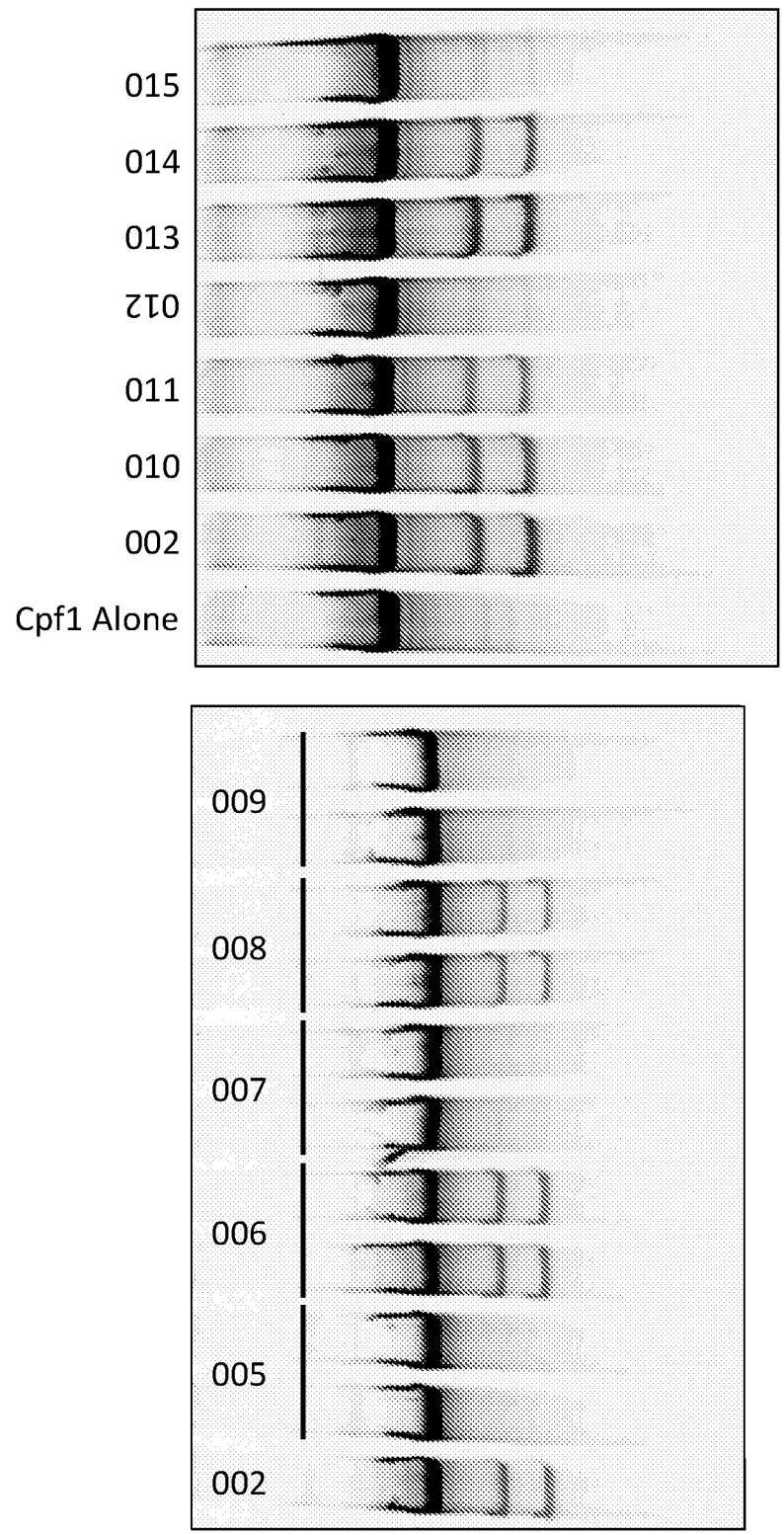
FIGS. 4a and 4b are gels that show the effect of truncated scrRNAs comprising a scrRNA target recognition portion that is complementary to DNA (cytosine-5)-methyltransferase 1 (DNMT1) on alteration of the DNMT1 gene.

Truncated scrRNAs comprising a scrRNA target recognition portion that is complementary to DNA (cytosine-5)-methyltransferase 1 (DNMT1) were designed and synthesized to test their effects on alteration of the DNMT1 gene. HEK293T cells were transfected with a plasmid encoding Cpf1 and a double-stranded gblock (IDT, Coralville, Iowa) encoding a scrRNA listed in the table below. The SUR-VEYOR assay was performed as described in Example 1, and the PCR primers used to amplify the scrRNA site in the DNMT1 gene were forward: 5'-CTGGGACTCAGGCGGGTCAC-3' (SEQ ID NO: 47) and reverse: 5'-CCTCACACAACAGCTTCATGTCAGC-3' (SEQ ID NO:). Following Cell cleavage, the DNA was run on a gel to analyze the extent of gene alteration of DNMT1. The results are shown in FIGS. 4a and 4b. The results indicate that multiple truncated scrRNAs, including scrRNA containing only 36 nucleotides, altered the target gene.

TABLE 9 scrRNA targeting DNMT1

| Name | Sequence (5' to 3') | SEQ ID NO. |
|---|---|---|
| 002 | TAATTTCTACTCTTGTAGAT<u>CTGATGGTCCATGTCTGTTACTC</u> | 49 |
| 005 | TTCTACTCTTGTAGAT<u>CTGATGGTCCATGTCTGTTACTC</u> | 50 |
| 006 | TAATTTCTACTCTTGTAGAT<u>CTGATGGTCCATGTCTGTTA</u> | 51 |
| 007 | TTCTACTCTTGTAGAT<u>CTGATGGTCCATGTCTGT</u> | 52 |
| 008 | TAATTTCTACTCTTGTAGAT<u>CTGATGGTCCATGTCTGT</u> | 53 |
| 009 | TTCTACTCTTGTAGAT<u>CTGATGGTCCATGTCTGTTA</u> | 54 |
| 010 | AATTTCTACTCTTGTAGAT<u>CTGATGGTCCATGTCTGT</u> | 55 |
| 011 | ATTTCTACTCTTGTAGAT<u>CTGATGGTCCATGTCTGT</u> | 56 |
| 012 | TTTCTACTCTTGTAGAT<u>CTGATGGTCCATGTCTGT</u> | 57 |
| 013 | AATTTCTACTCTTGTAGAT<u>CTGATGGTCCATGTCTGTTACTC</u> | 58 |
| 014 | ATTTCTACTCTTGTAGAT<u>CTGATGGTCCATGTCTGTTACTC</u> | 59 |
| 015 | TTTCTACTCTTGTAGAT<u>CTGATGGTCCATGTCTGTTACTC</u> | 60 |

All of the nucleosides in the table above are unmodified ribonucleosides comprising 2'-hydroxy sugar moieties and phosphate internucleoside linkages. The underlined nucleosides represent the target recognition portion of the scrRNA, the nucleosides that are not underlined represent the nuclease recognition portion of the scrRNA.

Example 10: DNA Cutting Effects of Truncated tracrRNA

Figure 5:
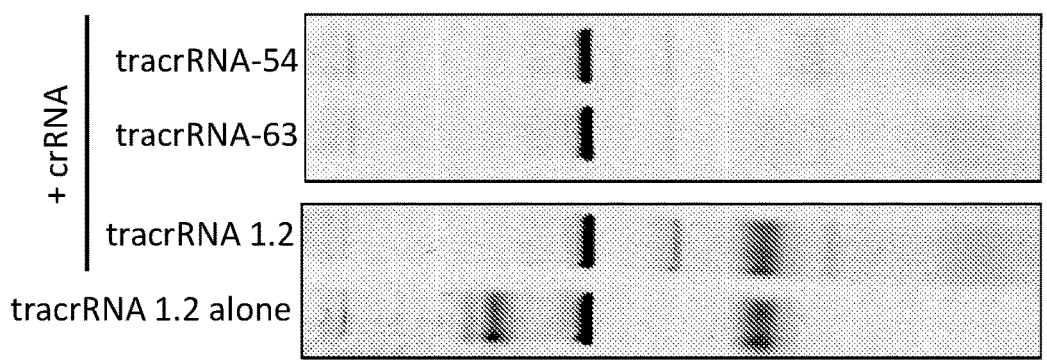
FIG. 5 is a gel that shows the extent of activity of truncated tracrRNAs designed and synthesized to edit mouse Proprotein Convertase Subtilisin/Kexin Type 9 (Pcsk9).

Truncated tracrRNAs were designed and synthesized to test their effects on editing of mouse Proprotein Convertase Subtilisin/Kexin Type 9 (Pcsk9). To generate Pcsk9 DNA, a portion of the mouse genomic locus encompassing the CRISPR target site was amplified by PCR using primers 5'-CTGAGGCTAGAGGACTGAGC-3' (SEQ ID NO: 61) and 5'-CAGACGGCTAGATGAGCAGAG-3' (SEQ ID NO: 62). 30 nM of a modified crRNA, Ion No. 927720, shown in the table below and 30 nM of a tracrRNA shown in the table below and were used to test for Pcsk9 gene disruption in an in vitro biochemical assay. Following cleavage by Cas9, the DNA was run on a gel to analyze the extent of activity. The results are shown in FIG. 5. The results indicate that the truncated tracrRNAs exhibited activity in vitro.

TABLE 10

Modified crRNA targeting human PCsk9 and truncated tracrRNAs

| Ion No. or Name | Sequence (5' to 3') | SEQ ID NO. |
|---|---|---|
| 927720 | $A_{ms}$ $C_{rs}$ $C_{rs}$ $G_{rs}$ $C_{rs}$ $A_{rs}$ $G_{rs}$ $C_{rs}$ $C_{rs}$ $A_{rs}$ $C_{rs}$ $G_{rs}$ $C_{rs}$ $A_{rs}$ $G_{rs}$ $A_{rs}$ $G_{rs}$ $C_{rs}$ $A_{rs}$ $G_{rs}$ $G_{rs}$ $U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{ms}$ $U_{ms}$ $U_{ms}$ $U_{ms}$ $G_m$ | 63 |

TABLE 10-continued

Modified crRNA targeting human PCsk9 and truncated tracrRNAs

| Ion No. or Name | Sequence (5' to 3') | SEQ ID NO. |
|---|---|---|
| tracrRNA 1.2 (pos. ctrl) | GTTGGAACCATTCAAAACAGCATAGCAAGTT AAAATAAGGCTAGTCCGTTATCAACTTGGCC AACATGAGGATCACCCATGTCTGCAGGGCCA AGTGGCACCGAGTCGGTGCTTT | 64 |
| tracrRNA 63 | GGAACCATTCAAAACAGCATAGCAAGTTAAA ATAAGGCTAGTCCGTTATCAACTTGAAAAAGT | 65 |
| tracrRNA 54 | CAAAACAGCATAGCAAGTTAAAATAAGGCTA GTCCGTTATCAACTTGAAAAAGT | 66 |

Subscripts: "m" indicates a 2'-O-methyl modification, "s" indicates a phosphorothioate internucleoside linkage, "r" indicates an unmodified 2'-hydroxy sugar moiety. The underlined nucleosides represent the DNA recognition portion of the crRNA. All of the nucleosides in the tracrRNAs shown in the table above are unmodified ribonucleosides comprising 2'-hydroxy sugar moieties and phosphate internucleoside linkages.

Example 11: Gene Activation Following Free Uptake of Modified crRNA

The ability of modified crRNAs to activate target genes was tested in a transcriptional activation assay, similar to that described in Konermann et al., *Nature* 517, 583-588 (2015). Briefly, one MS2 aptamer sequence was inserted at position 58 of tracrRNA. HEK 293 cells were transfected with PBS alone (negative control) or with a plasmids encoding catalytically inactive Cas9 fused to Tetrameric VP16 transcription activator domain (dCas9-VP64), MS2-p65-HSF1 activation helper protein as described in Konermann et al. and the MS2 aptamer containing tracrRNA1.2. Modified crRNA comprising a DNA recognition portion that is complementary to human TTR, listed in the table below, was added in PBS, in the absence of a transfection reagent, at a final concentration of 1 uM. PBS without crRNA was added in the "no RNA" control. After 48 hours, total RNA was isolated, and gene activation was measured using RT-qPCR using forward primer 5'-CTTGCTGGACTGGTAT-TTGTGTCT-3'(SEQ ID NO: 67), reverse primer 5'-AGAACTTTGACCATCAGAGGACACT-3' (SEQ ID NO: 68) and probe 5'-CCCTACGGGCACCGGTGAATCC-3' (SEQ ID NO: 69). The RT-qPCR results were normalized to GAPDH and are presented in the table below as the fold change relative to the negative control, which was set to 1.0. The results show that modified crRNA was taken up by the cells by free uptake and induced target gene activation.

TABLE 11

Gene activation following free uptake of modified crRNA

| Name | Sequence (5' to 3') | Fold change (Rel. to Neg Ctrl) | SEQ ID NO. |
|---|---|---|---|
| Neg Ctrl | n/a | 1.0 | |
| No RNA | n/a | 2.6 | |

TABLE 11-continued

Gene activation following free uptake of modified crRNA

| Name | Sequence (5' to 3') | Fold change (Rel. to Neg Ctrl) | SEQ ID NO. |
|---|---|---|---|
| crRNA 42 | $G_{ms}$ $A_{rs}$ $C_{rs}$ $A_{rs}$ $A_{rs}$ $G_{rs}$ $G_{rs}$ $T_{rs}$ $T_{rs}$ $C_{rs}$ $A_{rs}$ $T_{rs}$ $A_{rs}$ $T_{rs}$ $T_{rs}$ $T_{rs}$ $G_{rs}$ $T_{rs}$ $A_{rs}$ $T_{rs}$ $G_{rs}$ $T_{rs}$ $T_{rs}$ $T_{rs}$ $T_{rs}$ $A_{rs}$ $G_{rs}$ $A_{rs}$ $G_{rs}$ $C_{rs}$ $T_{rs}$ $A_{rs}$ $T_{rs}$ $G_{rs}$ $C_{rs}$ $T_{rs}$ $G_{rs}$ $T_{ms}$ $T_{ms}$ $T_{ms}$ $T_{ms}$ $G_{m}$ | 10.2 | 70 |

Subscripts: "m" indicates a 2'-O-methyl modification, "s" indicates a phosphorothioate internucleoside linkage, "r" indicates an unmodified 2'-hydroxy sugar moiety. The underlined nucleosides represent the DNA recognition portion of the crRNA.

Figure 6:
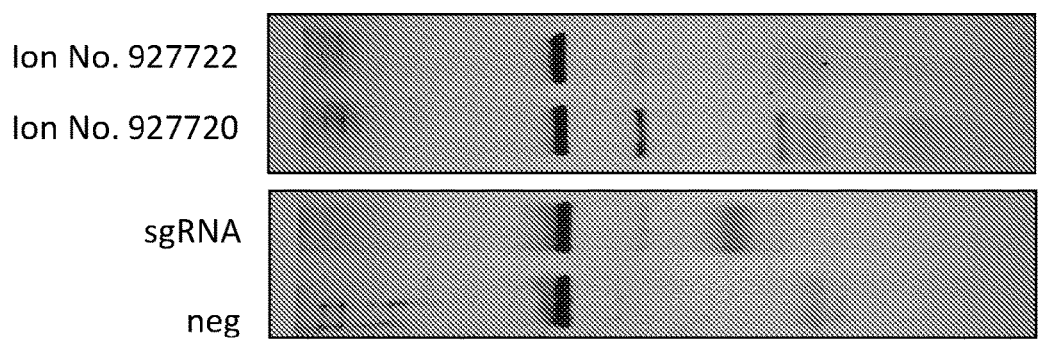
FIG. 6 is a gel that shows the DNA cutting activity of conjugated and unconjugated modified crRNA targeted to Pcsk9.

Example 12: In Vitro Digestion of Pcsk9 DNA Using Compounds Comprising Modified crRNA Compounds comprising modified crRNAs shown in the tables below comprise a DNA recognition portion that is complementary to mouse Pcsk9. The modified crRNAs shown in Table 12 below are made and tested for their DNA cutting activity and/or gene disruption activity, as described herein. The modified crRNAs shown in Table 13 were synthesized and tested for DNA cutting activity in vitro. Ion No. 927722 comprises a GalNAc conjugate group ("LICA-1"), and the synthesis of Ion No. 927722 is shown below. The DNA cutting assay was carried out as described in Example 10. Ion No. 927720 or 927722 was used with a tracrRNA. An sgRNA was used alone as a positive control. The results are shown in FIG. 6. The results show that the modified crRNA with no attached conjugate group cut Pcsk9 DNA more potently than the sgRNA positive control in vitro. The modified crRNA attached to the GalNAc conjugate group cut Pcsk9 DNA to an extent approximately equal to that of the sgRNA positive control.

TABLE 12

Modified crRNA targeting PCsk9

| Isis or Ion No. | Sequence (5' to 3') | SEQ ID NO. |
|---|---|---|
| 881061 | $A_{fs}$ $C_{fs}$ $C_{fs}$ $G_{fs}$ $C_{fs}$ $A_{fs}$ $G_{fs}$ $C_{fs}$ $C_{fs}$ $A_{fs}$ $C_{rs}$ $G_{rs}$ $C_{rs}$ $A_{rs}$ $G_{rs}$ $A_{rs}$ $G_{rs}$ $C_{rs}$ $A_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_{k}$ | 71 |
| 881063 | LICA-$1_o$-$A_{fs}$ $C_{fs}$ $C_{fs}$ $G_{fs}$ $C_{fs}$ $A_{fs}$ $G_{fs}$ $C_{fs}$ $C_{fs}$ $A_{fs}$ $C_{rs}$ $G_{rs}$ $C_{rs}$ $A_{rs}$ $G_{rs}$ $A_{rs}$ $G_{rs}$ $C_{rs}$ $A_{rs}$ $G_{rs}$ $G_{ks}$ $U_{rs}$ $U_{rs}$ $U_{rs}$ $T_{ks}$ $A_{rs}$ $G_{rs}$ $A_{rs}$ $G_{ks}$ $C_{rs}$ $T_{ks}$ $A_{k}$ | 71 |
| 927719 | $A_{rs}$ $C_{rs}$ $C_{rs}$ $G_{rs}$ $C_{rs}$ $A_{rs}$ $G_{rs}$ $C_{rs}$ $C_{rs}$ $A_{rs}$ $C_{rs}$ $G_{rs}$ $C_{rs}$ $A_{rs}$ $G_{rs}$ $A_{rs}$ $G_{rs}$ $C_{rs}$ $A_{rs}$ $G_{rs}$ $G_{rs}$ $U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{rs}$ $U_{rs}$ $U_{rs}$ $G_{r}$ | 63 |

TABLE 12-continued

Modified crRNA targeting PCsk9

| Isis or Ion No. | Sequence (5' to 3') | SEQ ID NO. |
|---|---|---|
| 927723 | $A_{fs}$ $C_{fs}$ $C_{fs}$ $G_{fs}$ $C_{fs}$ $A_{fs}$ $G_{fs}$ $C_{fs}$ $C_{fs}$ $A_{fs}$ $C_{rs}$ $G_{rs}$ $\underline{C_{rs}}$ $\underline{A_{rs}}$ $\underline{G_{rs}}$ $\underline{A_{rs}}$ $\underline{G_{rs}}$ $\underline{C_{rs}}$ $\underline{A_{rs}}$ $\underline{G_{rs}}$ $\underline{G_{rs}}$ $\underline{U_{rs}}$ $\underline{U_{rs}}$ $\underline{U_{rs}}$ $\underline{U_{rs}}$ $\underline{A_{rs}}$ $\underline{G_{rs}}$ $\underline{A_{rs}}$ $\underline{G_{ks}}$ $\underline{C_{rs}}$ $\underline{U_{rs}}$ $\underline{A_{rs}}$ $\underline{U_{rs}}$ $G_{ks}$ $C_{rs}$ $U_{rs}$ $U_{rs}$ $U_{rs}$ $T_{ks}$ $G_{rs}$ | 72 |
| 927725 | LICA-1$_o$-$A_{fs}$ $C_{fs}$ $C_{fs}$ $G_{fs}$ $C_{fs}$ $A_{fs}$ $G_{fs}$ $C_{fs}$ $C_{fs}$ $A_{fs}$ $C_{rs}$ $G_{rs}$ $C_{rs}$ $A_{rs}$ $G_{rs}$ $A_{rs}$ $G_{rs}$ $C_{rs}$ $A_{rs}$ $G_{rs}$ $G_{rs}$ $U_{rs}$ $U_{rs}$ $U_{rs}$ $U_{rs}$ $A_{rs}$ $G_{rs}$ $A_{rs}$ $G_{ks}$ $C_{rs}$ $U_{rs}$ $A_{rs}$ $U_{rs}$ $G_{ks}$ $C_{rs}$ $U_{rs}$ $G_{ks}$ $U_{rs}$ $U_{rs}$ $U_{rs}$ $T_{ks}$ $G_k$ | 72 |

TABLE 13a crRNA targeting PCsk9

| Ion No. | Sequence (5' to 3') | SEQ ID NO. |
|---|---|---|
| 927720 | $A_{ms}$ $C_{rs}$ $C_{rs}$ $G_{rs}$ $C_{rs}$ $A_{rs}$ $G_{rs}$ $C_{rs}$ $C_{rs}$ $A_{rs}$ $C_{rs}$ $G_{rs}$ $\underline{C_{rs}}$ $\underline{A_{rs}}$ $\underline{G_{rs}}$ $\underline{A_{rs}}$ $\underline{G_{rs}}$ $\underline{C_{rs}}$ $\underline{A_{rs}}$ $\underline{G_{rs}}$ $\underline{G_{rs}}$ $\underline{U_{rs}}$ $\underline{U_{rs}}$ $\underline{U_{rs}}$ $\underline{U_{rs}}$ $\underline{A_{rs}}$ $\underline{G_{rs}}$ $\underline{A_{rs}}$ $\underline{G_{rs}}$ $\underline{C_{rs}}$ $\underline{U_{rs}}$ $\underline{A_{rs}}$ $\underline{U_{rs}}$ $\underline{G_{rs}}$ $\underline{C_{rs}}$ $\underline{U_{rs}}$ $G_{rs}$ $U_{ms}$ $U_{ms}$ $U_{ms}$ $U_{ms}$ $G_m$ | 63 |
| 927722 | LICA-1$_o$-$A_{ms}$ $C_{rs}$ $C_{rs}$ $G_{rs}$ $C_{rs}$ $A_{rs}$ $G_{rs}$ $C_{rs}$ $C_{rs}$ $A_{rs}$ $C_{rs}$ $G_{rs}$ $C_{rs}$ $A_{rs}$ $G_{rs}$ $A_{rs}$ $G_{rs}$ $C_{rs}$ $A_{rs}$ $G_{rs}$ $G_{rs}$ $U_{rs}$ $U_{rs}$ $U_{rs}$ $U_{rs}$ $A_{rs}$ $G_{rs}$ $A_{rs}$ $G_{rs}$ $C_{rs}$ $U_{rs}$ $A_{rs}$ $U_{rs}$ $G_{rs}$ $C_{rs}$ $U_{rs}$ $G_{rs}$ $U_{ms}$ $U_{ms}$ $U_{ms}$ $U_{ms}$ $G_m$ | 63 |

Subscripts: "m" indicates a 2'-O-methyl modification, "s" indicates a phosphorothioate internucleoside linkage, "o" indicates a phosphate internuceoside linkage, "r" indicates an unmodified 2'-hydroxy sugar moiety. The underlined nucleosides represent the DNA recognition portion of the crRNA.

Synthesis of Ion Numbers 927720 and 927722:

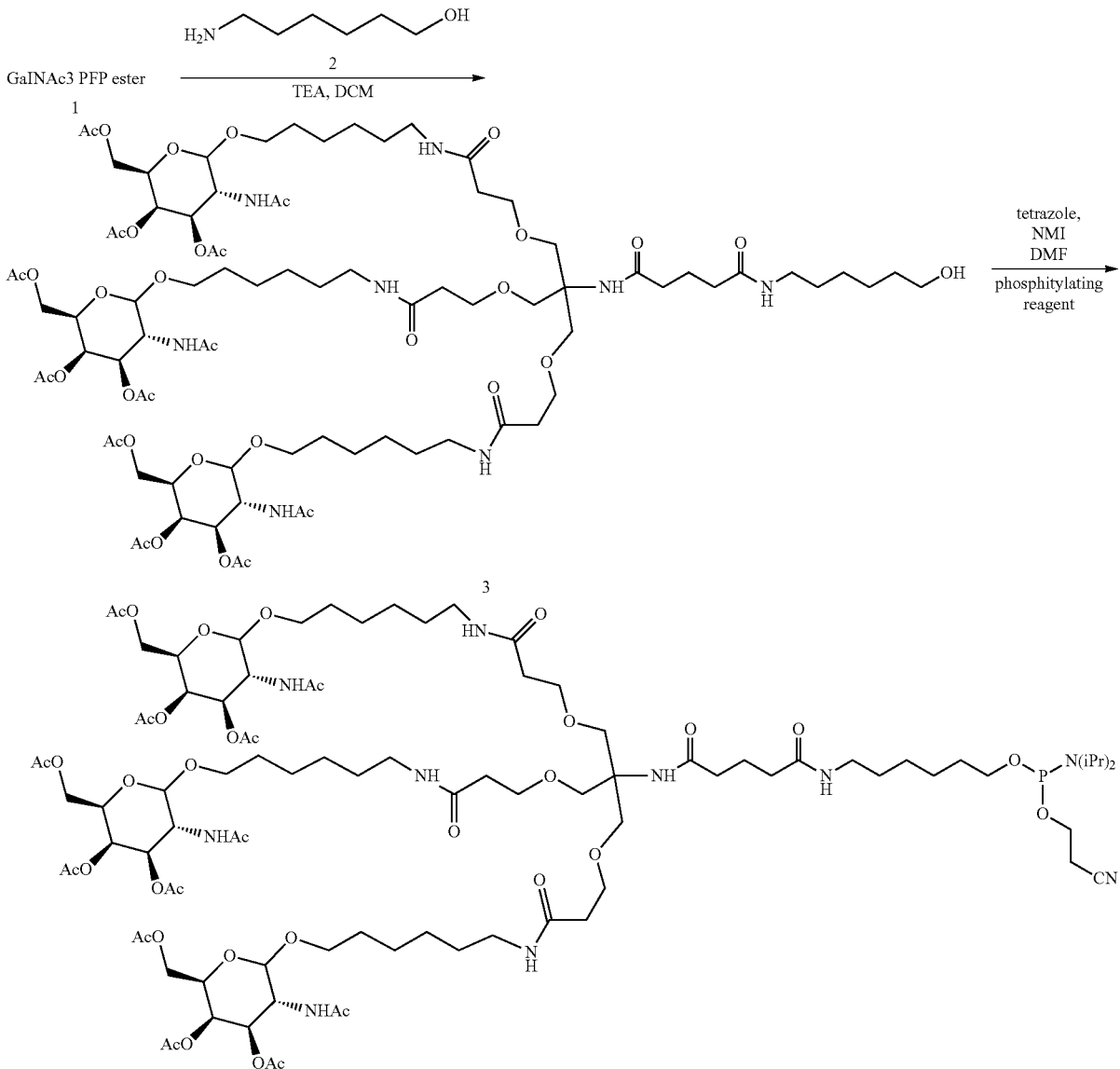

Compound 3

To a solution of THA-GalNAc3 PFP ester 1 (10 g, 5.3 mmol), TEA (1.47 mL, 10.5 mmol) in dichloromethane (40 mL), 6-amino-1-hexanol in dichloromethane (10 mL) was added dropwise. After stirring at room temperature for 12 h the reaction mixture was concentrated and residue was purified by silica gel column (Biotage Silica Gel Colum Chromatography, 220 g) and eluted with 5-20% MeOH in dichloromethane to yield 3 (9.1 g, 94%). LR MS (ESI) calcd for $C_{84}H_{139}O_{36}N_8$ [M+H]+ m/z=1837.1, found 1837.9.

Compound 4

To a DMF (25 mL) solution of 3 (8.96 g, 5.0 mmol) and tetrazole (0.273 g, 4.0 mmol) at 0° C., 1-methylimidazole (97 µL, 1 mmol) and phosphitylating reagent (2.3 mL, 7 mmol) were added. The reaction mixture was warmed to room temperature and stirred at the temperature for 12 h. The reaction mixture was extracted with ethyl acetate (100 mL), washed with sat. NaHCO$_3$ (100 mL) and brine (100 mL), dried over Na$_2$SO$_4$. After filtration the ethyl acetate solution was concentrated under reduced pressure. The residue obtained was purified by silica gel column chromatography and eluted first with ethyl acetate, then 50% acetone in ethyl acetate, followed by acetone and 50% acetone in THF to yield 4 (7.5 g, 75%) was obtained as white foam. $^{31}$P NMR (121 MHz, CDCl$_3$): δ 147.32; LR MS (ESI) calcd for $C_{93}H_{154}O_{37}N_{10}P$ [M-H]- m/z=2035.0, Found 2034.8.

Synthesis of Modified crRNAs, Ion Numbers 927720 and 927722

Standard phosphoramidites and solid supports were used for incorporation of A, U, G, and C nucleosides. A 0.2 M solution of the amidites in anhydrous acetonitrile was used for the synthesis. A 0.2 M solution of 2'-O-Me A$^{Bz}$, U, G$_{ibu}$ and C$^{Bz}$ phosphoramidites in anhydrous acetonitrile were used for the incorporation of 2'-O-methyl modified nucleotides. The modified crRNAs (60 µmol scale) were synthesized using an ÄKTAOligopilot synthesizer (GE Healthcare Biosciences) on VIMAD UnyLinker™ solid support (100 µmol/g loading) and the appropriate amounts of solid supports were packed in the column for synthesis. Dichloroacetic acid (6%) in toluene was used as detritylating reagent. 4,5-Dicyanoimidazole in the presence of N-methylimidazole in CH$_3$CN was used as activator during the coupling step. 0.1 M xanthane hydride solution in 50% pyridine in acetonitrile was used as sulfurizing agent with 3 min contact time. Twelve equivalents of THA-GalNAc phosphoramidite 4 was delivered in 3 portions, each followed by a 12 min coupling wait time. All other steps in the protocol supplied by the manufacturer were used without modification. The coupling efficiencies were more than 97%. After completion of the synthesis, solid support was treated with 20% diethylamine in toluene for 45 min to remove cyanoethyl group from phosphorothioate linkages. The solid support was then suspended in aqueous ammonium hydroxide (30 wt. %):ethanol (3:1) and allowed to stir at room temperature for 4 h. To this 10% (V/V) of methylamine in water (40 wt %) was added and stirring continued at room temperature for 24 h to complete the removal of all protecting groups except TBDMS group at 2'-position. The solid support was filtered and the filtrate was concentrated to dryness. The residue obtained was re-suspended in anhydrous triethylamine trihydrofluoride/triethylamine/1-methyl-2-pyrrolidinone solution (9.75 mL of a solution of 3 mL of triethylamine trihydofluoride, 2.25 mL triethylamine and 4.5 mL 1-methyl-2-pyrrolidinone, to provide a 1.4 M HF concentration) and heated at 65° C. for 4 h to remove the TBDMS groups at the 2'-position. The reaction was quenched with 1.5 M ammonium bicarbonate (9.95 mL) and diluted with water and purified by HPLC on a strong anion exchange column (GE Healthcare Bioscience, Source 30Q, 30 µm, 2.54×8 cm, A=100 mM ammonium acetate in 30% aqueous CH$_3$CN, B=1.5 M NaBr in A, 0-60% of B in 28 column volume, flow 14 mL min$^{-1}$). The fractions containing full length crRNAs were pooled together was desalted by HPLC on reverse phase column to yield the crRNA in an isolated yield of 10% based on solid-support loading. The oligonucleotides were characterized by ion-pair-HPLC-MS analysis with Agilent 1100 MSD system.

TABLE 13b

Analytical data of modified crRNAs

| Ion No. | Calcd Mass | Observed Mass |
|---------|------------|---------------|
| 927720  | 14206.1    | 14205.9       |
| 927722  | 15725.7    | 15724.2       |

Example 13: Gene Editing Effects of Modified crRNA on Pcsk9 Ex Vivo

Figure 7:
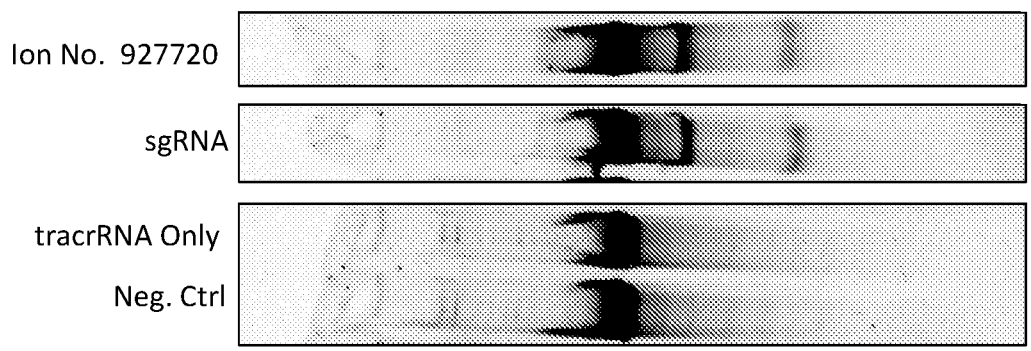
FIG. 7 is a gel that shows that a modified crRNA disrupted the Pcsk9 gene with similar potency to a sgRNA positive control in hepatocytes ex vivo.

Modified crRNA was tested for gene editing of Pcsk9 ex vivo. Hepatocytes from mice that express Cas9 (described in Platt et al., Cell 159, 440-455 (2014)) were cultured in William's media E supplemented with 10% FBS, 4 mM L-Glutamine and 25 mM HEPES. The hepatocytes were transfected with Ion No. 927720 (see Example 12) and a tracrRNA or a sgRNA positive control alone using lipofectamine RNAiMax (Life Technologies, Carlsbad). Pcsk9 gene disruption was measured using the SURVEYOR assay. The results are shown in FIG. 7. The results indicate that a modified crRNA disrupted the Pcsk9 gene with similar potency to a sgRNA positive control in hepatocytes ex vivo.

The invention claimed is:

1. A modified crRNA consisting essentially of 29 to 32 nucleosides, wherein each internucleoside linkage is a phosphorothioate internucleoside linkage, wherein:
 a. a first portion of the crRNA is a DNA recognition portion, and
 b. a second portion of the crRNA is a tracrRNA recognition portion having at least one nucleoside that comprises a bicyclic sugar moiety,
 wherein
  the DNA recognition portion is located 5' of the tracrRNA recognition portion,
  the seven 5'-terminal nucleosides of the DNA recognition portion comprise modified sugar moieties, at least one of which is a non-bicyclic sugar moiety,
  the DNA recognition portion comprises at least 10 consecutive nucleosides comprising unmodified 2'-hydroxy sugar moieties at the 3' end of the DNA recognition portion, and
  the 5' end of the tracrRNA recognition portion comprises the motif $kr_3$ wherein k is a cEt sugar moiety and r is an unmodified 2'-hydroxy sugar moiety.

2. The modified crRNA of claim 1, wherein the non-bicyclic sugar moiety is selected from 2'-O-methyl and 2'-F.

3. The modified crRNA of claim 1, wherein the modified sugar moieties of the seven 5'-terminal nucleosides are each independently selected from among 2'-O-methyl and 2'-F.

4. The modified crRNA of claim 1, wherein the modified sugar moieties of the seven 5'-terminal nucleosides are each 2'-F.

5. The modified crRNA of claim 1, wherein the tracrRNA recognition portion of the modified crRNA comprises at least 4 modified nucleosides.

6. The modified crRNA of claim 5, wherein the at least 4 modified nucleosides each comprise a modified sugar moiety comprising a bicyclic sugar moiety.

7. The modified crRNA of claim 1, wherein the 5' end of the tracrRNA recognition portion comprising the $kr_3$ motif comprises the motif $kr_3kr_3$, wherein each k is a cEt sugar moiety and each r is an unmodified 2'-hydroxy sugar moiety.

8. The modified crRNA of claim 1, wherein the seven 5'-terminal nucleosides of the DNA recognition portion comprise modified sugar moieties selected from among 2'-O-methyl and 2'-F and the tracrRNA recognition portion of the modified crRNA comprises at least 4 modified nucleosides selected from cEt and LNA.

9. The modified cRNA of claim 1, wherein the modified crRNA consists essentially of 29 nucleosides.

10. A compound consisting essentially of the modified crRNA of claim 1, and a conjugate group.

11. The compound of claim 10, wherein the conjugate group is selected from a GalNAc moiety and a GalNAc cluster.

12. A pharmaceutical composition comprising the modified crRNA of claim 1, a plasmid or a viral vector encoding a Cas9 protein, and a pharmaceutically acceptable carrier or diluent.

* * * * *

SEQUENCE LISTING

<160> NUMBER OF SEQ ID NOS: 72

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1
ggagacccaa atacaacaaa tc                    22

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
ctagactccg tctcaaagaa g                                           21

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
tccagatggc acattgtcag                                             20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
agggagcagg aaagtgaggt                                             20

<210> SEQ ID NO 5
<211> LENGTH: 43
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: bases at these positions are RNA
<220> FEATURE:
<221> NAME/KEY: misc_feature
<222> LOCATION: (8)..(9)
<223> OTHER INFORMATION: bases at these positions are RNA
<220> FEATURE:
<221> NAME/KEY: misc_feature
<222> LOCATION: (11)..(12)
<223> OTHER INFORMATION: bases at these positions are RNA
<220> FEATURE:
<221> NAME/KEY: misc_feature
<222> LOCATION: (14)..(43)
<223> OTHER INFORMATION: bases at these positions are RNA

<400> SEQUENCE: 5
gcgccttgct cctcgccgcg gguuuuagau cuaugcuguu uug                   43

<210> SEQ ID NO 6
<211> LENGTH: 42
<212> TYPE: RNA
<213> ORGANISM: Artificial sequence
<220> FEATURE:
<223> OTHER INFORMATION: Synthetic oligonucleotide

<400> SEQUENCE: 6
ggugagugag ugugugcgug guuuuagagc uaugcuguuu ug                    42

<210> SEQ ID NO 7
<211> LENGTH: 43

```
<212> TYPE: RNA
<213> ORGANISM: Artificial sequence
<220> FEATURE:
<223> OTHER INFORMATION: Synthetic oligonucleotide

<400> SEQUENCE: 7
gggugaguga gugugugcgu gguuuuagag cuaugcuguu uug          43

<210> SEQ ID NO 8
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(40)
<223> OTHER INFORMATION: bases at these positions are RNA
<220> FEATURE:
<221> NAME/KEY: misc_feature
<222> LOCATION: (42)..(42)
<223> OTHER INFORMATION: bases at these positions are RNA

<400> SEQUENCE: 8
ggugagugag ugugugcgug guuuuagagc uaugcuguuu tg           42

<210> SEQ ID NO 9
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 9
ggtgagtgag tgtgtgcgtg gttttagagc tatgctgttt tg           42

<210> SEQ ID NO 10
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(10)
<223> OTHER INFORMATION: bases at these positions are RNA
<220> FEATURE:
<221> NAME/KEY: misc_feature
<222> LOCATION: (12)..(18)
<223> OTHER INFORMATION: bases at these positions are RNA
<220> FEATURE:
<221> NAME/KEY: misc_feature
<222> LOCATION: (20)..(23)
<223> OTHER INFORMATION: bases at these positions are RNA
<220> FEATURE:
<221> NAME/KEY: misc_feature
<222> LOCATION: (26)..(30)
<223> OTHER INFORMATION: bases at these positions are RNA
<220> FEATURE:
<221> NAME/KEY: misc_feature
<222> LOCATION: (32)..(35)
<223> OTHER INFORMATION: bases at these positions are RNA
<220> FEATURE:
<221> NAME/KEY: misc_feature
<222> LOCATION: (37)..(37)
<223> OTHER INFORMATION: bases at these positions are RNA
<220> FEATURE:
<221> NAME/KEY: misc_feature
<222> LOCATION: (39)..(42)
<223> OTHER INFORMATION: bases at these positions are RNA

<400> SEQUENCE: 10
```
ggugagugag tgugugcgtg guuttagagc taugctgtuu ug          42

<210> SEQ ID NO 11
<211> LENGTH: 32
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(24)
<223> OTHER INFORMATION: bases at these positions are RNA
<220> FEATURE:
<221> NAME/KEY: misc_feature
<222> LOCATION: (26)..(30)
<223> OTHER INFORMATION: bases at these positions are RNA
<220> FEATURE:
<221> NAME/KEY: misc_feature
<222> LOCATION: (32)..(32)
<223> OTHER INFORMATION: bases at these positions are RNA

<400> SEQUENCE: 11
ggugagugag ugugugcgug guuutagagc ta                     32

<210> SEQ ID NO 12
<211> LENGTH: 32
<212> TYPE: RNA
<213> ORGANISM: Artificial sequence
<220> FEATURE:
<223> OTHER INFORMATION: Synthetic oligonucleotide

<400> SEQUENCE: 12
ggugagugag ugugugcgug guuuuagagc ua                     32

<210> SEQ ID NO 13
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: bases at these positions are RNA
<220> FEATURE:
<221> NAME/KEY: misc_feature
<222> LOCATION: (23)..(27)
<223> OTHER INFORMATION: bases at these positions are RNA
<220> FEATURE:
<221> NAME/KEY: misc_feature
<222> LOCATION: (29)..(29)
<223> OTHER INFORMATION: bases at these positions are RNA

<400> SEQUENCE: 13
gagugagugu gugcgugguu utagagcta                         29

<210> SEQ ID NO 14
<211> LENGTH: 29
<212> TYPE: RNA
<213> ORGANISM: Artificial sequence
<220> FEATURE:
<223> OTHER INFORMATION: Synthetic oligonucleotide

<400> SEQUENCE: 14
gagugagugu gugcgugguu uuagagcua                         29

<210> SEQ ID NO 15
<211> LENGTH: 42
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(24)
<223> OTHER INFORMATION: bases at these positions are RNA
<220> FEATURE:
<221> NAME/KEY: misc_feature
<222> LOCATION: (26)..(30)
<223> OTHER INFORMATION: bases at these positions are RNA
<220> FEATURE:
<221> NAME/KEY: misc_feature
<222> LOCATION: (32)..(40)
<223> OTHER INFORMATION: bases at these positions are RNA
<220> FEATURE:
<221> NAME/KEY: misc_feature
<222> LOCATION: (42)..(42)
<223> OTHER INFORMATION: bases at these positions are RNA

<400> SEQUENCE: 15
ggugagugag ugugugcgug guuutagagc taugcuguuu tg                       42

<210> SEQ ID NO 16
<211> LENGTH: 29
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA
<220> FEATURE:
<221> NAME/KEY: misc_feature
<222> LOCATION: (21)..(21)
<223> OTHER INFORMATION: bases at these positions are RNA
<220> FEATURE:
<221> NAME/KEY: misc_feature
<222> LOCATION: (23)..(27)
<223> OTHER INFORMATION: bases at these positions are RNA
<220> FEATURE:
<221> NAME/KEY: misc_feature
<222> LOCATION: (29)..(29)
<223> OTHER INFORMATION: bases at these positions are RNA

<400> SEQUENCE: 16
gagugagugu gugcguggut utagagcta                                      29

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
tacccgggcc gtctgttaga                                                20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18 gaggggaag tcaccgacaa                                                 20

<210> SEQ ID NO 19
<211> LENGTH: 22
<212> TYPE: RNA
```

```
<213> ORGANISM: Artificial sequence
<220> FEATURE:
<223> OTHER INFORMATION: Synthetic oligonucleotide

<400> SEQUENCE: 19
guuuuagagc uaugcuguuu ug                                                22

<210> SEQ ID NO 20
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 20
guuuuaguac ucuguaauuu ua                                                22

<210> SEQ ID NO 21
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 21
guuuuuguac ucucaagauu ua                                                22

<210> SEQ ID NO 22
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 22
guuguagcuc ccauucucau uu                                                22

<210> SEQ ID NO 23
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 23
guuuuagucu cuuuuuaaau uu                                                22

<210> SEQ ID NO 24
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 24
gcugcggauu gcggccgucu cu                                                22

<210> SEQ ID NO 25
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 25
acugggguuc aguucucaaa aa                                                22
```

<210> SEQ ID NO 26
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 26
uaauuucuac uguuguagau                                           20

<210> SEQ ID NO 27
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 27
agaaaugcau gguucucaug c                                         21

<210> SEQ ID NO 28
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 28
aaaauuaccu aguaauuagg u                                         21

<210> SEQ ID NO 29
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 29
ggauuucuac uuuuguagau                                           20

<210> SEQ ID NO 30
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 30
aaauuucuac uuuuguagau                                           20

<210> SEQ ID NO 31
<211> LENGTH: 32
<212> TYPE: RNA
<213> ORGANISM: Artificial sequence
<220> FEATURE:
<223> OTHER INFORMATION: Synthetic oligonucleotide

<400> SEQUENCE: 31
guuucaaucc acgcgcccac gcggggcgcg ac                             32

<210> SEQ ID NO 32
<211> LENGTH: 20
<212> TYPE: RNA
<213> ORGANISM: Artificial sequence
<220> FEATURE:

<223> OTHER INFORMATION: Synthetic oligonucleotide

<400> SEQUENCE: 32
uaauuucuac ucuuguagau                                        20

<210> SEQ ID NO 33
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 33
gaauuucuac uauuguagau                                        20

<210> SEQ ID NO 34
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 34
gaaucucuac ucuuguaga u                                       21

<210> SEQ ID NO 35
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 35
uaauuucuac uuuguagau                                         19

<210> SEQ ID NO 36
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 36
aaauuucuac uguuguaga u                                       21

<210> SEQ ID NO 37
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 37
gaauuucuac uuuuguagau                                        20

<210> SEQ ID NO 38
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 38
uaauuucuac uaaguguaga u                                      21

-continued

```
<210> SEQ ID NO 39
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 39
uaauuucuac uauuguagau                                               20

<210> SEQ ID NO 40
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 40
uaauuucuac uucgguagau                                               20

<210> SEQ ID NO 41
<211> LENGTH: 27
<212> TYPE: DNA
<213> ORGANISM: Artificial sequence
<220> FEATURE:
<223> OTHER INFORMATION: Primer

<400> SEQUENCE: 41
gctgactaag caaagcttcc aaatgac                                       27

<210> SEQ ID NO 42
<211> LENGTH: 25
<212> TYPE: DNA
<213> ORGANISM: Artificial sequence
<220> FEATURE:
<223> OTHER INFORMATION: Primer

<400> SEQUENCE: 42
gatgtcacag aaacactcac cgtag                                         25

<210> SEQ ID NO 43
<211> LENGTH: 42
<212> TYPE: RNA
<213> ORGANISM: Artificial sequence
<220> FEATURE:
<223> OTHER INFORMATION: Synthetic oligonucleotide

<400> SEQUENCE: 43
gacaagguuc auauuuguau guuuuagagc uaugcuguuu ug                      42

<210> SEQ ID NO 44
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(40)
<223> OTHER INFORMATION: bases at these positions are RNA
<220> FEATURE:
<221> NAME/KEY: misc_feature
<222> LOCATION: (42)..(42)
<223> OTHER INFORMATION: bases at these positions are RNA

<400> SEQUENCE: 44
gacaagguuc auauuuguau guuuuagagc uaugcuguuu tg                      42
```

<210> SEQ ID NO 45
<211> LENGTH: 31
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: bases at these positions are RNA
<220> FEATURE:
<221> NAME/KEY: misc_feature
<222> LOCATION: (25)..(29)
<223> OTHER INFORMATION: bases at these positions are RNA
<220> FEATURE:
<221> NAME/KEY: misc_feature
<222> LOCATION: (31)..(31)
<223> OTHER INFORMATION: bases at these positions are RNA

<400> SEQUENCE: 45
gacaagguuc auauuuguau guutagagct a        31

<210> SEQ ID NO 46
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(24)
<223> OTHER INFORMATION: bases at these positions are RNA
<220> FEATURE:
<221> NAME/KEY: misc_feature
<222> LOCATION: (26)..(40)
<223> OTHER INFORMATION: bases at these positions are RNA
<220> FEATURE:
<221> NAME/KEY: misc_feature
<222> LOCATION: (42)..(42)
<223> OTHER INFORMATION: bases at these positions are RNA

<400> SEQUENCE: 46
gacaagguuc auauuuguau guuutagagc uaugcuguuu tg        42

<210> SEQ ID NO 47
<211> LENGTH: 20
<212> TYPE: DNA
<213> ORGANISM: Artificial sequence
<220> FEATURE:
<223> OTHER INFORMATION: Primer

<400> SEQUENCE: 47
ctgggactca ggcgggtcac        20

<210> SEQ ID NO 48
<211> LENGTH: 25
<212> TYPE: DNA
<213> ORGANISM: Artificial sequence
<220> FEATURE:
<223> OTHER INFORMATION: Primer

<400> SEQUENCE: 48
cctcacacaa cagcttcatg tcagc        25

<210> SEQ ID NO 49
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 49
taatttctac tcttgtagat ctgatggtcc atgtctgtta ctc        43

<210> SEQ ID NO 50
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 50
ttctactctt gtagatctga tggtccatgt ctgttactc              39

<210> SEQ ID NO 51
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 51
taatttctac tcttgtagat ctgatggtcc atgtctgtta            40

<210> SEQ ID NO 52
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 52
ttctactctt gtagatctga tggtccatgt ctgt                   34

<210> SEQ ID NO 53
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 53
taatttctac tcttgtagat ctgatggtcc atgtctgt              38

<210> SEQ ID NO 54
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 54
ttctactctt gtagatctga tggtccatgt ctgtta                36

<210> SEQ ID NO 55
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 55
aatttctact cttgtagatc tgatggtcca tgtctgt               37

<210> SEQ ID NO 56

```
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 56
atttctactc ttgtagatct gatggtccat gtctgt                                 36

<210> SEQ ID NO 57
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 57
tttctactct tgtagatctg atggtccatg tctgt                                  35

<210> SEQ ID NO 58
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 58
aatttctact cttgtagatc tgatggtcca tgtctgttac tc                          42

<210> SEQ ID NO 59
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 59
atttctactc ttgtagatct gatggtccat gtctgttact c                           41

<210> SEQ ID NO 60
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 60
tttctactct tgtagatctg atggtccatg tctgttactc                             40

<210> SEQ ID NO 61
<211> LENGTH: 20
<212> TYPE: DNA
<213> ORGANISM: Artificial sequence
<220> FEATURE:
<223> OTHER INFORMATION: Primer

<400> SEQUENCE: 61
ctgaggctag aggactgagc                                                   20

<210> SEQ ID NO 62
<211> LENGTH: 21
<212> TYPE: DNA
<213> ORGANISM: Artificial sequence
<220> FEATURE:
<223> OTHER INFORMATION: Primer

<400> SEQUENCE: 62
```

```
cagacggcta gatgagcaga g                                              21

<210> SEQ ID NO 63
<211> LENGTH: 42
<212> TYPE: RNA
<213> ORGANISM: Artificial sequence
<220> FEATURE:
<223> OTHER INFORMATION: Synthetic oligonucleotide

<400> SEQUENCE: 63
accgcagcca cgcagagcag guuuuagagc uaugcuguuu ug                       42

<210> SEQ ID NO 64
<211> LENGTH: 115
<212> TYPE: DNA
<213> ORGANISM: Artificial sequence
<220> FEATURE:
<223> OTHER INFORMATION: Synthetic oligonucleotide

<400> SEQUENCE: 64
gttggaacca ttcaaaacag catagcaagt taaaataagg ctagtccgtt atcaacttgg    60
ccaacatgag gatcacccat gtctgcaggg ccaagtggca ccgagtcggt gcttt         115

<210> SEQ ID NO 65
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 65
ggaaccattc aaaacagcat agcaagttaa ataaggcta gtccgttatc aacttgaaaa    60
agt                                                                  63

<210> SEQ ID NO 66
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 66
caaaacagca tagcaagtta aaataaggct agtccgttat caacttgaaa aagt          54

<210> SEQ ID NO 67
<211> LENGTH: 24
<212> TYPE: DNA
<213> ORGANISM: Artificial sequence
<220> FEATURE:
<223> OTHER INFORMATION: Primer

<400> SEQUENCE: 67
cttgctggac tggtatttgt gtct                                           24

<210> SEQ ID NO 68
<211> LENGTH: 25
<212> TYPE: DNA
<213> ORGANISM: Artificial sequence
<220> FEATURE:
<223> OTHER INFORMATION: Primer

<400> SEQUENCE: 68
agaactttga ccatcagagg acact                                          25
```

```
<210> SEQ ID NO 69
<211> LENGTH: 22
<212> TYPE: DNA
<213> ORGANISM: Artificial sequence
<220> FEATURE:
<223> OTHER INFORMATION: Probe

<400> SEQUENCE: 69
ccctacgggc accggtgaat cc                                              22

<210> SEQ ID NO 70
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 70
gacaaggttc atatttgtat gttttagagc tatgctgttt tg                        42

<210> SEQ ID NO 71
<211> LENGTH: 32
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: bases at these positions are RNA
<220> FEATURE:
<221> NAME/KEY: misc_feature
<222> LOCATION: (32)..(32)
<223> OTHER INFORMATION: bases at these positions are RNA

<400> SEQUENCE: 71
accgcagcca cgcagagcag guuutagagc ta                                   32

<210> SEQ ID NO 72
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(40)
<223> OTHER INFORMATION: bases at these positions are RNA
<220> FEATURE:
<221> NAME/KEY: misc_feature
<222> LOCATION: (42)..(42)
<223> OTHER INFORMATION: bases at these positions are RNA

<400> SEQUENCE: 72
accgcagcca cgcagagcag guuuuagagc uaugcuguuu tg                        42
```